United States Patent
Rajan et al.

(10) Patent No.: US 12,379,373 B2
(45) Date of Patent: Aug. 5, 2025

(54) APPARATUS, SYSTEMS, AND METHODS FOR QUANTIFYING INFECTIOUS AGENTS

(71) Applicant: Avails Medical, Inc., Menlo Park, CA (US)

(72) Inventors: Nitin K. Rajan, Palo Alto, CA (US); Oren S. Knopfmacher, San Francisco, CA (US); Meike Herget, Woodside, CA (US)

(73) Assignee: Avails Medical, Inc., Menlo Park, CA (US)

( * ) Notice: Subject to any disclaimer, the term of this patent is extended or adjusted under 35 U.S.C. 154(b) by 964 days.

(21) Appl. No.: 17/335,726

(22) Filed: Jun. 1, 2021

(65) Prior Publication Data

US 2021/0325371 A1    Oct. 21, 2021

Related U.S. Application Data

(63) Continuation of application No. PCT/US2019/063956, filed on Dec. 2, 2019.

(60) Provisional application No. 62/774,631, filed on Dec. 3, 2018.

(51) Int. Cl.
    G01N 33/50    (2006.01)
    G01N 1/38     (2006.01)
    G06F 17/18    (2006.01)

(52) U.S. Cl.
    CPC ........... *G01N 33/5091* (2013.01); *G01N 1/38* (2013.01); *G06F 17/18* (2013.01)

(58) Field of Classification Search
    None
    See application file for complete search history.

(56) References Cited

U.S. PATENT DOCUMENTS

| | | |
|---|---|---|
| 3,743,581 A | 7/1973 | Cady et al. |
| 4,200,493 A | 4/1980 | Wilkins et al. |
| 4,209,586 A | 6/1980 | Noller |
| 4,236,893 A | 12/1980 | Rice |
| 4,314,821 A | 2/1982 | Rice |
| 4,321,322 A | 3/1982 | Ahnell |
| 4,448,534 A | 5/1984 | Wertz et al. |
| 4,615,978 A | 10/1986 | Sandine et al. |
| 4,735,906 A | 4/1988 | Bastiaans |
| 4,767,719 A | 8/1988 | Finlan |
| 4,789,804 A | 12/1988 | Karube et al. |
| 4,822,566 A | 4/1989 | Newman |
| 4,965,193 A | 10/1990 | Chen |
| 4,977,247 A | 12/1990 | Fahnestock et al. |
| 5,064,756 A | 11/1991 | Carr et al. |
| 5,077,210 A | 12/1991 | Eigler et al. |
| 5,111,221 A | 5/1992 | Fare et al. |
| 5,172,332 A | 12/1992 | Hungerford et al. |
| 5,182,005 A | 1/1993 | Schwiegk et al. |
| 5,218,304 A | 6/1993 | Kinlen et al. |
| 5,356,782 A | 11/1994 | Moorman et al. |
| 5,447,845 A | 9/1995 | Chu et al. |
| 5,821,399 A | 10/1998 | Zelin |
| 5,922,537 A | 7/1999 | Ewart et al. |
| 6,280,586 B1 | 8/2001 | Wolf et al. |
| 6,368,795 B1 | 4/2002 | Hefti |
| 6,391,558 B1 | 5/2002 | Henkens et al. |
| 6,391,577 B1 | 5/2002 | Mikkelsen et al. |
| 6,548,263 B1 | 4/2003 | Kapur et al. |
| 6,548,311 B1 | 4/2003 | Knoll |
| 6,780,307 B2 | 8/2004 | Kidwell |
| 6,863,792 B1 | 3/2005 | Madou et al. |
| 7,745,272 B2 | 6/2010 | Van de Walle et al. |
| 8,508,100 B2 | 8/2013 | Lee et al. |
| 8,728,844 B1 | 5/2014 | Liu et al. |
| 9,377,456 B1 | 6/2016 | Herget et al. |
| 9,702,847 B2 | 7/2017 | Herget et al. |
| 9,766,201 B2 | 9/2017 | Herget et al. |
| 9,944,969 B2 | 4/2018 | Knopfmacher et al. |

(Continued)

FOREIGN PATENT DOCUMENTS

| | | |
|---|---|---|
| CN | 101057143 | 10/2007 |
| CN | 101852765 | 10/2010 |

(Continued)

OTHER PUBLICATIONS

Halvorson et al. "Application of Statistics to Problems in Bacteriology" (1932), J Bacteriology, vol. XXV, No. 2: 101-121. (Year: 1932).*
Thomas et al. "Optimization of single plate-serial dilution spotting (SP-SDS) with sample anchoring as an assured method for bacterial and yeast cfu enumeration and single colony isolation from diverse samples" (2015), Biotech Reports, vol. 8: 45-55 (Year: 2015).*
Uria et al. "Miniaturized metal oxide pH sensors for bacteria detection" (2016), Talanta, vol. 147: 364-369. (Year: 2016).*
Jiang et al. "A User-Friendly Robotic Sample Preparation Program for Fully Automated Biological Sample Pipetting and Dilution to Benefit the Regulated Bioanalysis", (2012) J Laboratory Automation, vol. 17, No. 3: 211-221 (Year: 2012).*

(Continued)

*Primary Examiner* — Teresa E Knight
(74) *Attorney, Agent, or Firm* — Levine Bagade Han LLP

(57)    ABSTRACT

Various methods, devices, and systems for determining the concentration of infectious agent in a target sample are disclosed herein. In one embodiment, a method for determining the concentration of an infectious agent of an unknown strain can include diluting aliquots of a target sample comprising the infectious agent by different dilution factors to yield diluted samples. The method can also include determining the time it takes a solution characteristic of each of the diluted samples to undertake a predetermined threshold change. The method can also include determining the concentration of the infectious agent of the unknown strain by taking into account the different dilution factors, the monitored times, and certain curve fitting parameters calculated from predetermined calibration curves generated for infectious agents of different known strains.

13 Claims, 14 Drawing Sheets

(56) References Cited

U.S. PATENT DOCUMENTS

| | | |
|---|---|---|
| 9,963,733 B2 | 5/2018 | Knopfmacher et al. |
| 10,060,916 B2 | 8/2018 | Knopfmacher |
| 10,174,356 B2 | 1/2019 | Knopfmacher et al. |
| 10,254,245 B2 | 4/2019 | Knopfmacher et al. |
| 11,385,200 B2 | 7/2022 | Knopfmacher et al. |
| 11,655,494 B2 | 5/2023 | Knopfmacher et al. |
| 2002/0127623 A1 | 9/2002 | Minshull et al. |
| 2003/0073071 A1 | 4/2003 | Fritz et al. |
| 2003/0109056 A1 | 6/2003 | Vossmeyer et al. |
| 2003/0119208 A1 | 6/2003 | Yoon et al. |
| 2004/0195098 A1 | 10/2004 | Broadley et al. |
| 2005/0116263 A1 | 6/2005 | Lu et al. |
| 2006/0088839 A1 | 4/2006 | Matsui et al. |
| 2006/0102935 A1 | 5/2006 | Yitzchaik et al. |
| 2006/0197118 A1 | 9/2006 | Migliorato et al. |
| 2006/0246426 A1 | 11/2006 | Woodbury et al. |
| 2006/0286548 A1 | 12/2006 | Liposky |
| 2007/0037225 A1 | 2/2007 | Metzger et al. |
| 2007/0054396 A1 | 3/2007 | Peppers et al. |
| 2007/0072187 A1 | 3/2007 | Blok et al. |
| 2008/0012007 A1 | 1/2008 | Li et al. |
| 2008/0199863 A1 | 8/2008 | Haake et al. |
| 2009/0008247 A1 | 1/2009 | Chen et al. |
| 2009/0020438 A1 | 1/2009 | Hodges |
| 2009/0273354 A1 | 11/2009 | Dhirani et al. |
| 2010/0025660 A1 | 2/2010 | Jain et al. |
| 2010/0137143 A1 | 6/2010 | Rothberg et al. |
| 2010/0194409 A1 | 8/2010 | Gao et al. |
| 2011/0068372 A1 | 3/2011 | Ren et al. |
| 2011/0306032 A1 | 12/2011 | Galiano et al. |
| 2012/0032235 A1 | 2/2012 | Bikumandla |
| 2012/0077692 A1 | 3/2012 | Hassibi et al. |
| 2012/0088682 A1 | 4/2012 | Rothberg et al. |
| 2012/0143027 A1 | 6/2012 | Phillips et al. |
| 2012/0153262 A1 | 6/2012 | Paranjape et al. |
| 2012/0153407 A1 | 6/2012 | Chang et al. |
| 2012/0165246 A1 | 6/2012 | Lindner et al. |
| 2012/0168306 A1 | 7/2012 | Hassibi et al. |
| 2012/0208291 A1 | 8/2012 | Davis et al. |
| 2012/0214172 A1 | 8/2012 | Chen et al. |
| 2012/0261274 A1 | 10/2012 | Rearick et al. |
| 2012/0256166 A1 | 11/2012 | Chen et al. |
| 2012/0279859 A1 | 11/2012 | Rothberg et al. |
| 2013/0089883 A1 | 4/2013 | Dallenne et al. |
| 2013/0089932 A1 | 4/2013 | Wu et al. |
| 2013/0096013 A1 | 4/2013 | Esfandyarpour et al. |
| 2013/0105868 A1 | 5/2013 | Kalnitsky et al. |
| 2013/0217063 A1 | 8/2013 | Metzger et al. |
| 2014/0011218 A1 | 1/2014 | Han et al. |
| 2014/0057339 A1 | 2/2014 | Esfandyarpour et al. |
| 2014/0134656 A1 | 5/2014 | Dortet et al. |
| 2014/0186215 A1 | 6/2014 | Shinta et al. |
| 2014/0191294 A1 | 7/2014 | Bikumandla et al. |
| 2014/0231256 A1 | 8/2014 | Packingham et al. |
| 2014/0349005 A1 | 11/2014 | Everett et al. |
| 2015/0355129 A1 | 12/2015 | Knopfmacher |
| 2016/0039657 A1 | 2/2016 | Jain et al. |
| 2016/0068417 A1 | 3/2016 | Buschmann |
| 2016/0187332 A1 | 6/2016 | Herget et al. |
| 2016/0187334 A1 | 6/2016 | Herget et al. |
| 2016/0208306 A1 | 7/2016 | Pollak et al. |
| 2016/0209356 A1 | 7/2016 | Herget et al. |
| 2016/0266102 A1 | 9/2016 | Knopfmacher |
| 2016/0369318 A1 | 12/2016 | Carlisle et al. |
| 2017/0058313 A1 | 3/2017 | Knopfmacher et al. |
| 2017/0059508 A1 | 3/2017 | Knopfmacher et al. |
| 2017/0212075 A1 | 7/2017 | Knopfmacher et al. |
| 2017/0336348 A1 | 11/2017 | Herget et al. |
| 2017/0336384 A1 | 11/2017 | Ino et al. |
| 2017/0342459 A1 | 11/2017 | Knopfmacher et al. |
| 2018/0195106 A1 | 7/2018 | Knopfmacher et al. |
| 2018/0364221 A1 | 12/2018 | Knopfmacher |
| 2019/0046984 A1 | 2/2019 | Kelley et al. |
| 2019/0136290 A1 | 5/2019 | Knopfmacher et al. |
| 2019/0293529 A1 | 9/2019 | Rajan et al. |
| 2019/0310214 A1 | 10/2019 | Herget et al. |
| 2020/0150082 A1 | 5/2020 | Knopfmacher et al. |
| 2020/0224241 A1 | 7/2020 | Knopfmacher et al. |
| 2022/0317087 A1 | 10/2022 | Knopfmacher et al. |
| 2023/0250463 A1 | 8/2023 | Knopfmacher et al. |

FOREIGN PATENT DOCUMENTS

| | | |
|---|---|---|
| CN | 101852765 A | 10/2010 |
| CN | 105473740 | 4/2016 |
| CN | 107205808 | 9/2017 |
| EP | 0235024 | 9/1987 |
| EP | 1460130 | 9/2004 |
| EP | 2172767 | 4/2010 |
| JP | 1988-066454 | 3/1988 |
| JP | 1996-0886771 | 4/1996 |
| JP | 2002-112761 | 4/2002 |
| JP | 2003-052392 | 2/2003 |
| JP | 2005-287452 | 10/2005 |
| JP | 2006-511818 | 4/2006 |
| JP | 2011-58900 | 3/2011 |
| JP | 2011-062195 | 3/2011 |
| JP | 2012-024085 | 2/2012 |
| JP | 2011-085038 | 11/2012 |
| WO | WO 19992/009700 | 6/1992 |
| WO | WO 2003/044530 | 5/2003 |
| WO | WO 2003/052097 | 6/2003 |
| WO | WO 2004/077052 | 9/2004 |
| WO | WO 2006/102695 | 10/2006 |
| WO | WO 2007/035814 | 3/2007 |
| WO | WO 2009/021908 | 2/2009 |
| WO | WO 2010/062001 | 6/2010 |
| WO | WO 2012/078340 | 6/2012 |
| WO | WO 2013/096404 | 6/2013 |
| WO | WO 2014/080292 | 5/2014 |
| WO | WO 2014/134431 | 9/2014 |
| WO | WO 2015/077632 | 5/2015 |
| WO | WO 2015/188002 | 12/2015 |
| WO | WO 2016/005743 | 1/2016 |
| WO | WO 2016/028233 | 2/2016 |
| WO | WO 2016/044417 | 3/2016 |
| WO | WO 2016/061453 | 4/2016 |
| WO | WO 2016/065475 | 5/2016 |
| WO | WO 2016/109569 | 7/2016 |
| WO | WO 2017/035393 | 3/2017 |
| WO | WO 2017/107333 | 6/2017 |
| WO | WO 2017/132095 | 8/2017 |
| WO | WO 2017/209839 | 12/2017 |
| WO | WO 2018/111234 | 6/2018 |
| WO | WO 2018/145338 | 8/2018 |
| WO | WO 2019/005296 | 1/2019 |
| WO | WO 2019/246208 | 1/2019 |
| WO | WO 2019/070739 | 4/2019 |
| WO | WO 2019/113226 | 6/2019 |
| WO | WO 2020/117650 | 6/2020 |

OTHER PUBLICATIONS

Rael et al. "Plasma Oxidation-Reduction Potential and Protein Oxidation in Traumatic Brain Injury" (2009) J Neurotrauma, vol. 26, No. 8: 1203-1211 (Year: 2009).*

Dutton 1978 (Redox potentiometry: Determination of midpoint potentials of oxidation-reduction components of biological electron-transfer systems; In Methods in Enzymology, 54:411-435) (Year: 1978).

Kang et al. "Survey of Redox-Active Moieties for Application in Multiplexed Electrochemical Biosensors", Anal. Chem., vol. 88, pp. 10452-10458, 2016.

Wan et al., 2011 (Impedimetric immunosensor doped with reduced graphene sheets fabricated by controllable electrodeposition for the non-labelled detection of bacteria; Biosensors and Bioelectronics 26 (2011) 1959-1964). (Year: 2011).

Zhou, Yong-Jun et al.: Real-time Detection System for Amount of Bacteria Based on an Electrochemical Sensor, Instrument Technique and Sensor, vol. 2, No. 2, Feb. 28, 2014 (Feb. 28, 2014), pp. 71-72 and 86.

(56) References Cited

OTHER PUBLICATIONS

Zuhri et al. 2016 (Effect of Methylene Blue Addition as a Redox Mediator on Performance of Microbial Desalination Cell by Utilizing Tempe Wastewater; International Journal of Technology 6: 952-961). (Year: 2016).
Berney et al. "A DNA diagnostic biosensor: development, characterization and performance" Sensors and Actuators B: Chemical: International Journal Devoted to Research and Development of Physical and Chemical Transducers, Elsevier BV, NL, vol. 68, No. 1-3, Aug. 25, 2000, pp. 100-108.
Dortet, Laurent et al., "Bloodstream Infections Caused by *Pseudomonas* spp.: How to Detect Carbapenemase Producers Directly from Blood Cultures", Journal of Clinical Microbiology, 52(4):1269-1273, Apr. 2014.
Dortet, Laurent et al., "CarbAcineto NP Test for Rapid Detection of Carbapenemase-Producing *Acinetobacter* spp.", Journal of Clinical Microbiology, 52(7):2359-2364, Jul. 2014.
Dortet, Laurent et al., "Evaluation of the RAPIDECw CARBA NP, the Rapid CARB Screenw and the Carba NP test for biochemical detection of carbapenemase-producing Enterobacteriaceae", J Antimicrob Chemother, 70:3014-3022, 2015.
Dortet, Laurent et al., "Further Proofs of Concept for the Carba NP Test", Antimicrobial Agents and Chemotherapy, 58(2):1269, Feb. 2014.
Dortet, Laurent et al., "Rapid Identification of Carbapenemase Types in Enterobacteriaceae and *Pseudomonas* spp. by Using a Biochemical Test", Antimicrobial Agents and Chemotherapy, 56(12):6437-6440, Dec. 2012.
Estrela, Pedro et al., "Label-Free Sub-picomolar Protein Detection with Field-Effect Transistors," Analytical Chemistry, vol. 82, No. 9, May 1, 2010, 3531-3536.
Hammock, Mallory L. et al., "Electronic readout ELISA with organic field-effect transistors as a prognostic test for preeclampsia," Advanced Materials, 26: 6138-6144. doi: 10.1002/adma. 201401829.
Kumar et al., "Sensitivity Enhancement Mechanisms in Textured Dielectric Based Electrolyte-Insulator-Semiconductor (EIS) Sensors," *ECS Journal of Solid State Science and Technology*, 4(3):N18-N23 (2015).
Mathias, W. et al., "Selective Sodium Sensing with Gold-Coated Silicon Nanowire Field-Effect Transistors in a Differential Setup," ACS Nano 7, 5978-5983 (2013).
Nordmann, Patrice et al., "Strategies for identification of carbapenemase-producing Enterobacteriaceae", J Antimicrob Chemother, 68:487-489, 2013.
Oliu et al., "Impedimetric Sensors for Bacteria Detection," Biosensors—Micro and Nanoscale Applications, Chpt. 9 (Sep. 2015) p. 257-288.
Poghossian et al., "Penicillin Detection by Means of Field-Effect Based Sensors: EnFET, Capacitive EIS Sensor or LAPS?", *Sensors and Actuators B*, 78:237 (2001).
Poirel, Laurent et al., "Rapidec Carba NP Test for Rapid Detection of Carbapenemase Producers", Journal of Clinical Microbiology, 53(9):3003-3008, Sep. 2015.
Pourciel-Gouzy M L et al: "pH-ChemFET-based analysis devices for the bacterial activity monitoring." Sensors and Actuators B: Chemical: International Journal Devoted to Research and Development of Physical and Chemical Transducers, Elsevier BV, NL, vol. 134, No. 1 Aug. 28, 2008, pp. 339-344.
Salm, Eric et al., "Electrical Detection of Nucleic Acid Amplification Using an On-Chip Quasi-Reference Electrode and a PVC REFET," dx.doi.org/10.1021/ac500897t, *Anal. Chem.*, 2014, 86, 6968-6975.
Schoning, Michael J., "'Playing Around' with Field-Effect Sensors on the Basis of EIS Structures, LAPS and ISFETs," *Sensors*, 5:126-138 (2005).
Ivnitsky D et al: "Biosensors for Detection of Pathogenic Bacteria", Biosensors and Bioelectronics, Elsevier Science Ltd. UK, Amsterdam, NL, vol. 14, No. 7, Oct. 1, 1999, pp. 599-624.
J. Parce et al: "Detection of cell-affecting agents with a silicon biosensor", Science, vol. 246, No. 4927, Oct. 13, 1989 (Oct. 13, 1989), pp. 243-247.
Grossi Marco et al. "Bacterial concentration detection using a portable embedded sensor system for environmental monitoring", 2017 7th IEE International Workshop on Advances in Senors and Interfaces (IWASI), IEEE, Jun. 15, 2017, pp. 246-251.
Yu Allen C et al: Moni tori ng bacterial growth using tunable resistive pulse sensing with a pore-based technique11 , Applied Microbiology and Biotechnology, Springer Berlin Heidelberg, Berlin/Heidelberg, vol. 98, No. 2, Nov. 29, 2013, pp. 855-862.
Xuzhi Zhang et al: Online Monitoring of Bacterial Growth with an Electrical Sensor11 , 171. Analytical Chemistry, vol. 90, No. 10, Apr. 24, 2018 (Apr. 24, 2018), pp. 6006-6011.
Zhou, Yong-Jun et al.: Real-time Detection System for Amount of Bacteria Based on an Electrochemical Sensor, Instrument Technique and Sensor, vol. 2, No. 2, Feb. 28, 2014 (2014-02-28), pp. 71-72 and 86.
Kazuo Iwata, Akira Matsuda, Effect of Mixed Culture of Redox Potentials of Candida and Various Bacteria, Sep. 1962, Fungus and Fungus Disease, vol. 3, No. 2, pp. 56-60.
"MINIFOR Laboratory Fermentor - Bioreactor", pp. 1-7, Feb. 24, 2017, Retrieved from the Internet: https://www.fermenter.net/pdf/LAMBDA_MINIFOR_laboratory_fermentor_description .pdf.
Ingraham 1933 (The Bacteriostatic Action of Gentian Violet and its Dependence on the Oxidation-Reduction Potential; Journal of Bacteriology, vol. XXVI, No. 6. p 573-598) (Year: 1933).
Kotzian et al. 2007 (Oxides of platinum metal group as potential catalysts in carbonaceous amperometric biosensors based on oxidases; Sensors and Actuators B 124: 297-302). (Year: 2007).
Vila et al. 2016 (Escherichia coli: an old friend with new tidings; FEMS Microbiology Reviews; 40: 437-463). (Year: 2016).

\* cited by examiner

APPARATUS, SYSTEMS, AND METHODS FOR QUANTIFYING INFECTIOUS AGENTS

CROSS-REFERENCE TO RELATED APPLICATIONS

This application is a continuation of PCT Application No. PCT/US2019/063956 filed on Dec. 2, 2019, which claims the benefit of U.S. Provisional Application No. 62/774,631 filed on Dec. 3, 2018, the contents of which are incorporated herein by reference in their entities.

TECHNICAL FIELD

The present disclosure relates generally to in vitro quantification of microorganisms or infectious agents and, more specifically, to apparatus, systems, and methods for determining the concentration of microorganisms or infectious agents in biological samples.

BACKGROUND

Infections caused by anti-infective resistant microorganisms or infectious agents are a significant problem for healthcare professionals in hospitals, nursing homes, and other healthcare environments. Rapid detection of the susceptibility of such infectious agents to antibiotics or other anti-infectives is crucial in order to prevent the spread of their resistance profiles. The first step in most anti-infective susceptibility testing protocols is to accurately quantify the amount of infectious agents in a particular sample.

Existing methods and instruments used to quantify infectious agents include costly and labor intensive microbial culturing techniques. However, those methods often require manual interpretation by skilled personnel and are prone to technical or clinician error. In addition, certain biological samples suspected of harboring infectious agents, such as samples containing animal or human blood, are often difficult to assess using prevailing optical techniques given the samples' opacity. Moreover, such optical techniques often require bulky and expensive detection equipment.

As a result of the above limitations and restrictions, there is a need for improved apparatus, systems, and methods to quickly and effectively quantify infectious agents in a wide variety of biological samples.

SUMMARY

A method of determining a concentration of an infectious agent of an unknown strain in a target sample is disclosed. The method comprises diluting a first aliquot of the target sample comprising the infectious agents of the unknown strain by a first dilution factor ($DF_1$) to yield a first diluted sample and diluting a second aliquot of the target sample comprising the infectious agents of the unknown strain by a second dilution factor ($DF_2$) to yield a second diluted sample. The first aliquot and the second aliquot of the sample can be diluted with growth media. The method also comprises determining a first time-to-detection ($TTD_1$) representing the time it takes a solution characteristic of the first diluted sample to undertake a predetermined threshold change and determining a second time-to-detection ($TTD_2$) representing the time it takes the solution characteristic of the second diluted sample to undertake the predetermined threshold change. The method further comprises calculating an average calibration curve slope ($m_{avg}$) and an average calibration curve y-intercept ($b_{avg}$) from equation parameters obtained from multiple calibration curves representing growth behavior of one or more infectious agents of different known strains. The method also comprises calculating a corrected calibration curve slope ($m_{corr}$) using at least the $TTD_2$, the $TTD_1$, the $DF_2$, and the $DF_1$ and calculating a corrected calibration curve y-intercept ($b_{corr}$) using at least the $b_{avg}$, the $m_{corr}$, and the $m_{avg}$. The method further comprises determining the concentration of the infectious agent of the unknown strain in the target sample using at least the $m_{corr}$, the $b_{corr}$, and either the $TTD_1$ and the $DF_1$ or the $TTD_2$ and the $DF_2$.

The one or more infectious agents of the different known strains can comprise at least a first infectious agent and a second infectious agent. In some embodiments, the first infectious agent is a different species from the second infectious agent. In other embodiments, the infectious agents of the different known strains are the same species as the infectious agent of the unknown strain.

The method further comprises generating the multiple calibration curves prior to calculating the $m_{avg}$ and the $b_{avg}$ by preparing cultures comprising the one or more infectious agents of the different known strains. The prepared cultures comprise different initial concentrations ($N_{initial}$) of an infectious agent of a known strain. The method further comprises monitoring, using one or more sensors, changes in the solution characteristics of each of the prepared cultures over time and determining a calibration time-to-detection ($TTD_{calibration}$) of each of the prepared cultures representing the time it takes the solution characteristic of each of the prepared cultures to undertake the predetermined threshold change. The method further comprises fitting each of the multiple calibration curves to $TTD_{calibration}$ data and $N_{initial}$ data related to a specific known strain using the relationship: $TTD_{calibration} = m_{strain\_specific} \times \log_a(N_{initial}) + b_{strain\_specific}$. In this relationship, "a" is any positive real number other than 1, "$m_{strain\_specific}$" is a strain-specific calibration curve slope, and "$b_{strain\_specific}$" is a strain-specific calibration curve y-intercept.

In some embodiments, calculating the $m_{avg}$ comprises taking an average of multiple $m_{strain\_specific}$ values and calculating the $b_{avg}$ comprises taking an average of multiple $b_{strain\_specific}$ values. Moreover, calculating the $m_{corr}$ comprises involves using the relationship:

$$m_{corr} = \frac{-(TTD2 - TTD1)}{\log_a\left(\frac{DF2}{DF1}\right)}.$$

In some embodiments, calculating the $b_{corr}$ comprises using the relationship:

$$b_{corr} = \frac{m_{corr}}{m_{avg}} \times b_{avg}.$$

Determining the concentration of the infectious agent of the unknown strain ($Conc_{target}$) can comprise using the relationship:

$$Conc_{target} = DF_1 \times a^{\left(\frac{TTD_1 - b_{corr}}{m_{corr}}\right)}.$$

Determining the concentration of the infectious agent of the unknown strain ($\text{Conc}_{target}$) can comprise using the relationship:

$$\text{Conc}_{target} = DF_2 \times a^{\left(\frac{TTD_2 - b_{corr}}{m_{corr}}\right)}.$$

In some embodiments, the solution characteristic can be an oxidation reduction potential (ORP) and the solution characteristic can be monitored by at least one computing device communicatively coupled to at least a first ORP sensor and a second ORP sensor. Each of the first ORP sensor and the second ORP sensor can comprise a redox-active material. The first ORP sensor can be in fluid communication with the first diluted sample and the second ORP sensor can be in fluid communication with the second diluted sample. The ORP can be monitored in the absence of any added reporter molecules in any of the first diluted sample or the second diluted sample.

The first ORP sensor and the second ORP sensor can each comprise at least an active electrode and a reference electrode. The predetermined threshold change can be a change in the ORP of between approximately −100 mV and −700 mV. The redox-active material can comprise a gold layer, a platinum layer, a metal oxide layer, a carbon layer, or a combination thereof.

In other embodiments, the solution characteristic can be pH and the solution characteristic can be monitored by at least one computing device communicatively coupled to at least a first pH sensor and a second pH sensor. Each of the first pH sensor and the second pH sensor can comprise a functionalization layer. The first pH sensor can be in fluid communication with the first diluted sample and the second pH sensor can be in fluid communication with the second diluted sample.

The first pH sensor and the second pH sensor each can comprise at least an active electrode and a reference electrode. The predetermined threshold change can be approximately a change in pH of between approximately −0.01 to −3.0.

The target sample can comprise a bodily fluid, a wound swab or sample, a rectal swab or sample, another type of biological sample, a culture derived therefrom, or a combination thereof. The bodily fluid can comprise urine, blood, sputum, saliva, breast milk, spinal fluid, semen, vaginal secretions, synovial fluid, pleural fluid, peritoneal fluid, pericardial fluid, amniotic fluid, cultures of bodily fluid that have tested positive for infectious agent growth, or a combination thereof. The infectious agent can comprise bacteria, fungus, mold, or a combination thereof.

A system to determine a concentration of an infectious agent of an unknown strain in a target sample, comprising a metering conduit configured to dilute a first aliquot of the target sample comprising the infectious agent of the unknown strain by a first dilution factor ($DF_1$) to yield a first diluted sample and dilute a second aliquot of the target sample comprising the infectious agent of the unknown strain by a second dilution factor ($DF_2$) to yield a second diluted sample. The first aliquot and the second aliquot of the target sample can be diluted with growth media. The system can also comprise a first sensor configured to detect a change in a solution characteristic of the first diluted sample and a second sensor configured to detect a change in the solution characteristic of the second diluted sample. The system can further comprise one or more sample delivery conduits configured to introduce the first diluted sample to the first sensor and introduce the second diluted sample to the second sensor and a computing device communicatively coupled to the first sensor and the second sensor. The computing device can comprise one or more processors. The one or more processors can be programmed to determine a first time-to-detection ($TTD_1$) representing the time it takes the solution characteristic of the first diluted sample to undertake a predetermined threshold change and determine a second time-to-detection ($TTD_2$) representing the time it takes the solution characteristic of the second diluted sample to undertake the predetermined threshold change. The one or more processor can also be programmed to calculate a corrected calibration curve slope ($m_{corr}$) using at least the $TTD_2$, the $TTD_1$, the $DF_2$, and the $DF_1$ and calculate an average calibration curve slope ($m_{avg}$) and an average calibration curve y-intercept ($b_{avg}$) from equation parameters obtained from multiple calibration curves representing growth behavior of infectious agents of different known strains. Furthermore, the one or more processors can be programmed to calculate a corrected calibration curve y-intercept ($b_{corr}$) using at least the $m_{corr}$, the $m_{avg}$, and the $b_{avg}$ and determine the concentration of the infectious agent of the unknown strain in the target sample using at least the $m_{corr}$, the $b_{corr}$, and either the $TTD_1$ and the $DF_1$ or the $TTD_2$ and the $DF_2$.

The one or more infectious agents of the different known strains can comprise at least a first infectious agent and a second infectious agent. The first infectious agent can be a different species from the second infectious agent. In other embodiments, the one or more infectious agents of the different known strains can be the same species as the infectious agent of the unknown strain.

The one or more processors of the computing device can be programmed to generate the multiple calibration curves prior to calculating the $m_{avg}$ and the $b_{avg}$ by monitoring, via one or more sensors communicatively coupled to the computing device, changes in the solution characteristics of prepared cultures comprising the one or more infectious agents of the different known strains. The prepared cultures can comprise different initial concentrations ($N_{initial}$) of an infectious agent of a known strain.

The one or more processors can also be programmed to determine a calibration time-to-detection ($TTD_{calibration}$) of each of the prepared cultures representing the time it takes the solution characteristic of each of the prepared cultures to undertake the predetermined threshold change. Moreover, the one or more processors can be programmed to fit each of the multiple calibration curves to $TTD_{calibration}$ data and $N_{initial}$ data related to a specific known strain using the relationship:

$TTD_{calibration} = m_{strain\_specific} \times \log_a(N_{initial}) + b_{strain\_specific}$, In this relationship, "a" is any positive real number other than 1, "$m_{strain\_specific}$" is a strain-specific calibration curve slope, and "$b_{strain\_specific}$" is a strain-specific calibration curve y-intercept.

The one or more processors can also be programmed to calculate the $m_{avg}$ by taking an average of multiple $m_{strain\_specific}$ values and calculate the $b_{avg}$ by taking an average of multiple $b_{strain\_specific}$ values. The one or more processors can also be programmed to calculate the $m_{corr}$ using the relationship:

$$m_{corr} = \frac{-(TTD2 - TTD1)}{\log_a\left(\frac{DF_2}{DF_1}\right)}.$$

Furthermore, the one or more processors can be programmed to calculate the $b_{corr}$ using the relationship:

$$b_{corr} = \frac{m_{corr}}{a_{avg}} \times b_{avg}.$$

In addition, the one or more processors can be programmed to determine the concentration of the target infectious agent of the unknown strain ($Conc_{target}$) using the relationship:

$$Conc_{target} = DF_1 \times a^{\left(\frac{TTD_1 - b_{corr}}{m_{corr}}\right)}.$$

The one or more processors can also be programmed to determine the concentration of the target infectious agent of the unknown strain ($Conc_{target}$) using the relationship:

$$Conc_{target} = DF_2 \times a^{\left(\frac{TTD_2 - b_{corr}}{m_{corr}}\right)}.$$

In some embodiments, the solution characteristic can be an oxidation reduction potential (ORP) and both the first sensor and the second sensor can be ORP sensors. In these embodiments, each of the first sensor and the second sensor can comprise a redox-active material. Moreover, the predetermined threshold change can be a change in the ORP of between approximately −100 mV and −700 mV. The redox-active material can comprise a gold layer, a platinum layer, a metal oxide layer, a carbon layer, or a combination thereof.

In other embodiments, the solution characteristic can be pH and both the first sensor and the second sensor can be pH sensors. In these embodiments, each of the first sensor and the second sensor comprise a functionalization layer.

The predetermined threshold change can be approximately a change in pH of between approximately −0.01 to −3.0. Moreover, the first sensor and the second sensor can each comprise at least an active electrode and a reference electrode.

In some embodiments, the target sample can comprise a bodily fluid, a wound swab or sample, a rectal swab or sample, another type of biological sample, a sample culture derived therefrom, or a combination thereof. The bodily fluid can comprise urine, blood, sputum, saliva, breast milk, spinal fluid, semen, vaginal secretions, synovial fluid, pleural fluid, peritoneal fluid, pericardial fluid, amniotic fluid, cultures of bodily fluid that have tested positive for infectious agent growth, or a combination thereof. The infectious agent can comprise bacteria, fungus, mold, or a combination thereof.

DETAILED DESCRIPTION

Variations of the devices, systems, and methods described herein are best understood from the detailed description when read in conjunction with the accompanying drawings. It is emphasized that, according to common practice, the various features of the drawings may not be to scale. On the contrary, the dimensions of the various features may be arbitrarily expanded or reduced for clarity and not all features may be visible or labeled in every drawing. The drawings are taken for illustrative purposes only and are not intended to define or limit the scope of the claims to that which is shown.

Figure 1:
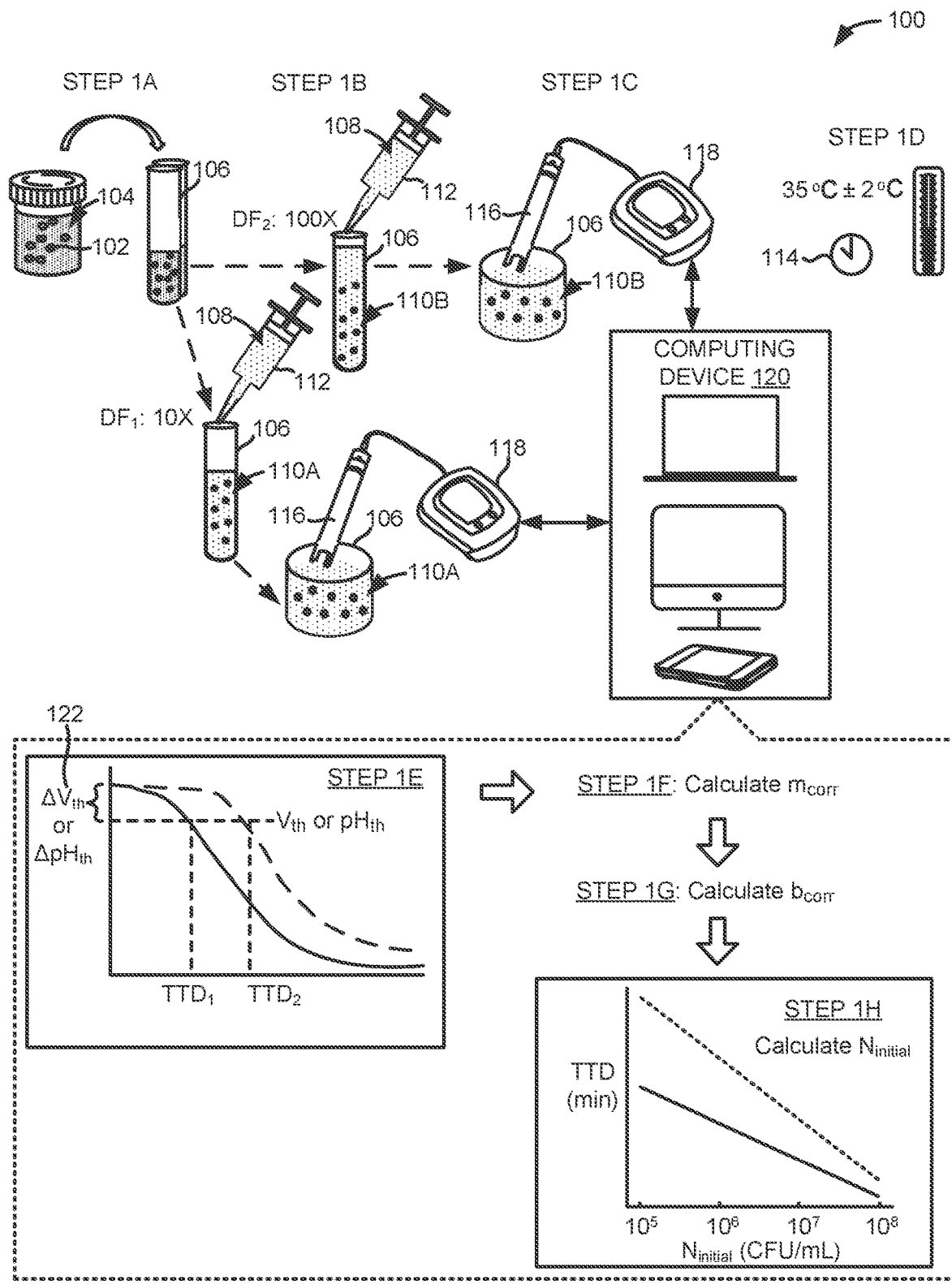
FIG. 1 illustrates certain steps of an example method for determining the concentration of an infectious agent in a target sample.

FIG. 1 illustrates one embodiment of a method 100 for determining the concentration of an infectious agent 102 in a target sample 104. In some embodiments, the method 100 can be used to determine the concentration of an infectious agent 102 of a known species but an unknown strain. For example, the species of the infectious agent 102 in the target sample 104 can be determined using biochemical tests using specific substrates (both for metabolism and as substrates for specific enzymes), mass spectrometry, genotyping, phenotypic analysis from culture plates, test kits comprising engineered phages, or a combination thereof.

Once the species of the infectious agent 102 in the target sample 104 is determined, the method 100 can comprise introducing aliquots of the target sample 104 into reaction vessels 106 in step 1A. The reaction vessels 106 can refer to one or more test tubes, reaction tubes, wells of a high throughput assay plate or well plate such as a 96-well plate, a 192-well plate, or a 384-well plate, culture plates or dishes, microfluidic conduits, or other suitable containers for housing biological samples. One or more fluid delivery conduits 108 can inject, deliver, or otherwise introduce the aliquots of the target sample 104 to the reaction vessels 106. In some embodiments, the species of the infectious agent 102 in the target sample 104 does not need to be determined prior to introducing aliquots of the target sample 104 into reaction vessels 106 in step 1A.

In additional embodiments not shown in FIG. 1, a stimulus solution can be added to the target sample 104 before introducing aliquots of the target sample 104 to the reaction vessels 106. The stimulus solution can be a nutrient or growth solution. In these and other embodiments, the target sample 104 can also be filtered before step 1A. This filtering step can involve filtering the target sample 104 using an instance of a filter, a microfluidic filter, or a combination thereof to filter out debris, inorganic material, and larger cellular components including blood cells or epithelial cells from the target sample 104.

The target sample 104 can comprise at least one of a biological sample, a bodily fluid, a wound swab or sample, a rectal swab or sample, and a bacterial culture derived from the biological sample, the bodily fluid, the wound swab or sample, or the rectal swab or sample. The bodily fluid can comprise urine, blood, serum, plasma, saliva, sputum, semen, breast milk, joint fluid, spinal fluid such as cerebrospinal fluid, wound material, mucus, fluid accompanying stool, re-suspended rectal or wound swabs, vaginal secretions, synovial fluid, pleural fluid, peritoneal fluid, pericardial fluid, amniotic fluid, cultures of bodily fluid or samples that have tested positive for an infectious agent or infectious agent growth such as blood culture that has tested positive for an infectious agent or infectious agent growth (i.e., positive blood culture), or a combination thereof.

The infectious agents 102 that can be quantified using the methods or systems disclosed herein can be any metabolizing single- or multi-cellular organism including bacteria and fungi. In certain embodiments, the infectious agent 102 can be bacteria selected from the genera *Acinetobacter, Acetobacter, Actinomyces, Aerococcus, Aeromonas, Agrobacterium, Anaplasma, Azorhizobium, Azotobacter, Bacillus, Bacteroides, Bartonella, Bordetella, Borrelia, Brucella, Burkholderia, Calymmatobacterium, Campylobacter, Chlamydia, Chlamydophila, Citrobacter, Clostridium, Corynebacterium, Coxiella, Ehrlichia, Enterobacter, Enterococcus, Escherichia, Francisella, Fusobacterium, Gardnerella, Haemophilus, Helicobacter, Klebsiella, Lactobacillus, Legionella, Listeria, Methanobacterium, Microbacterium, Micrococcus, Morganella, Moraxella, Mycobacterium, Mycoplasma, Neisseria, Pandoraea, Pasteurella, Peptostreptococcus, Porphyromonas, Prevotella, Proteus, Providencia, Pseudomonas, Ralstonia, Raoultella, Rhizobium, Rickettsia, Rochalimaea, Rothia, Salmonella, Serratia, Shewanella, Shigella, Spirillum, Staphylococcus, Strenotrophomonas, Streptococcus, Streptomyces, Treponema, Vibrio, Wolbachia, Yersinia*, or a combination thereof. In other embodiments, the infectious agent 102 can be one or more fungi selected from the genera *Candida* or *Cryptococcus* or mold.

Other specific bacteria that can be quantified using the methods and systems disclosed herein can comprise *Staphylococcus aureus, Staphylococcus lugdunensis*, coagulase-negative *Staphylococcus* species (including but not limited to *Staphylococcus epidermidis, Staphylococcus haemolyticus, Staphylococcus hominis, Staphylococcus capitis*, not differentiated), *Enterococcus faecalis, Enterococcus faecium* (including but not limited to *Enterococcus faecium* and other *Enterococcus* spp., not differentiated, excluding *Enterococcus faecalis*), *Streptococcus pneumoniae, Streptococcus pyogenes, Streptococcus agalactiae, Streptococcus* spp., (including but not limited to *Streptococcus mitis, Streptococcus pyogenes, Streptococcus gallolyticus, Streptococcus agalactiae, Streptococcus pneumoniae*, not differentiated), *Pseudomonas aeruginosa, Acinetobacter baumannii, Klebsiella* spp. (including but not limited to *Klebsiella pneumoniae, Klebsiella oxytoca*, not differentiated), *Escherichia coli, Enterobacter* spp. (including but not limited to *Enterobacter cloacae, Enterobacter aerogenes*, not differentiated), *Proteus* spp. (including but not limited to *Proteus mirabilis, Proteus vulgaris*, not differentiated), *Citrobacter* spp. (including but not limited to *Citrobacter freundii, Citrobacter koseri*, not differentiated), *Serratia marcescens, Candida albicans, Candida glabrata*, and *Candida tropicalis*.

Other more specific bacteria that can be quantified can comprise *Acinetobacter baumannii, Actinobacillus* spp., *Actinomycetes, Actinomyces* spp. (including but not limited to *Actinomyces israelii* and *Actinomyces naeslundii*), *Aeromonas* spp. (including but not limited to *Aeromonas hydrophila, Aeromonas veronii* biovar *sobria* (*Aeromonas sobria*), and *Aeromonas caviae*), *Anaplasma phagocytophilum, Alcaligenes xylosoxidans, Actinobacillus actinomycetemcomitans, Bacillus* spp. (including but not limited to *Bacillus anthracis, Bacillus cereus, Bacillus subtilis, Bacillus thuringiensis*, and *Bacillus stearothermophilus*), *Bacteroides* spp. (including but not limited to *Bacteroides fragilis*), *Bartonella* spp. (including but not limited to *Bartonella bacilliformis* and *Bartonella henselae*, *Bifidobacterium* spp., *Bordetella* spp. (including but not limited to *Bordetella pertussis, Bordetella parapertussis*, and *Bordetella bronchiseptica*), *Borrelia* spp. (including but not limited to *Borrelia recurrentis*, and *Borrelia burgdorferi*), *Brucella* sp. (including but not limited to *Brucella abortus, Brucella canis, Brucella melintensis* and *Brucella suis*), *Burkholderia* spp. (including but not limited to *Burkholderia pseudomallei* and *Burkholderia cepacia*), *Campylobacter* spp. (including but not limited to *Campylobacter jejuni, Campylobacter coli, Campylobacter lari* and *Campylobacter fetus*), *Capnocytophaga* spp., *Cardiobacterium hominis, Chlamydia trachomatis, Chlamydophila pneumoniae, Chlamydophila psittaci, Citrobacter* spp. *Coxiella burnetii, Corynebacterium* spp. (including but not limited to, *Corynebacterium diphtheriae, Corynebacterium jeikeum* and *Corynebacterium*),

*Clostridium* spp. (including but not limited to *Clostridium perfringens, Clostridium difficile, Clostridium botulinum* and *Clostridium tetani*), *Eikenella corrodens, Enterobacter* spp. (including but not limited to *Enterobacter aerogenes, Enterobacter agglomerans, Enterobacter cloacae* and *Escherichia coli*, including opportunistic *Escherichia coli*, including but not limited to enterotoxigenic *E. coli*, enteroinvasive *E. coli*, enteropathogenic *E. coli*, enterohemorrhagic *E. coli*, enteroaggregative *E. coli* and uropathogenic *E. coli*) *Enterococcus* spp. (including but not limited to *Enterococcus faecalis* and *Enterococcus faecium*) *Ehrlichia* spp. (including but not limited to *Ehrlichia chafeensia* and *Ehrlichia canis*), *Erysipelothrix rhusiopathiae, Eubacterium* spp., *Francisella tularensis, Fusobacterium nucleatum, Gardnerella vaginalis, Gemella morbillorum, Haemophilus* spp. (including but not limited to *Haemophilus influenzae, Haemophilus ducreyi, Haemophilus aegyptius, Haemophilus parainfluenzae, Haemophilus haemolyticus* and *Haemophilus parahaemolyticus, Helicobacter* spp. (including but not limited to *Helicobacter pylori, Helicobacter cinaedi* and *Helicobacter fennelliae*), Kingella *kingii, Klebsiella* spp. (including but not limited to *Klebsiella pneumoniae, Klebsiella granulomatis* and *Klebsiella oxytoca*), *Lactobacillus* spp., *Listeria monocytogenes, Leptospira interrogans, Legionella pneumophila, Leptospira interrogans, Peptostreptococcus* spp., *Moraxella catarrhalis, Morganella* spp., *Mobiluncus* spp., *Micrococcus* spp., *Mycobacterium* spp. (including but not limited to *Mycobacterium leprae, Mycobacterium tuberculosis, Mycobacterium intracellulare, Mycobacterium avium, Mycobacterium bovis*, and *Mycobacterium marinum*), *Mycoplasm* spp. (including but not limited to *Mycoplasma pneumoniae, Mycoplasma hominis*, and *Mycoplasma genitalium*), *Nocardia* spp. (including but not limited to *Nocardia asteroides, Nocardia cyriacigeorgica* and *Nocardia brasiliensis*), *Neisseria* spp. (including but not limited to *Neisseria gonorrhoeae* and *Neisseria meningitidis*), *Pasteurella multocida, Plesiomonas shigelloides. Prevotella* spp., *Porphyromonas* spp., *Prevotella melaninogenica, Proteus* spp. (including but not limited to *Proteus vulgaris* and *Proteus mirabilis*), *Providencia* spp. (including but not limited to *Providencia alcalifaciens, Providencia rettgeri* and *Providencia stuartii*), *Pseudomonas aeruginosa, Propionibacterium acnes, Rhodococcus equi, Rickettsia* spp. (including but not limited to *Rickettsia rickettsii, Rickettsia akari* and *Rickettsia prowazekii, Orientia tsutsugamushi* (formerly: *Rickettsia tsutsugamushi*) and *Rickettsia typhi*), *Rhodococcus* spp., *Serratia marcescens, Stenotrophomonas maltophilia, Salmonella* spp. (including but not limited to *Salmonella enterica, Salmonella typhi, Salmonella paratyphi, Salmonella enteritidis, Salmonella cholerasuis* and *Salmonella typhimurium*), *Serratia* spp. (including but not limited to *Serratia marcesans* and *Serratia liquifaciens*), *Shigella* spp. (including but not limited to *Shigella dysenteriae, Shigella flexneri, Shigella boydii* and *Shigella sonnei*), *Staphylococcus* spp. (including but not limited to *Staphylococcus aureus, Staphylococcus epidermidis, Staphylococcus hemolyticus, Staphylococcus saprophyticus*), *Streptococcus* spp. (including but not limited to *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae, Streptococcus mutans, Streptococcus pyogenes*, Group A streptococci, *Streptococcus pyogenes*, Group B streptococci, *Streptococcus agalactiae*, Group C streptococci, *Streptococcus anginosus, Streptococcus equismilis*, Group D streptococci, *Streptococcus bovis*, Group F streptococci, and *Streptococcus anginosus* Group G streptococci), *Spirillum minus, Streptobacillus moniliformi, Treponema* spp. (including but not limited to *Treponema carateum, Treponema petenue, Treponema pallidum* and *Treponema endemicum, Tropheryma whippelii, Ureaplasma urealyticum, Veillonella* sp., *Vibrio* spp. (including but not limited to *Vibrio cholerae, Vibrio parahemolyticus, Vibrio vulnificus, Vibrio parahaemolyticus, Vibrio vulnificus, Vibrio alginolyticus, Vibrio mimicus, Vibrio hollisae, Vibrio fluvialis, Vibrio metchnikovii, Vibrio damsela* and *Vibrio furnisii*), *Yersinia* spp. (including but not limited to *Yersinia enterocolitica, Yersinia pestis*, and *Yersinia pseudotuberculosis*) and *Xanthomonas maltophilia* among others.

Furthermore, other infectious agents 102 that can be quantified can comprise fungi or mold including, but not limited to, *Candida* spp. (including but not limited to *Candida albicans, Candida glabrata, Candida tropicalis, Candida parapsilosis*, and *Candida krusei*), *Aspergillus* spp. (including but not limited to *Aspergillus fumigatous, Aspergillus flavus, Aspergillus clavatus*), *Cryptococcous* spp. (including but not limited to *Cryptococcus neoformans, Cryptococcus gattii, Cryptococcus laurentii*, and *Cryptococcus albidus*), *Fusarium* spp. (including but not limited to *Fusarium oxysporum, Fusarium solani, Fusarium verticillioides*, and *Fusarium proliferatum*), *Rhizopus oryzae, Penicillium marneffei, Coccidiodes immitis*, and *Blastomyces dermatitidis*.

The fluid delivery conduits 108 can include tubes, pumps, containers, or microfluidic channels for delivering buffers, reagents, fluid samples including the target sample 104, or a combination thereof to and between devices, apparatus, or containers in the system. For example, as shown in FIG. 1, the fluid delivery conduits 108 can refer to parts of a pump such as a syringe pump. In other embodiments, the fluid delivery conduits 108 can include or refer to at least part of a hydraulic pump, a pneumatic pump, a peristaltic pump, a vacuum pump or a positive pressure pump, a manual or mechanical pump, or a combination thereof. In additional embodiments, the fluid delivery conduits 108 can include or refer to at least part of an injection cartridge, a pipette, a capillary, a dispenser bottle, or a combination thereof. The fluid delivery conduits 108 can also be part of a vacuum system configured to draw fluid to or through channels, tubes, or passageways under vacuum. Moreover, the fluid delivery conduits 108 can include or refer to at least part of a multichannel delivery system or pipette.

The method 100 can further comprise diluting aliquots of the target sample 104 in step 1B. For example, step 1B can comprise diluting a first aliquot of the target sample 104 by a first dilution factor ($DF_1$) to yield a first diluted sample 110A. Step 1B can also comprise diluting a second aliquot of the target sample 104 by a second dilution factor ($DF_2$) to yield a second diluted sample 110B. The second diluted sample 110B can also be obtained by serially or subsequently diluting a previously diluted sample. The first aliquot and the second aliquot can be diluted using a dilutive solution 112.

In some embodiments, the dilutive solution 112 can comprise growth media or a growth inducer. In these and other embodiments, the dilutive solution 112 can be a solution containing bacto-tryptone, tryptic soy digest, yeast extract, beef extract, cation-adjusted Mueller Hinton Broth (CAMHB), glucose supplemented Mueller Hinton broth (MHG), starch, acid hydrolysate of casein, calcium chloride, magnesium chloride, sodium chloride, blood or lysed blood including lysed horse blood (LHB), CAMHB-LHB, glucose or other carbohydrates, or a combination thereof. The growth inducer can comprise a carbon-based inducer, a nitrogen-based inducer, a mineral, a trace element, a biological growth factor, or any combination thereof. For example, the growth inducer can include but is not limited to a carbohydrate such as glucose or starches, ammonia, magnesium, amino acids, casamino acids, vitamins, peptides, blood, or a combination thereof. In one example embodiment, the dilutive solution 112 can comprise tryptone, yeast extract, sodium chloride, starch, and glucose.

In some embodiments, any one of $DF_1$ and $DF_2$ can be between about 1:1 to about 1:10. In these and other embodiments, any one of $DF_1$ and $DF_2$ can also be between about 1:10 to about 1:100. In these and other embodiments, any one of $DF_1$ and $DF_2$ can also be between about 1:100 to about $1:10^3$. In these and other embodiments, any one of $DF_1$ and $DF_2$ can also be between about $1:10^3$ to about $1:10^7$. In these and other embodiments, any one of $DF_1$ and $DF_2$ can also be greater than $1:10^7$. For example, the first aliquot of the target sample 104 can be diluted with the dilutive solution 112 by a dilution factor of 1:10 to yield the first diluted sample 110A and the second aliquot of the target sample 104 can be diluted with the dilutive solution 112 by a dilution factor of 1:100 to yield the second diluted sample 110B.

Although FIG. 1 illustrates two aliquots of the target sample 104 being diluted in step 1B, it is contemplated by this disclosure that additional aliquots of the target sample 104 can be diluted to different dilution ratios to yield additional diluted samples (e.g., a third diluted sample, a fourth diluted sample, etc.). The additional diluted samples can be used to generate additional corrected calibration curve equation parameters to improve the accuracy of the method. For example, the additional diluted samples can be used to generate additional corrected calibration curve slopes (i.e., additional $m_{corr}$ values) that can be averaged to yield a more accurate corrected calibration curve slope. As another example, the additional diluted samples can be used to identify outliers and therefore enable a more careful selection of which $m_{corr}$ values to use for the corrected calibration curve slope.

The method 100 can further comprise introducing the diluted samples to sensors 116 or exposing the sensors 116 to the diluted samples such that the diluted samples are in fluid communication with a redox-active material 708 (see FIGS. 7A and 7B) or a functionalization layer 806 (see FIGS. 8A and 8B) of the sensors 116 in step 1C. For example, the first diluted sample 110A can be introduced to a first sensor (one of the sensors 116) and the second diluted sample 110B can be introduced to a second sensor (another one of the sensors 116). The sensors 116 can be configured to respond to a change in a solution characteristic of the diluted samples. In some embodiments, the sensors 116 can be oxidation reduction potential (ORP) sensors configured to respond to a change in the ORP of the diluted samples. In other embodiments, the sensors 116 can be pH sensors configured to respond to a change in the pH of the diluted samples.

The method 100 can also comprise incubating the diluted samples at an elevated temperature for a period of time in step 1D. The diluted samples can be incubated in the same reaction vessels 106 or transferred to different reaction vessels 106 or containers. For example, the first diluted sample 110A and the second diluted sample 110B can be heated to a temperature of between about 30° C. and about 40° C. (e.g., 35° C.±2° C.) and allowed to incubate for an incubation period 114. The incubation period 114 can range from 15 minutes to over one hour. In other embodiments, the incubation period 114 can be less than 15 minutes or up to 48 hours. The diluted samples can be incubated while exposed to or otherwise in fluid communication with at least part of the sensors 116.

In the example embodiment shown in FIG. 1, exposing a sensor 116 to a diluted sample (any of the first diluted sample 110A or the second diluted sample 110B) can involve directly immersing at least part of a handheld or probe instance of the sensor 116 into the diluted sample. In this embodiment, the handheld or probe instance of the sensor 116 can be a handheld OPR sensor or a handheld pH sensor coupled to a standalone parameter analyzer 118, such as a voltmeter or multimeter. In another example embodiment shown in FIG. 6, introducing the diluted sample to the sensor 116 can involve injecting, delivering, or otherwise introducing the diluted sample to a well or container comprising the sensor 116 fabricated on a substrate. The sensors 116 will be discussed in more detail in the following sections.

The method 100 can further comprise monitoring the solution characteristics of the diluted samples with one or more computing devices 120 coupled to the parameter analyzers 118 or coupled directly to the sensors 116. The solution characteristics of the diluted samples can be monitored in the absence of any exogenous reporter molecules added to the diluted samples.

Although FIG. 1 shows the parameter analyzers 118 as separate standalone devices from the computing device 120, it is contemplated by this disclosure and it should be understood by one of ordinary skill in the art that the parameter analyzer 118 and the computing device 120 can be integrated into one device. As illustrated in FIG. 1, computing device 120 can be a mobile device, a handheld device, a tablet device, a laptop or desktop computer. In some embodiments, the parameter analyzers 118 can wirelessly communicate a signal or result to computing device 120.

The solution characteristics of the diluted samples can change as the amount of electro-active redox species or the amount of ions change due to the energy use, oxygen uptake or release, growth, or metabolism of the infectious agents 102 in the diluted samples. For example, the amount of electro-active redox species in the diluted samples can change as a result of cellular activity (e.g., microbial aerobic or anaerobic respiration) undertaken by the infectious agents 102 in the diluted samples. Also, as an example, the amount of $H^+$ ions in the diluted samples can change as a result of cellular activity undertaken by the infectious agents 102 in the diluted samples.

As a more specific example, the amount of electron donors from Table 1 below (e.g., the amount of energy carriers such as nicotinamide adenine dinucleotide (NADH) and flavin adenine dinucleotide ($FADH_2$)) in the diluted samples can change due to the growth of the infectious agents 102 in the diluted samples. Also, as another more specific example, the amount of oxygen depleted in the diluted samples due to aerobic respiration can change due to the growth of the infectious agents 102 in the diluted samples.

calibration curves 204 and calculating the $m_{avg}$ and the $b_{avg}$ will be discussed in the following sections with respect to FIG. 2. In some embodiments, the infectious agents 202 used to generate the multiple calibration curves 204 can be the same species as the infectious agent 102 of the unknown strain in the target sample 104. In other embodiments, at

TABLE 1

Below is a "redox tower" visualizing potential electron donors and acceptors which can be utilized by infectious agents during the course of metabolism. An electron donor will have a greater negative potential than the electron acceptor. In aerobic respiration for example, $O_2$ can serve as a terminal electron acceptor whereas in anaerobic respiration, the terminal electron acceptor can comprise $NO_3^-$, $Fe^{3+}$, $Mn^{4+}$, $SO_4^{2-}$, or $CO_2$.

| Electron Donor and Acceptor Pairs | Measured Standard Reduction Potential $E'_0$ (mV) | Standard Reduction Potential $E'_0$ (mV) range |
|---|---|---|
| Glucose ⇌ 2 Pyruvate + 2e⁻ | −720 | −700 |
|  |  | −600 |
| Glucose ⇌ 6 $CO_2$ + 24e⁻ | −500 | −500 |
| $H_2$ ⇌ 2$H^+$ + 2e⁻ | −420 | −400 |
| NADH ⇌ $NAD^+$ + 2e⁻ | −320 | −300 |
| 2 GSH ⇌ GSSG + 2e⁻ | −240 | −200 |
| $H_2S$ ⇌ $SO_4^{2-}$ + 8e⁻ | −220 |  |
| $FADH_2$ ⇌ FAD + 2$H^+$ + 2e⁻ | −220 |  |
| Lactate ⇌ Pyruvate + 2e⁻ | −190 | −100 |
| Succinate ⇌ Fumarate + 2e⁻ | 33 | 0 |
| Cyt b (red) ⇌ Cyt b (ox) + e⁻ | 80 |  |
| Ubiquinol ⇌ Ubiquinone + 2e⁻ | 110 | 100 |
| Cyt c (red) ⇌ Cyt c (ox) + e⁻ | 250 | 200 |
| Cyt a (red) ⇌ Cyt a (ox) + e⁻ | 290 |  |
|  |  | 300 |
| $NO_2^-$ + $H_2O$ ⇌ $NO_3^-$ + 2e⁻ | 420 | 400 |
| $NH_4^+$ + $H_2O$ ⇌ $NO_2^-$ + 6e⁻ | 440 |  |
| $Mn^{2+}$ + $H_2O$ ⇌ $MnO_2$ + 2e⁻ | 460 |  |
|  |  | 500 |
|  |  | 600 |
| ½ $N_2$ + 3$H_2O$ ⇌ $NO_3^-$ + 5e⁻ | 740 | 700 |
| $Fe^{2+}$ ⇌ $Fe^{3+}$ + 1e⁻ | 770 |  |
| $H_2O$ ⇌ ½ $O_2$ + 2$H^+$ + 2e⁻ | 820 | 800 |
|  |  | 700 |

The method 100 can further comprise determining a first time-to-detection ($TTD_1$) representing the time it takes a solution characteristic of the first diluted sample 110A to undertake a predetermined threshold change 122 in step 1E. In addition, step 1E can also comprise determining a second time-to-detection ($TTD_2$) representing the time it takes a solution characteristic of the second diluted sample 110B to undertake the same predetermined threshold change 122. For example, when the solution characteristic is ORP, the predetermined threshold change 122 can be between about Δ100 mV and Δ700 mV. As a more specific example, a predetermined ORP threshold level ($V_{th}$) can be set at −100 mV and the time-to-detection can represent the time it takes the ORP of a diluted sample to reach −100 mV from 0 mV. As an additional example, when the solution characteristic is pH, the predetermined threshold change 122 can be between about ΔpH 0.01 and ΔpH 3.0. As a more specific example, a predetermined pH threshold level ($pH_{th}$) can be set at pH 6.7 and the time-to-detection can represent the time it takes the pH of a diluted sample to reach pH 6.7 from a normalized pH of 7.0 (ΔpH −0.3).

The method 100 can further comprise calculating an average calibration curve slope ($m_{avg}$) and an average calibration curve y-intercept ($b_{avg}$) from equation parameters obtained from multiple calibration curves 204 representing growth behavior of infectious agents 202 of different known strains. An example method 200 of generating the multiple least one of the infectious agents 202 used to generate the multiple calibration curves 204 can be of a different species from the infectious agent 102 of the unknown strain in the target sample 104. As will be discussed in the following sections, generating the multiple calibration curves 204 and calculating the $m_{avg}$ and the $b_{avg}$ can be done at any point prior to step 1G. For example, generating the multiple calibration curves 204 and calculating the $m_{avg}$ and the $b_{avg}$ can be done contemporaneously with any of steps 1A, 1B, 1C, 1D, 1E, or 1F of method 100. Alternatively, generating the multiple calibration curves 204 and calculating the $m_{avg}$ and the $b_{avg}$ can be done prior to step 1A and the multiple calibration curves 204, the $m_{avg}$, and the $b_{avg}$ can be stored in a memory of computing device 120 or a database accessible to the computing device 120.

The method 100 can also comprise calculating a corrected calibration curve slope ($m_{corr}$) using at least the $TTD_2$, the $TTD_1$, the $DF_2$, and the $DF_1$ in step 1F. As will be discussed in more detail in the following sections, $m_{corr}$ can be calculated using Equation 1 below:

$$m_{corr} = \frac{-(TTD2 - TTD1)}{\log_a\left(\frac{DF_2}{DF_1}\right)} \quad \text{Equation 1}$$

The method 100 can further comprise calculating a corrected calibration curve y-intercept ($b_{corr}$) using at least the $b_{avg}$, the $m_{corr}$, and the $m_{avg}$ in step 1G. As will be discussed in more detail in the following sections, $m_{corr}$ can be calculated using Equation 2 below:

$$b_{corr} = \frac{m_{corr}}{a_{avg}} \times b_{avg} \qquad \text{Equation 2}$$

The method 100 can further comprise determining the concentration of the infectious agent 102 of the unknown strain in the target sample 104 (hereinafter, $Conc_{target}$) using at least the $m_{corr}$, the $b_{corr}$, and either the $TTD_1$ and the $DF_1$ or the $TTD_2$ and the $DF_2$. As will be discussed in more detail in the following sections, $Conc_{target}$ can be calculated using either Equation 3 or Equation 4 below:

$$Conc_{target} = DF_1 \times a^{\left(\frac{TTD_1 - b_{corr}}{m_{corr}}\right)} \qquad \text{Equation 3}$$

$$Conc_{target} = DF_2 \times a^{\left(\frac{TTD_2 - b_{corr}}{m_{corr}}\right)} \qquad \text{Equation 4}$$

In Equations 3 and 4 above, the variable "a" can be any positive real number other than 1. Using the method 100 described herein, a laboratory or hospital can determine the concentration of the infectious agent 102 in a target sample 104 between about 60 minutes and 120 minutes. In other embodiments, the concentration of the infectious agent 102 can be determined between about 5 minutes and 60 minutes.

In some embodiments, one or more of the aforementioned steps of the method 100 can be stored as machine-executable instructions or logical commands in a non-transitory machine-readable medium (e.g., a memory or storage unit) of the computing device 120 or another device communicatively or electrically coupled to the computing device 120. Any of the parameter analyzer 118, the computing device 120, or another device coupled to the parameter analyzer 118 or the computing device 120 can comprise one or more processors or controllers configured to execute the aforementioned instructions or logical commands.

The steps depicted in FIG. 1 do not require the particular order shown to achieve the desired result. Moreover, certain steps or processes may be omitted or occur in parallel in order to achieve the desired result. In addition, any of the systems or devices disclosed herein can be used in lieu of devices or systems shown in the steps of FIG. 1.

Figure 2:
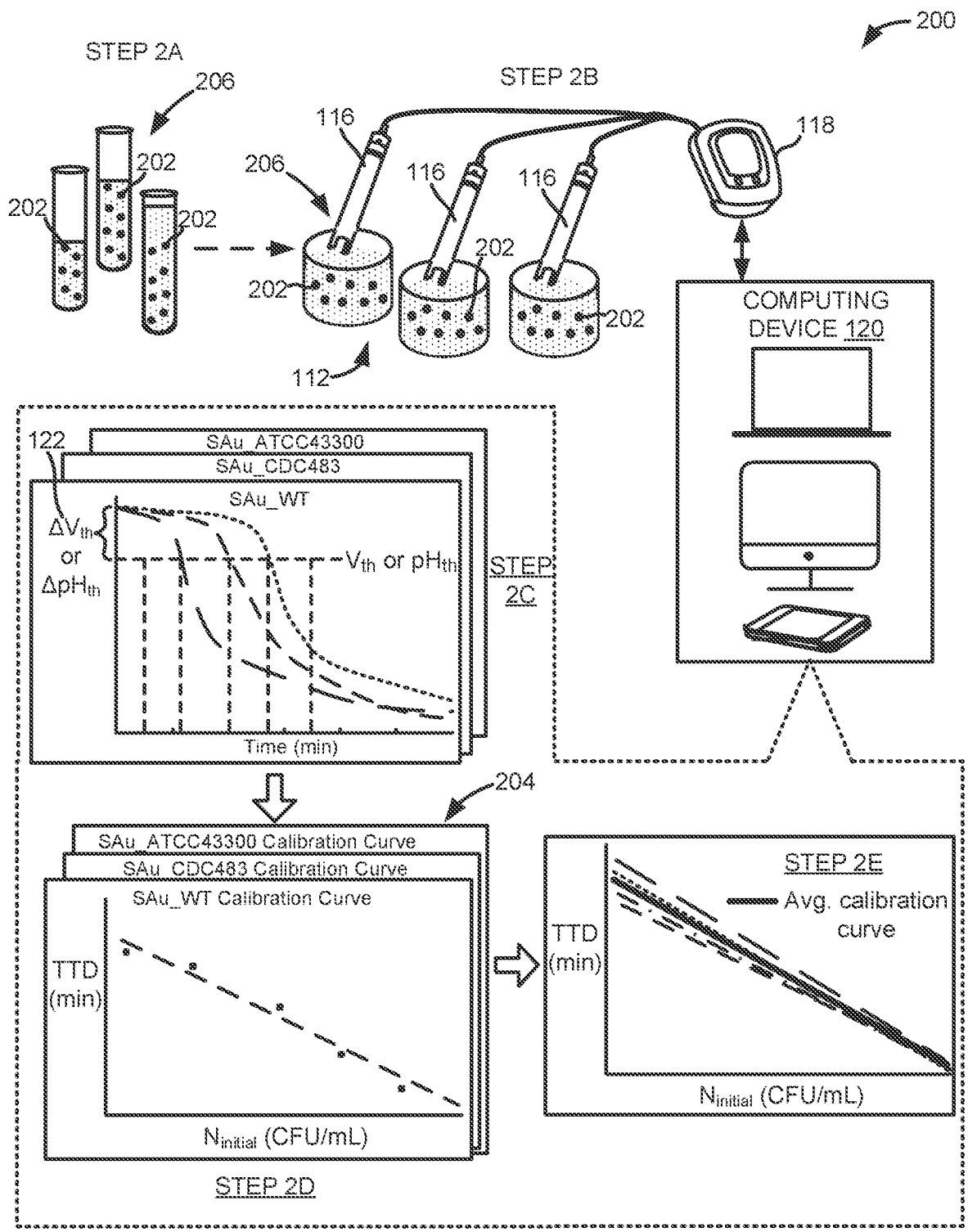
FIG. 2 illustrates additional steps of the example method for determining the concentration of an infectious agent in a target sample.

FIG. 2 illustrates an example method 200 for generating the multiple calibration curves 204 and calculating the $m_{avg}$ and the $b_{avg}$ from equation parameters obtained from the multiple calibration curves 204. As previously discussed, the infectious agents 202 used to generate the multiple calibration curves 204 can be the same species as the infectious agent 102 in the target sample 104. In other embodiments, at least one of the infectious agents 202 used to generate the multiple calibration curves 204 can be of a different species from the infectious agent 102 in the target sample 104.

The method 200 can comprise preparing cultures 206 comprising infectious agents 202 of different known strains in step 2A. For example, the infectious agent 102 in the target sample 104 can be determined to be of the species *Staphylococcus Aureus* (SAu). In this example embodiment, the infectious agents 202 used to prepare the multiple calibration curves 204 can be different known strains of SAu such as wild-type strain SAu (SAu_WT), CDC483 strain SAu (SAu_CDC483), ATCC43300 strain SAu (SAu_ATCC43300), and CDC475 strain SAu (SAu_CDC475). The prepared cultures 206 can comprise different initial concentrations ($N_{initial}$) of an infectious agent 202 of a particular known strain. For example, step 2A can comprise preparing cultures of SAu_WT at initial concentrations of $1 \times 10^4$ CFU/mL, $1 \times 10^5$ CFU/mL, $1 \times 10^6$ CFU/mL, $1 \times 10^7$ CFU/mL, and $1 \times 10^8$ CFU/mL. A dilutive solution (such as the dilutive solution 112) can be used to dilute an initial prepared culture 206 of an infectious agent 202 to obtain additional cultures with different starting concentrations. For example, the prepared cultures can be infectious agent liquid cultures prepared by re-suspending infectious agent colonies from an infectious agent culture plate into growth media to reach the aforementioned concentrations by measuring the optical density (O.D.) of the solution (e.g., O.D. measured at a wavelength of 600 nm). As a more specific example, the prepared cultures can be liquid bacterial cultures prepared by inoculating bacterial colonies from a bacterial culture plate into growth media to reach the aforementioned concentrations measured by O.D.

The method 200 can also comprise introducing the prepared cultures 206 to sensors 116 or exposing the sensors 116 to the prepared cultures 206 such that the prepared cultures 206 are in fluid communication with a redox-active material 708 (see FIGS. 7A and 7B) or a functionalization layer 806 (see FIGS. 8A and 8B) of the sensors 116 in step 2B. The sensors 116 can be configured to respond to a change in a solution characteristic of the prepared cultures 206 over time. In some embodiments, the sensors 116 can be oxidation reduction potential (ORP) sensors configured to respond to a change in the ORP of the prepared cultures 206. In other embodiments, the sensors 116 can be pH sensors configured to respond to a change in the pH of the prepared cultures 206. The method 200 can further comprise monitoring the solution characteristics of the prepared cultures 206 with one or more computing devices 120 coupled to the parameter analyzers 118 or coupled directly to the sensors 116. The solution characteristics of the prepared cultures 206 can be monitored in the absence of any exogenous reporter molecules added to the prepared cultures 206.

The method 200 can further comprise determining a calibration time-to-detection ($TTD_{calibration}$) of each of the prepared cultures 206 representing the time it takes the solution characteristic of each of the prepared cultures 206 to undertake a predetermined threshold change 122 in step 2C. For example, when the solution characteristic is ORP, the predetermined threshold change 122 can be between about Δ100 mV and Δ700 mV. As a more specific example, a predetermined ORP threshold level ($V_{th}$) can be set at −100 mV and the $TTD_{calibration}$ can represent the time it takes the ORP of a prepared culture 206 to reach −100 mV from 0 mV. As an additional example, when the solution characteristic is pH, the predetermined threshold change 122 can be between about ΔpH 0.01 and ΔpH 3.0. As a more specific example, a predetermined pH threshold level ($pH_{th}$) can be set at pH 6.7 and the $TTD_{calibration}$ can represent the time it takes the pH of a prepared culture 206 to reach pH 6.7 from a normalized pH of 7.0 (ΔpH −0.3). In all such embodiments, the same predetermined threshold change 122 used with respect to step 2C is also used with respect to step 1E of FIG. 1.

The method 200 can further comprise plotting $TTD_{calibration}$ data against $N_{initial}$ data for each of the prepared cultures 206 of a particular known strain in step 2D. For example, $TTD_{calibration}$ data for SAu_WT can be plotted against $N_{initial}$ data for SAu_WT. Step 2D can also comprise fitting a calibration curve 204 to $TTD_{calibration}$ data and $N_{initial}$ data using a curve-fitting technique. In some embodiments, the curve-fitting technique can be least-squares curve-fitting technique or algorithm. In other embodiments, the curve-fitting technique can be a logarithmic regression curve-fitting technique. In other embodiments, a polynomial curve fitting technique can also be used.

For example, a calibration curve 204 can be fitted to the $TTD_{calibration}$ data and $N_{initial}$ data for a particular known strain using Equation 5 below:

$$TTD_{calibration} = m_{strain\_specific} \times \log_a(N_{initial}) + b_{strain\_specific} \quad \text{Equation 5:}$$

In Equation 5 above, the variable "a" can be any positive real number other than 1. In addition, in Equation 5 above, the curve fitting parameters $m_{strain\_specific}$ and $b_{strain\_specific}$ can refer to a strain-specific calibration curve slope and a strain-specific calibration curve y-intercept, respectively. The same process can be repeated for other known strains of an infectious agent 202. For example, the same process can be repeated for multiple strains of SAu such as SAu_WT, SAu_CDC483, SAu_ATCC43300, and SAu_CDC475 such that unique pairs of $m_{strain\_specific}$ and $b_{strain\_specific}$ are calculated for each of SAu_WT, SAu_CDC483, SAu_ATCC43300, and SAu_CDC475.

In addition to calculating curve fitting parameters $m_{strain\_specific}$ and $b_{strain\_specific}$ for known strains of the same species, steps 2A, 2B, 2C, and 2D can also be undertaken to calculate $m_{strain\_specific}$ and $b_{strain\_specific}$ for known strains of infectious agents 202 of different species. For example, as will be discussed in more detail in the following sections, unique pairs of $m_{strain\_specific}$ and $b_{strain\_specific}$ can also be calculated for different known strains of *Escherichia Coli* (Eco), *Enterobacter Cloacae* (ECl), *Enterobacter Aerogenes* (EAe), and *Klebsiella Pneumoniae* (KPn).

The method 200 can also comprise calculating an average calibration curve slope ($m_{avg}$) in step 2E by taking an average of the multiple $m_{strain\_specific}$ values calculated from step 2D. Step 2E can also comprise calculating an average calibration curve y-intercept ($b_{avg}$) by taking an average of the multiple $b_{strain\_specific}$ values calculated from step 2D. In some embodiments, all of the $m_{strain\_specific}$ values used to calculate the $m_{avg}$ and all of the $b_{strain\_specific}$ values used to calculate the $b_{avg}$ can be obtained from calibration curves 204 fitted to data obtained from multiple strains of the same species of infectious agent 202. For example, the $m_{avg}$ and the $b_{avg}$ can be calculated from $m_{strain\_specific}$ values and $b_{strain\_specific}$ values calculated for SAu_WT, SAu_CDC483, SAu_ATCC43300, and SAu_CDC475.

In other embodiments, the $m_{strain\_specific}$ values used to calculate the $m_{avg}$ and the $b_{strain\_specific}$ values used to calculate the $b_{avg}$ can be obtained from calibration curves 204 fitted to data obtained from infectious agents 202 of different species. For example, the $m_{avg}$ and the $b_{avg}$ can be calculated from $m_{strain\_specific}$ values and $b_{strain\_specific}$ values calculated for SAu_WT, wild-type strain ECo (ECo_WT), wild-type strain EAe (EAe_WT), wild-type strain KPn (KPn_WT), and CDCl$_8$ strain ECl (ECl_CDC 8). Also, as additional examples, the $m_{avg}$ and the $b_{avg}$ can be calculated from $m_{strain\_specific}$ values and $b_{strain\_specific}$ values calculated for infectious agents 202 of the same family or the same genus.

Although method 200 is shown separate from method 100, it is contemplated by this disclosure and it should be understood by one of ordinary skill in the art that method 200 can be considered sub-steps or pre-steps of method 100. Moreover, the steps depicted in FIG. 2 do not require the particular order shown to achieve the desired result. Moreover, certain steps or processes may be omitted or occur in parallel in order to achieve the desired result. In addition, any of the systems or devices disclosed herein can be used in lieu of devices or systems shown in the steps of FIG. 2.

Figure 3A:
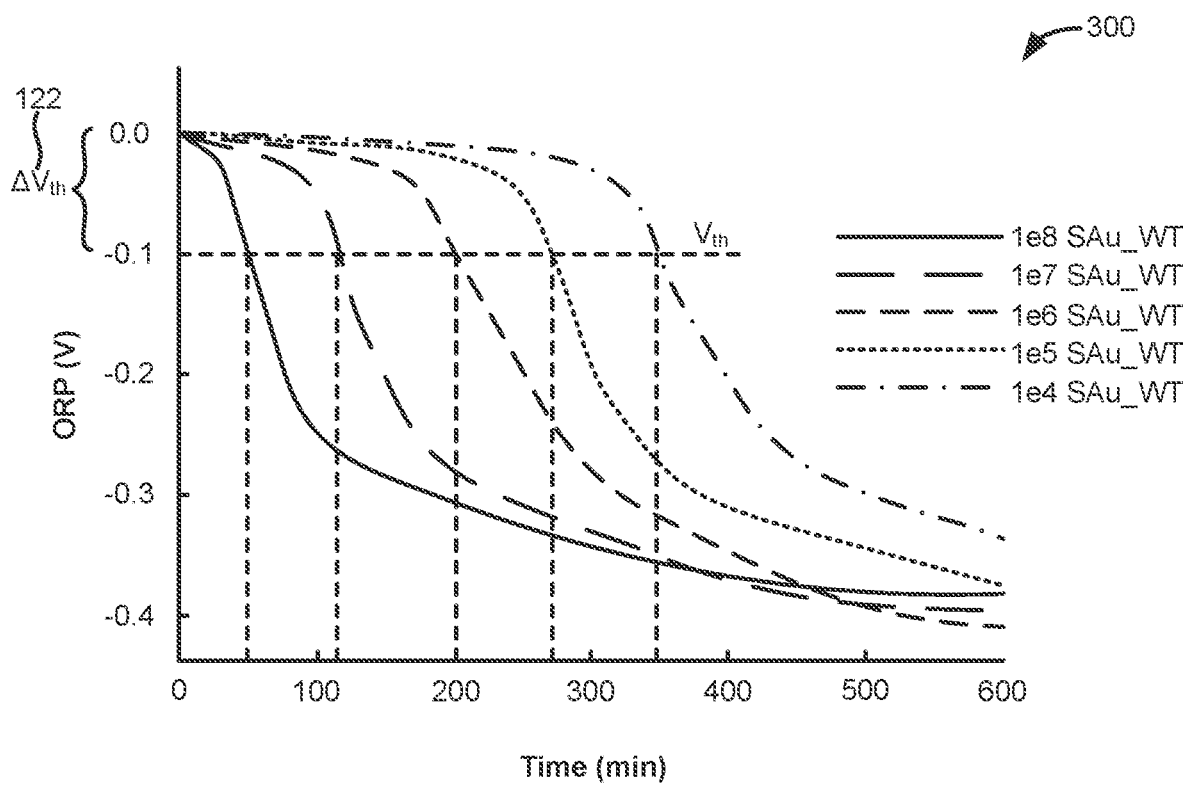
FIG. 3A illustrates growth curves of cultures of infectious agents of a particular strain at different starting concentrations.

FIGS. 3A to 3E illustrate an example application of the methods described herein for determining the concentration of an unknown strain of SAu in a target sample 104. FIG. 3A illustrates multiple growth curves 300 representing a change in the solution characteristic of prepared cultures 206 of a known strain of SAu (in this case, wild-type SAu). The growth curves 300 can be recorded by monitoring the sensor output of one or more ORP sensors (including, but not limited to, the sensors 116) in fluid communication with the prepared cultures 206. The prepared cultures 206 can comprise different initial concentrations ($N_{initial}$) of SAu_WT (e.g., $1 \times 10^4$ CFU/mL, $1 \times 10^5$ CFU/mL, $1 \times 10^6$ CFU/mL, $1 \times 10^7$ CFU/mL, and $1 \times 10^8$ CFU/mL of SAu_WT).

Figure 7A:
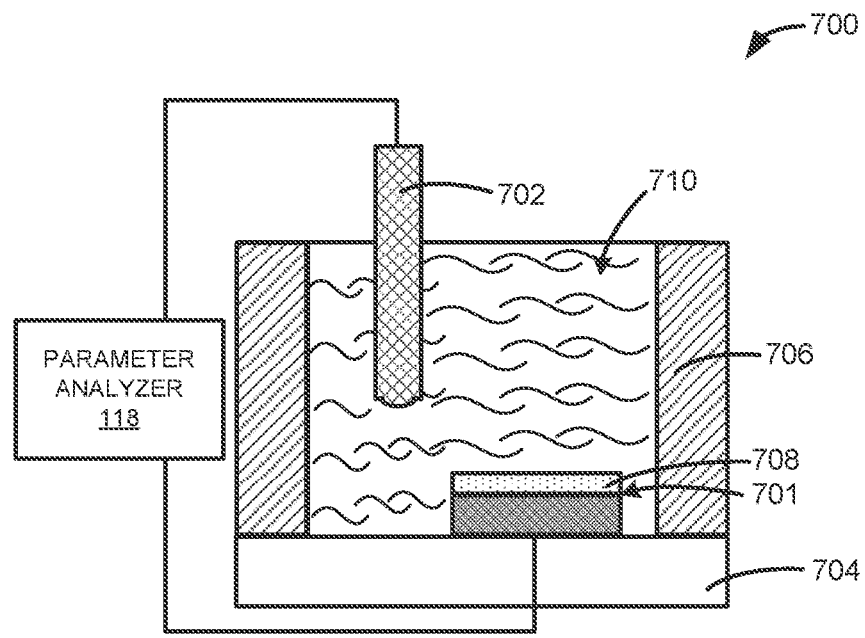
FIG. 7A illustrates a schematic of one embodiment of an ORP sensor used as part of the methods and systems described herein.
Figure 7B:
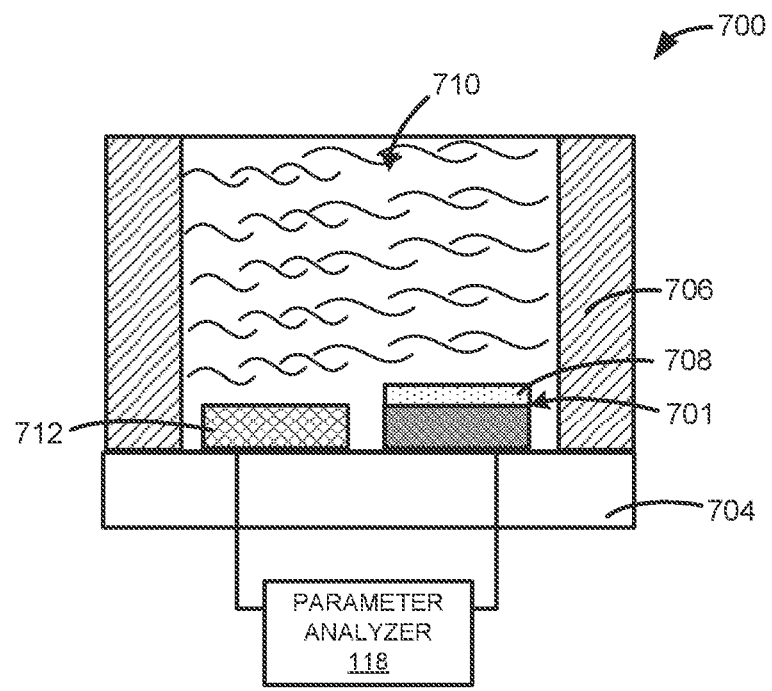
FIG. 7B illustrates a schematic of another embodiment of the ORP sensor used as part of the methods and systems described herein.

The sensor output (voltage output in this case) can be a potential difference between an active electrode and a reference electrode such as the external reference electrode or the on-chip reference electrode (see FIGS. 7A and 7B). The voltage output of the one or more ORP sensors can change as the ORP of each of the prepared cultures 206 changes over time.

The voltage output can decrease as the solution characteristic of the prepared cultures 206 change due to the energy use, oxygen uptake or release, growth, or metabolism of the infectious agents 202 in solution. In some embodiments, the growth curve can follow a sigmoidal pattern or shape, a step function or shape, or other patterns or shapes. Over longer time scales, the growth curve can begin to increase or become more positive.

For example, the voltage output of the ORP sensor can decrease to a negative potential over time as the solution characteristic of each of the prepared cultures 206 changes as a result of cellular activity undertaken by the infectious agents 202 in solution. As a more specific example, the solution characteristic of the prepared cultures 206 can change as the amount of energy carriers (such as nicotinamide adenine dinucleotide (NADH) and flavin adenine dinucleotide ($FADH_2$)) in the sampled solution changes due to the growth of the infectious agents 202. Also, as another more specific example, the amount of oxygen depleted in the prepared cultures 206 can change due to the growth of the infectious agents 202 (e.g., SAu_WT) in solution.

Although outputs for ORP sensors are shown in FIGS. 3A-3E, it is contemplated by this disclosure that pH sensors can also be used in lieu of or in combination with ORP sensors. The pH sensors can be configured to respond to a change in the pH of the prepared cultures 206.

FIG. 3A also illustrates that a calibration time-to-detection ($TTD_{calibration}$) can also be recorded for each of the prepared cultures 206. The $TTD_{calibration}$ represents the time it takes the solution characteristic of each of the prepared cultures 206 to undertake a predetermined threshold change 122. For example, as shown in FIG. 3A, the time it takes the ORP of each of the prepared cultures 206 of SAu_WT to reach a predetermined threshold voltage of −100 mV (from a starting voltage of 0 V) can be recorded by the parameter analyzer 118, the computing device 120, or a combination thereof.

Figure 3B:
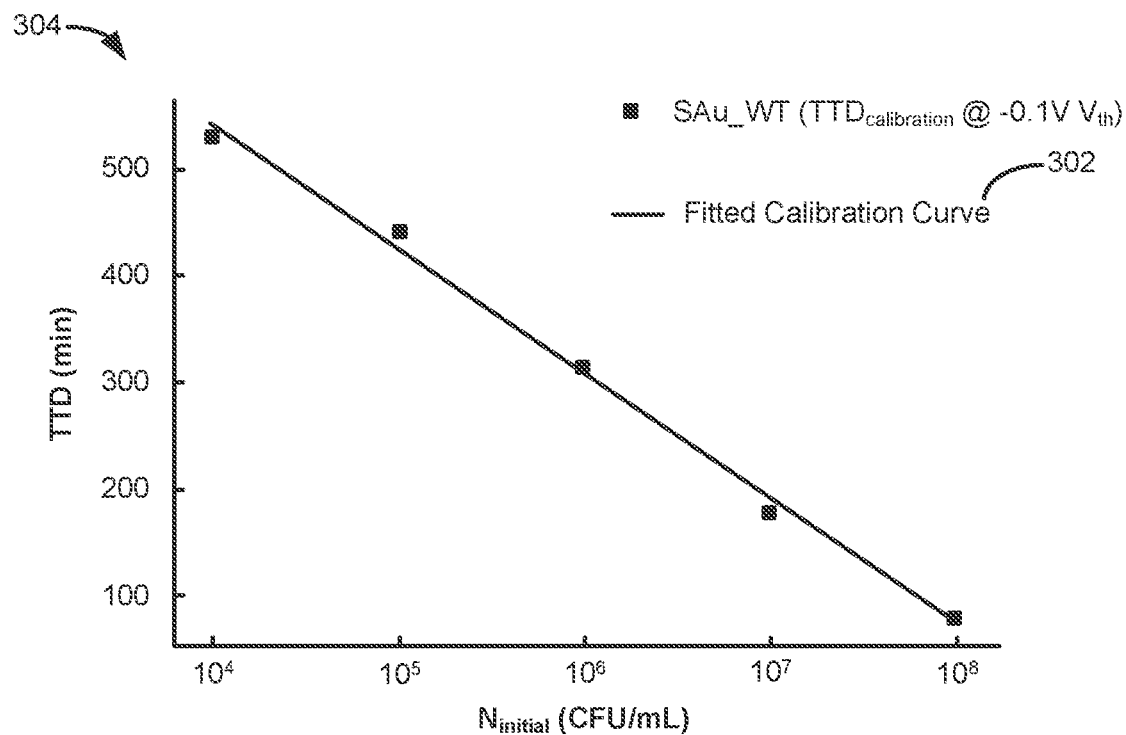
FIG. 3B illustrates a strain-specific calibration curve fitted to data obtained from the strain-specific growth curves.

FIG. 3B illustrates a strain-specific calibration curve 302 (in this case, the SAu_WT calibration curve) fitted to $TTD_{calibration}$ and $N_{initial}$ data obtained from the strain-specific growth curves 300 of FIG. 3A. For example, $TTD_{calibration}$ data and $N_{initial}$ data can be plotted on a semi-log plot (or linear-logarithmic plot) 304 as shown in FIG. 3B. The strain-specific calibration curve 302 can be fitted to the $TTD_{calibration}$ and $N_{initial}$ data using curve-fitting techniques. In one embodiment, the curve-fitting technique can be a least-squares curve fitting technique. In other embodiments, the curve-fitting technique can be a logarithmic regression or polynomial curve-fitting technique. The strain-specific calibration curve 302 can refer to one of the multiple calibration curves 204 discussed with respect to FIG. 2.

In one embodiment, the strain-specific calibration curve 302 for SAu_WT can be fitted to the $TTD_{calibration}$ and $N_{initial}$ data using Equation 5 above. In this and other embodiments (i.e., the prepared cultures 206 are cultures of SAu_WT), the curve fitting parameters $m_{strain\_specific}$ and $b_{strain\_specific}$ can refer to a SAu_WT calibration curve slope and a SAu_WT calibration curve y-intercept, respectively.

The same process can be repeated for other known strains of an infectious agent 202 of a particular species. For example, the same process can be repeated for other known strains of SAu such as SAu_CDC483, SAu_ATCC43300, and SAu_CDC475 such that unique pairs of $m_{strain\_specific}$ and $b_{strain\_specific}$ are calculated for each of SAu_WT, SAu_CDC483, SAu_ATCC43300, and SAu_CDC475.

Table 2 below shows calibration curve slopes and calibration curve y-intercepts calculated for different strains of SAu including SAu_WT, SAu_CDC483, SAu_ATCC43300, and SAu_CDC475. Table 2 also shows that an average calibration curve slope ($m_{avg}$) can be calculated by taking an average of the various SAu calibration curve slopes. In addition, Table 2 also shows that an average calibration curve y-intercept ($b_{avg}$) can be calculated by taking an average of the various SAu calibration curve y-intercepts.

TABLE 2

| SAu Calibration Curve Parameters | | |
|---|---|---|
| SAu Strain | Calibration Curve Slope (m) | Calibration Curve y-intercept (b) |
| Wild-type (WT) | −75.3 | 649.4 |
| CDC 483 | −67.9 | 587.3 |
| ATCC 43300 | −76.8 | 649.1 |
| CDC 475 | −72.2 | 615.1 |
| SAu Reference Calibration Curve | $M_{avg}$ = −73.0 | $b_{avg}$ = 625.2 |

The various SAu calibration curve slopes and y-intercepts along with the $m_{avg}$ and the $b_{avg}$ values can be stored in a database on a memory device of the computing device 120 or stored in another database accessible to the computing device 120. Such stored values can be used to quantify a target sample 104 that immediately tests positive for SAu but where the particular strain or growth characteristic of SAu is initially unknown.

Figure 3C:
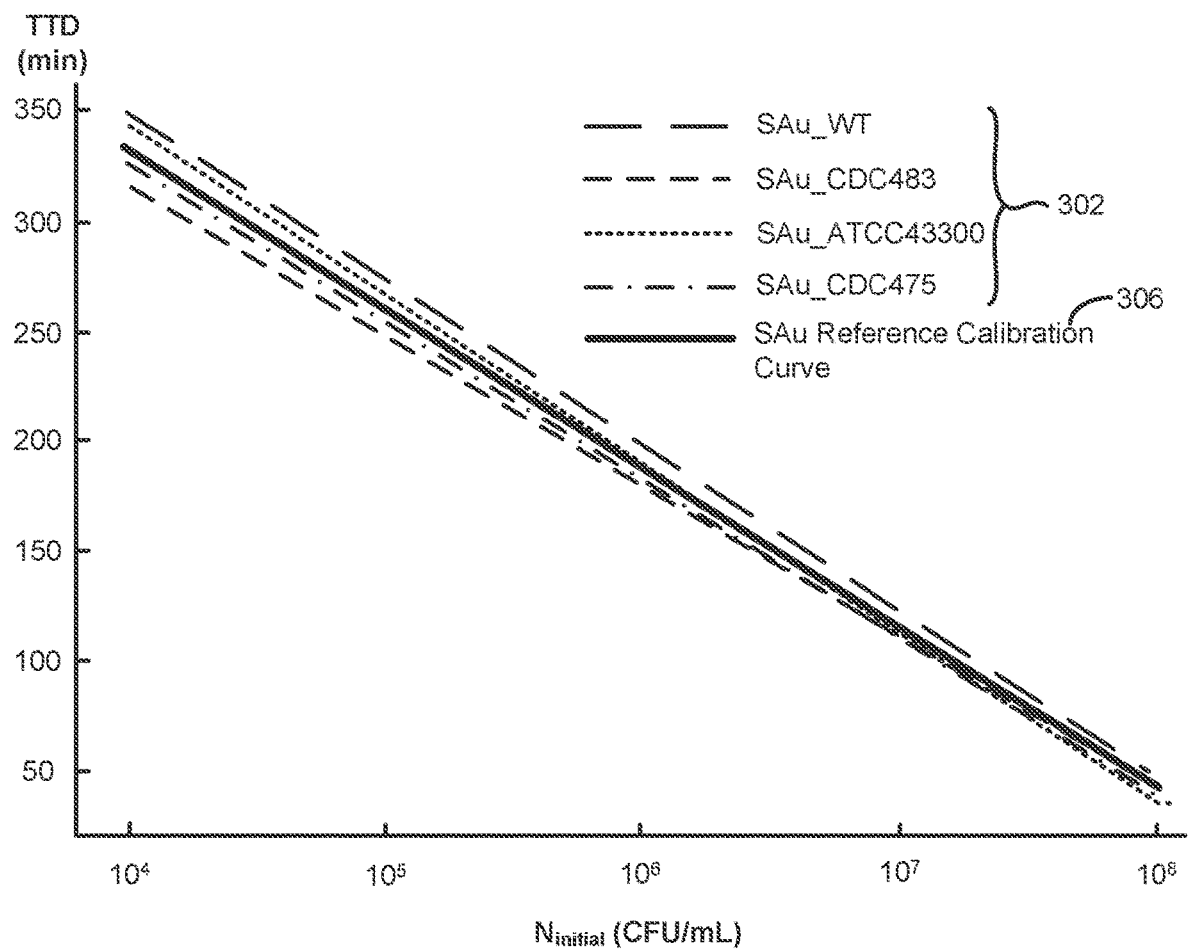
FIG. 3C illustrates a reference calibration curve and multiple strain-specific calibration curves for a particular species of an infectious agent.

FIG. 3C illustrates an SAu reference calibration curve 306 plotted on the same axes as multiple strain-specific SAu calibration curves 302 used to generate the slope and y-intercept of the SAu reference calibration curve 306. For example, the SAu reference calibration curve 306 can be generated using Equation 5 above but with $m_{strain\_specific}$ and $b_{strain\_specific}$ in the equation replaced by $m_{avg}$ and $b_{avg}$, respectively.

Figure 3D:
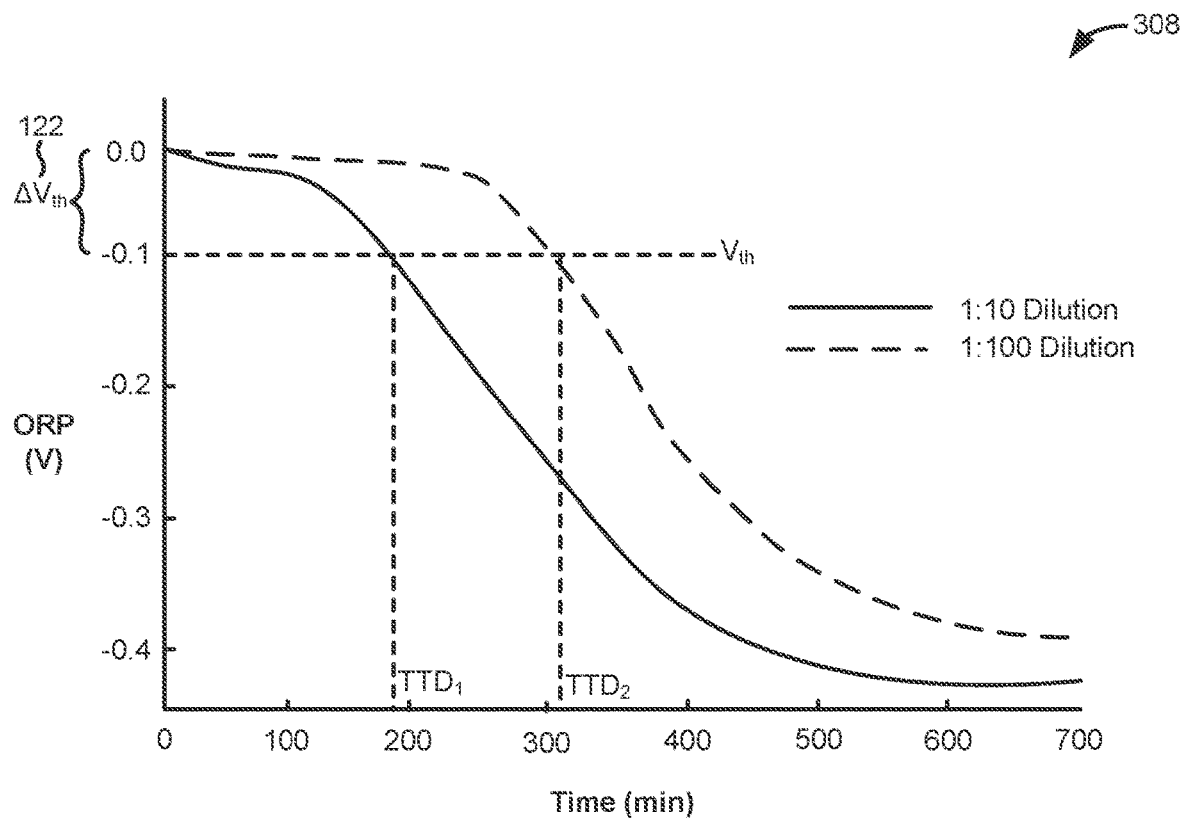
FIG. 3D illustrates two sample growth curves of diluted aliquots of a target sample comprising an infectious agent of an unknown strain.

FIG. 3D illustrates two sample growth curves 308 of diluted aliquots of a target sample 104 comprising SAu of an unknown strain. As shown in FIG. 3D, the first aliquot of the target sample 104 can be diluted by a dilution factor ($DF_1$) of 1:10 to yield a first diluted sample and the second aliquot of the target sample 104 can be diluted by a dilution factor ($DF_2$) of 1:100 to yield a second diluted sample. The first aliquot and the second aliquot can be diluted using a dilutive solution (such as the dilutive solution 112). FIG. 3D also illustrates that the solution characteristics of the two diluted samples can change as the amount of electro-active redox species in the samples changes due to the energy use, oxygen uptake or release, growth, or metabolism of the unknown strain of SAu in the diluted samples.

A predetermined ORP threshold level ($V_{th}$) can be set at −100 mV and the time it takes the solution characteristic of each of the first diluted sample and the second diluted sample to reach this $V_{th}$ can be recorded. The time it takes the first diluted sample to undertake a predetermined threshold change from 0 mV to −100 mV (also referred to as the $TTD_1$) can be recorded. For example, FIG. 3D shows the $TTD_1$ as 190 minutes. Moreover, the time it takes the second diluted sample to undertake a predetermined threshold change from 0 mV to −100 mV (referred to as the $TTD_2$) can be recorded. For example, FIG. 3D shows the $TTD_2$ as 310 minutes. As shown in FIG. 3D, the sample growth curve 308 of the second diluted sample can be time shifted with respect to the first diluted sample since a more dilute sample takes longer to reach a detectable level.

Figure 3E:
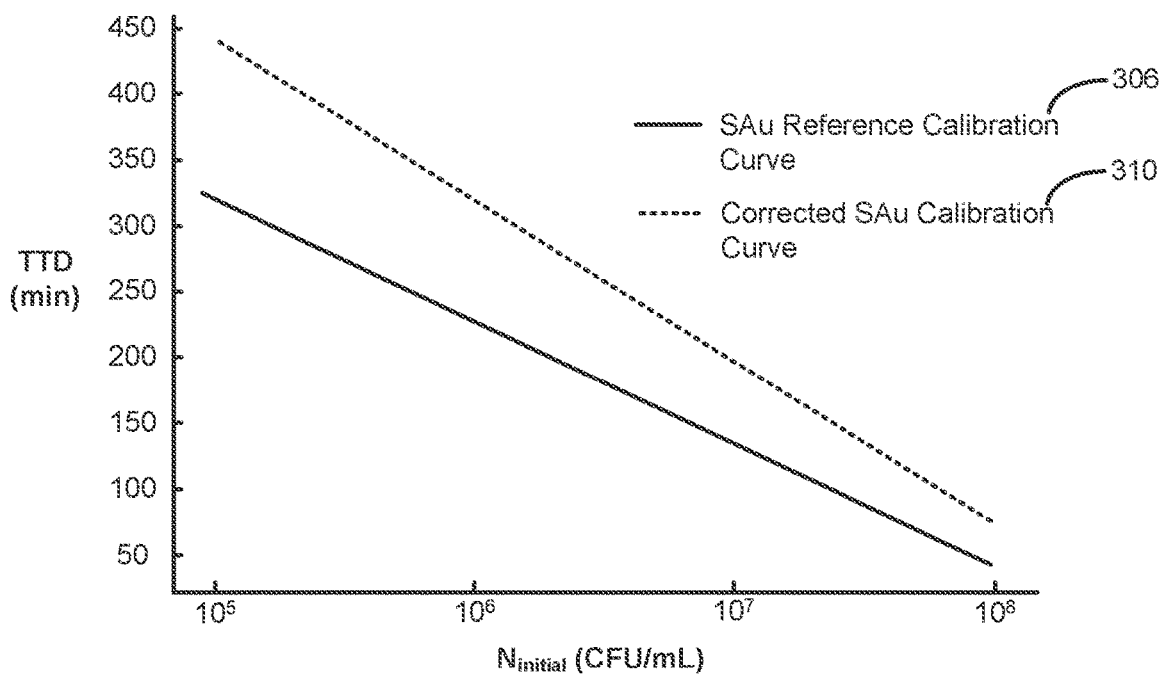
FIG. 3E illustrates the reference calibration curve of FIG. 3C in relation to a corrected calibration curve generated using the methods described herein.

FIG. 3E illustrates the SAu reference calibration curve 306 of FIG. 3C in relation to a corrected SAu calibration curve 310. The corrected SAu calibration curve 310 can be used to more accurately determine a concentration of the unknown strain of SAu in the target sample 104 compared to the SAu reference calibration curve 306. The corrected SAu calibration curve 310 can be generated by applying a correction factor (CF) to certain equation parameters of the SAu reference calibration curve 306.

For example, a computing device 120 can calculate a corrected calibration curve slope ($m_{corr}$) using Equation 1 provided above and where $TTD_2$=310 minutes, $TTD_1$=190 minutes, $DF_2$=100, $DF_1$=10, and a=10:

$$m_{corr} = \frac{-(TTD2 - TTD1)}{\log_a\left(\frac{DF_2}{DF_1}\right)}$$

$$m_{corr} = \frac{-(310 - 190)}{\log_{10}\left(\frac{100}{10}\right)}$$

$$m_{corr} = -120$$

In the calculation above, the variable "a" can be equal to 10 when 10 is used as the base of the log function in Equation 5 above. As previously discussed, "a" can be any positive real number other than 1.

The computing device 120 can also calculate a corrected calibration curve y-intercept ($b_{corr}$) using Equation 2 provided above, the calculated $m_{corr}$ value, and the stored $m_{avg}$ and $b_{avg}$ values for SAu:

$$b_{corr} = \frac{m_{corr}}{a_{avg}} \times b_{avg}$$

$$b_{corr} = \frac{-120}{-73} \times 625.2$$

$$b_{corr} = 1027.73$$

The value obtained by dividing $m_{corr}$ by $m_{avg}$ (the ratio of m values) can also be considered a correction factor or CF (that is $$CF = \frac{m_{corr}}{m_{avg}}).$$

For example, another way of expressing Equation 2 above can be:

$$b_{corr} = CF \times b_{avg}$$

With the $m_{corr}$ and $b_{corr}$ values calculated, the concentration of the unknown strain of SAu in the target sample 104 ($Conc_{target}$) can be calculated using either Equation 3 or Equation 4 above.

For example, using Equation 3 and with $DF_1=10$ and $TTD_1=190$ minutes, the $Conc_{target}$ can be calculated as:

$$Conc_{target} = 10 \times 10^{\left(\frac{190-1027.73}{-120}\right)}$$

$$Conc_{target} = 10^{7.98} \; CFU/mL$$

$$Conc_{target} = 9.5 \times 10^7 \; CFU/mL$$

Similarly, using Equation 4 and with $DF_2=100$ and $TTD_2=310$ minutes, the $Conc_{target}$ can be calculated as:

$$Conc_{target} = 10 \times 10^{\left(\frac{310-1027.73}{-120}\right)}$$

$$Conc_{target} = 10^{7.98} \; CFU/mL$$

$$Conc_{target} = 9.5 \times 10^7 \; CFU/mL$$

To highlight the importance of the correction steps described above, the $Conc_{target}$ can also be calculated using Equations 3 and 4 but with $m_{corr}$ substituted with $m_{avg}$ and $b_{corr}$ substituted with $b_{avg}$:

$$Conc_{target} = DF_1 \times a^{\left(\frac{TTD_1-b_{avg}}{m_{avg}}\right)}$$

$$Conc_{target} = 10 \times 10^{\left(\frac{190-625.2}{-73.0}\right)}$$

$$Conc_{target} = 10^{(6.96)}$$

$$Conc_{target} = 9.1 \times 10^6 \; CFU/mL$$

$$Conc_{target} = DF_2 \times a^{\left(\frac{TTD_2-b_{avg}}{m_{avg}}\right)}$$

$$Conc_{target} = 100 \times 10^{\left(\frac{310-625.2}{-73.0}\right)}$$

$$Conc_{target} = 10^{(6.32)}$$

$$Conc_{target} = 2.1 \times 10^6 \; CFU/mL$$

As can be seen by the concentration amounts calculated using the $m_{avg}$ and $b_{avg}$ values, the concentration amount is inconsistent across the two dilutions. In addition, the improved accuracy of the correction steps is apparent when the concentration of the unknown strain of SAu in the target sample 104 or $Conc_{target}$ is calculated to be approximately $1.0 \times 10^8$ CFU/mL using other prevailing methods.

Figure 4A:
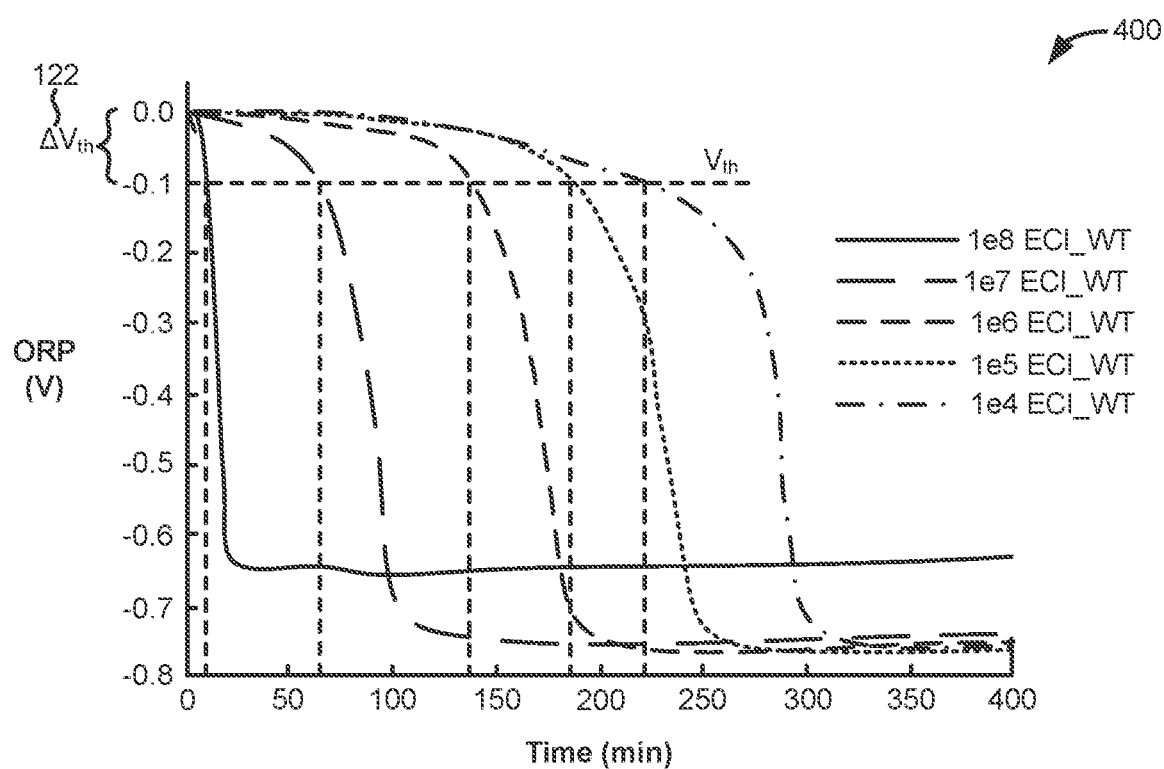
FIG. 4A illustrates additional strain-specific growth curves of infectious agent cultures of different starting concentrations.

FIGS. 4A to 4E illustrate an example application of the methods described herein for determining the concentration of an unknown strain of ECl in a target sample 104. FIG. 4A illustrates multiple growth curves 400 representing a change in the solution characteristic of prepared cultures 206 of a known strain of ECl (in this case, wild-type strain ECl or ECl_WT). The growth curves 400 can be recorded by monitoring the sensor output of one or more ORP sensors (including, but not limited to, the sensors 116) in fluid communication with the prepared cultures 206. The prepared cultures 206 can comprise different initial concentrations ($N_{initial}$) of ECl_WT (e.g., $1 \times 10^4$ CFU/mL, $1 \times 10^5$ CFU/mL, $1 \times 10^6$ CFU/mL, $1 \times 10^7$ CFU/mL, and $1 \times 10^8$ CFU/mL of ECl_WT).

The sensor output (voltage output in this case) can be a potential difference between an active electrode and a reference electrode such as the external reference electrode or the on-chip reference electrode (see FIGS. 7A and 7B). The voltage output of the one or more ORP sensors can change as the ORP of each of the prepared cultures 206 changes over time.

The voltage output can decrease as the solution characteristic of the prepared cultures 206 change due to the energy use, oxygen uptake or release, growth, or metabolism of the infectious agents 202 in solution. In some embodiments, the growth curve can follow a sigmoidal pattern or shape, a step function or shape, or other patterns or shapes. Over longer time scales, the growth curve can begin to increase or become more positive.

For example, the voltage output of the ORP sensor can decrease over time as the solution characteristic of each of the prepared cultures 206 changes as a result of cellular activity undertaken by the infectious agents 202 in solution. As a more specific example, the solution characteristic of the prepared cultures 206 can change as the amount of energy carriers (such as nicotinamide adenine dinucleotide (NADH) and flavin adenine dinucleotide ($FADH_2$)) in the sampled solution changes due to the growth of the infectious agents 202. Also, as another more specific example, the amount of oxygen depleted in the prepared cultures 206 can change due to the growth of the infectious agents 202 (e.g., ECl_WT) in solution.

Although outputs for ORP sensors are shown in FIGS. 4A-4E, it is contemplated by this disclosure that pH sensors can also be used in lieu of or in combination with ORP sensors. The pH sensors can be configured to respond to a change in the pH of the prepared cultures 206.

FIG. 4A also illustrates that a calibration time-to-detection ($TTD_{calibration}$) can also be recorded for each of the prepared cultures 206 of ECl_WT. The $TTD_{calibration}$ represents the time it takes the solution characteristic of each of the prepared cultures 206 to undertake a predetermined threshold change 122. For example, as shown in FIG. 4A, the time it takes the ORP of each of the prepared cultures 206 of ECl_WT to reach a predetermined threshold voltage of −100 mV (from a starting voltage of 0 V) can be recorded by the parameter analyzer 118, the computing device 120, or a combination thereof.

Figure 4B:
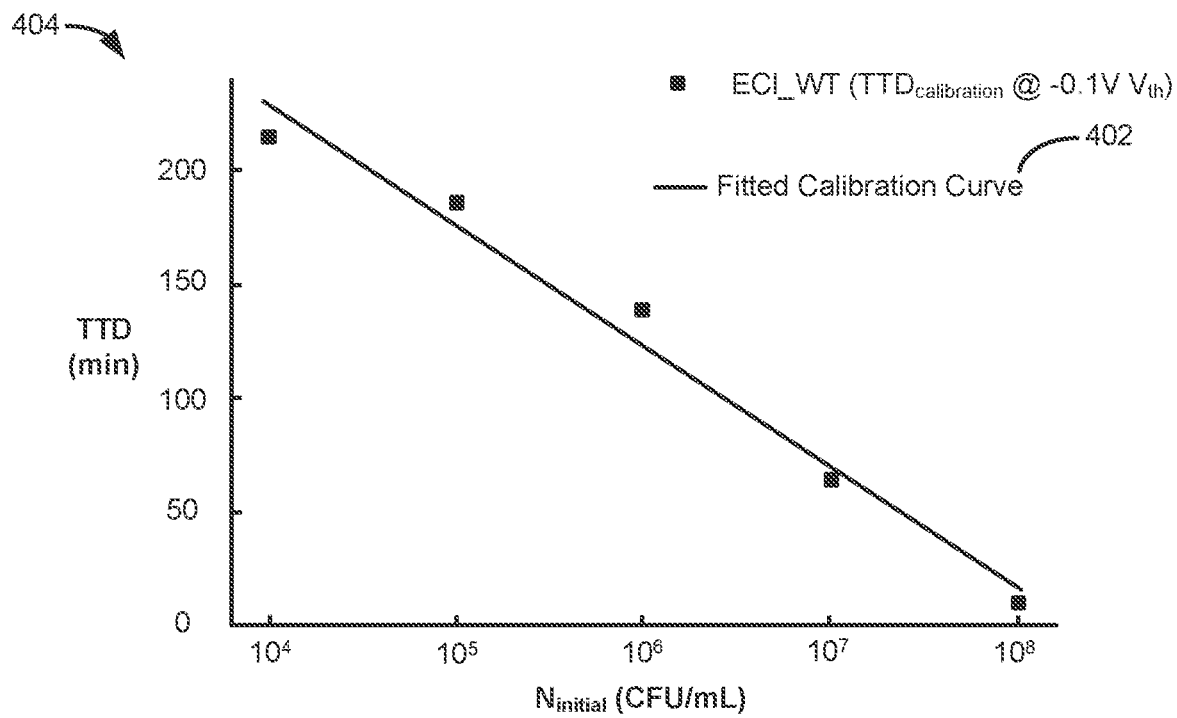
FIG. 4B illustrates a strain-specific calibration curve fitted to data obtained from the additional strain-specific growth curves.

FIG. 4B illustrates a strain-specific calibration curve 402 (in this case, the ECl_WT calibration curve) fitted to $TTD_{calibration}$ and $N_{initial}$ data obtained from the strain-specific growth curves 400 of FIG. 4A. For example, $TTD_{calibration}$ data and $N_{initial}$ data can be plotted on a semi-log plot (or linear-logarithmic plot) 404 as shown in FIG. 4B. The strain-specific calibration curve 402 can be fitted to the $TTD_{calibration}$ and $N_{initial}$ data using curve-fitting techniques. In one embodiment, the curve-fitting technique can be a least-squares curve fitting technique. In other embodiments, the curve-fitting technique can be a logarithmic regression or polynomial curve-fitting technique. The strain-specific calibration curve 402 can refer to one of the multiple calibration curves 204 discussed with respect to FIG. 2.

In one embodiment, the strain-specific calibration curve 402 for EC1_WT can be fitted to the $TTD_{calibration}$ and $N_{initial}$ data using Equation 5 above. In this and other embodiments (i.e., the prepared cultures 206 are cultures of EC1_WT), the curve fitting parameters $m_{strain\_specific}$ and $b_{strain\_specific}$ can refer to an EC1_WT calibration curve slope and an EC1_WT calibration curve y-intercept, respectively.

The same process can be repeated for other known strains of an infectious agent 202 of a particular species. For example, the same process can be repeated for other known strains of EC1 such as the CDC 32 type strain of EC1 or EC1_CDC32, the ATCC2341 strain of EC1 or EC1_ATCC2341, and the CDC 93 type strain of EC1 or EC1_CDC93 such that unique pairs of $m_{strain\_specific}$ and $b_{strain\_specific}$ are calculated for each of EC1_WT, EC1_CDC32, EC1_ATCC2341, and EC1_CDC93.

Table 3 below shows calibration curve slopes and calibration curve y-intercepts calculated for different strains of EC1 including EC1_WT, EC1_CDC32, EC1_ATCC2341, and EC1_CDC93. Table 3 also shows that an average calibration curve slope ($m_{avg}$) can be calculated by taking an average of the various EC1 calibration curve slopes. In addition, Table 3 also shows that an average calibration curve y-intercept ($b_{avg}$) can be calculated by taking an average of the various EC1 calibration curve y-intercepts.

TABLE 3

EC1 Calibration Curve Parameters

| EC1 Strain | Calibration Curve Slope (m) | Calibration Curve y-intercept (b) |
| --- | --- | --- |
| Wild-type (WT) | −52.7 | 438.8 |
| CDC 32 | −64.9 | 512.9 |
| ATCC 2341 | −62.4 | 515.4 |
| CDC 93 | −67.8 | 549.7 |
| EC1 Reference Calibration Curve | $m_{avg}$ = −61.95 | $b_{avg}$ = 504.2 |

The various EC1 calibration curve slopes and y-intercepts along with the $m_{avg}$ and the $b_{avg}$ values can be stored in a database on a memory device of the computing device 120 or stored in another database accessible to the computing device 120. Such stored values can be used to quantify a target sample 104 that immediately tests positive for EC1 but where the particular strain of EC1 is initially unknown.

Figure 4C:
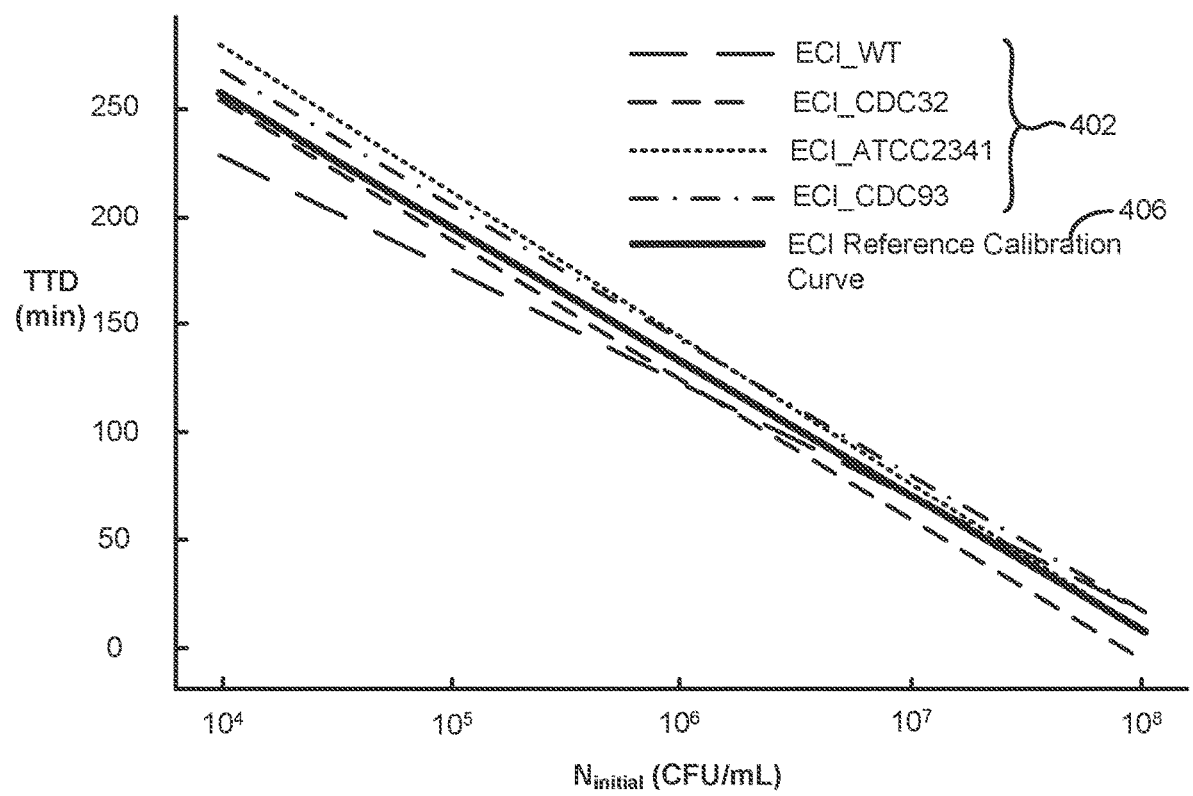
FIG. 4C illustrates another example of a reference calibration curve and multiple strain-specific calibration curves for a particular infectious agent species.

FIG. 4C illustrates an EC1 reference calibration curve 406 plotted on the same axes as multiple strain-specific EC1 calibration curves 402 used to generate the slope and y-intercept of the EC1 reference calibration curve 406. For example, the EC1 reference calibration curve 406 can be generated using Equation 5 above but with $m_{strain\_specific}$ and $b_{strain-specific}$ in the equation replaced by $m_{avg}$ and $b_{avg}$, respectively.

Figure 4D:
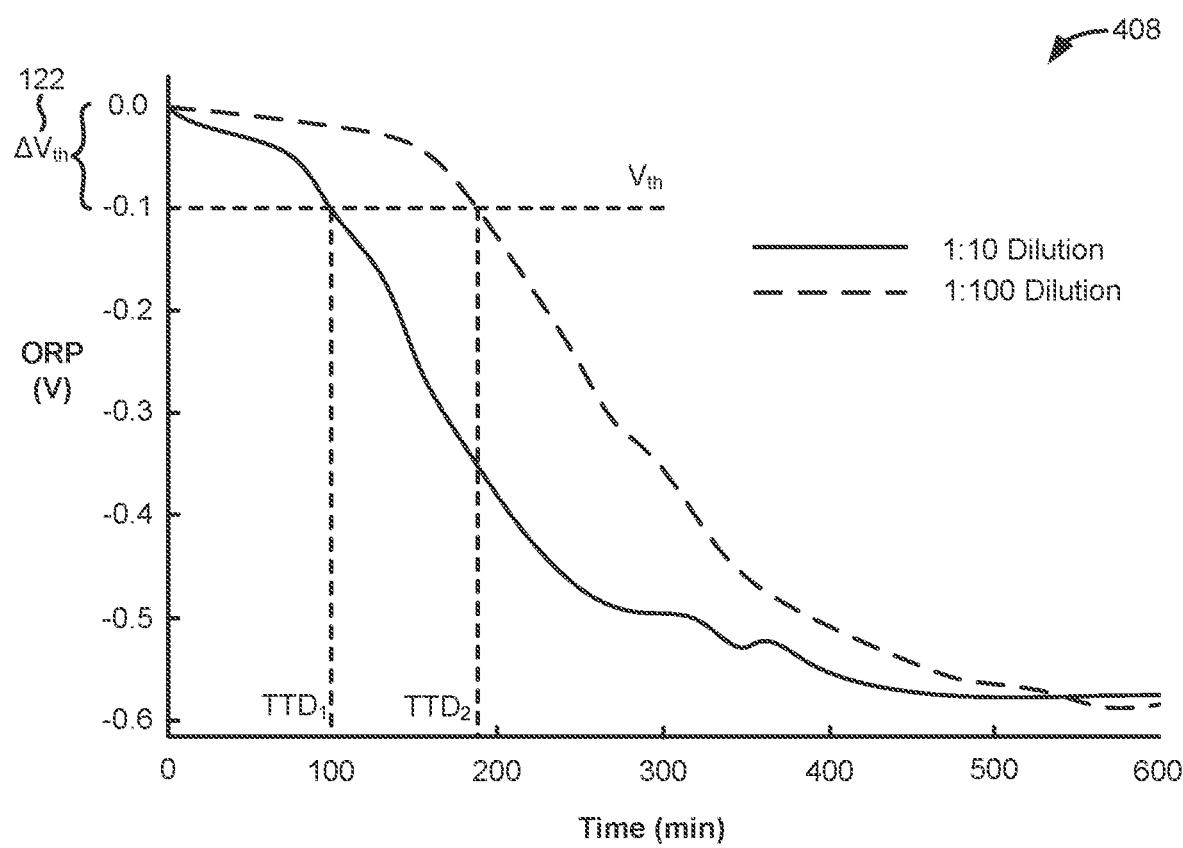
FIG. 4D illustrates two sample growth curves of diluted aliquots of another target sample comprising an infectious agent of an unknown strain.

FIG. 4D illustrates two sample growth curves 408 of diluted aliquots of a target sample 104 comprising EC1 of an unknown strain. As shown in FIG. 4D, the first aliquot of the target sample 104 can be diluted by a dilution factor ($DF_1$) of 1:10 to yield a first diluted sample and the second aliquot of the target sample 104 can be diluted by a dilution factor ($DF_2$) of 1:100 to yield a second diluted sample. The first aliquot and the second aliquot can be diluted using a dilutive solution (such as the dilutive solution 112). FIG. 4D also illustrates that the solution characteristics of the two diluted samples can change as the amount of electro-active redox species in the samples changes due to the energy use, oxygen uptake or release, growth, or metabolism of the unknown strain of EC1 in the diluted samples.

A predetermined ORP threshold level ($V_{th}$) can be set at −100 mV and the time it takes the solution characteristic of each of the first diluted sample and the second diluted sample to reach this $V_{th}$ can be recorded. The time it takes the first diluted sample to undertake a predetermined threshold change from 0 mV to −100 mV (also referred to as the $TTD_1$) can be recorded. For example, FIG. 4D shows the $TTD_1$ as 100 minutes. Moreover, the time it takes the second diluted sample to undertake a predetermined threshold change from 0 mV to −100 mV (referred to as the $TTD_2$) can be recorded. For example, FIG. 4D shows the $TTD_2$ as 190 minutes. As shown in FIG. 4D, the sample growth curve 408 of the second diluted sample can be time shifted with respect to the first diluted sample since a more dilute sample takes longer to reach a detectable level.

Figure 4E:
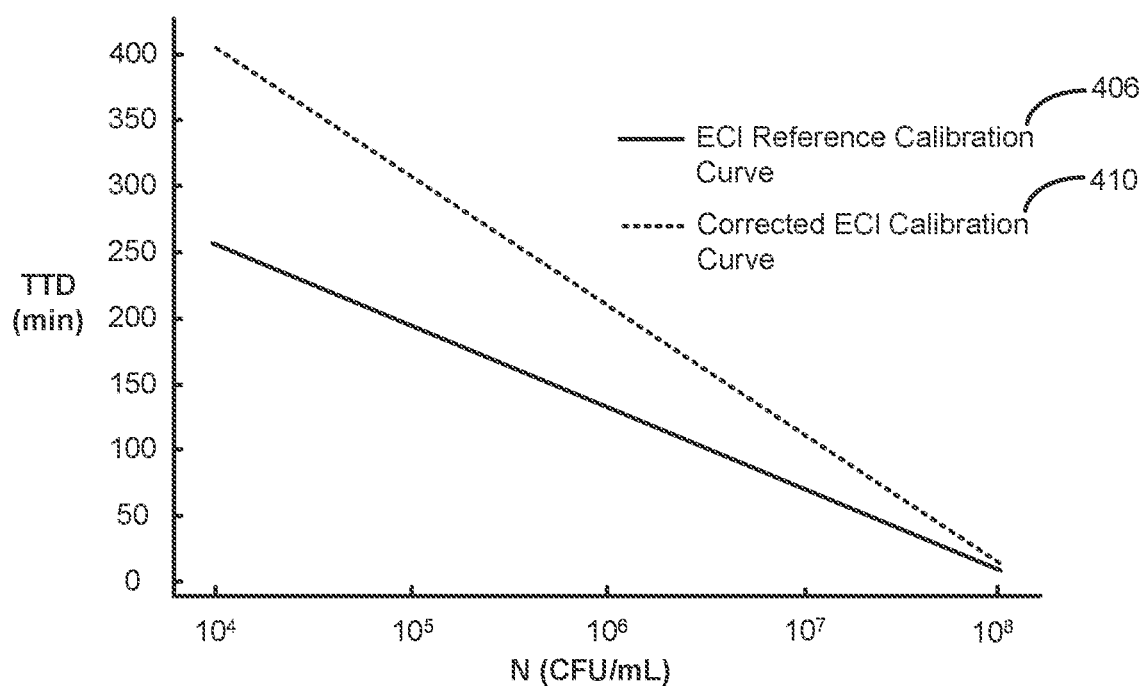
FIG. 4E illustrates the reference calibration curve of FIG. 4C in relation to a corrected calibration curve generated using the methods described herein.

FIG. 4E illustrates the EC1 reference calibration curve 406 of FIG. 4C in relation to a corrected EC1 calibration curve 410. The corrected EC1 calibration curve 410 can be used to more accurately determine a concentration of the unknown strain of EC1 in the target sample 104 compared to the EC1 reference calibration curve 406. The corrected EC1 calibration curve 410 can be generated by applying a correction factor (CF) to certain equation parameters of the EC1 reference calibration curve 406.

For example, a computing device 120 can calculate a corrected calibration curve slope ($m_{corr}$) using Equation 1 provided above and where $TTD_2$=190 minutes, $TTD_1$=100 minutes, $DF_2$=100, $DF_1$=10, and a=10:

$$m_{corr} = \frac{-(TTD2 - TTD1)}{\log_a\left(\frac{DF_2}{DF_1}\right)}$$

$$m_{corr} = \frac{-(190 - 100)}{\log_{10}\left(\frac{100}{10}\right)}$$

$$m_{corr} = -90$$

In the calculation above, the variable "a" can be equal to 10 when 10 is used as the base of the log function in Equation 5 above. As previously discussed, "a" can be any positive real number other than 1.

The computing device 120 can also calculate a corrected calibration curve y-intercept ($b_{corr}$) using Equation 2 provided above, the calculated $m_{corr}$ value, and the stored $m_{avg}$ and $b_{avg}$ values for EC1:

$$b_{corr} = \frac{m_{corr}}{m_{avg}} \times b_{avg}$$

$$b_{corr} = \frac{-90}{-61.95} \times 504.2$$

$$b_{corr} = 732.49$$

The value obtained by dividing $m_{corr}$ by $m_{avg}$ (the ratio of m values) can also be considered a correction factor or CF (that is $$CF = \frac{m_{corr}}{m_{avg}}\Bigg).$$

For example, another way of expressing Equation 2 above can be:

$$b_{corr} = CF \times b_{avg}$$

With the $m_{corr}$ and $b_{corr}$ values calculated, the concentration of the unknown strain of ECl in the target sample 104 (Conc$_{target}$) can be calculated using either Equation 3 or Equation 4 above.

For example, using Equation 3 and with DF$_1$=10 and TTD$_1$=100 minutes, the Conc$_{target}$ can be calculated as:

$$Conc_{target} = 10 \times 10^{\left(\frac{100-732.49}{-90}\right)}$$

$$Conc_{target} = 10^{8.03} \text{ CFU/mL}$$

$$Conc_{target} = 1.1 \times 10^8 \text{ CFU/mL}$$

Similarly, using Equation 4 and with DF$_2$=100 and TTD$_2$=190 minutes, the Conc$_{target}$ can be calculated as:

$$Conc_{target} = 100 \times 10^{\left(\frac{190-732.49}{-90}\right)}$$

$$Conc_{target} = 10^{8.03} \text{ CFU/mL}$$

$$Conc_{target} = 1.1 \times 10^8 \text{ CFU/mL}$$

To highlight the importance of the correction steps described above, the Conc$_{target}$ can also be calculated using Equations 3 and 4 but with $m_{corr}$ substituted with $m_{avg}$ and $b_{corr}$ substituted with $b_{avg}$:

$$Conc_{target} = DF_1 \times a^{\left(\frac{TTD_1 - b_{avg}}{m_{avg}}\right)}$$

$$Conc_{target} = 10 \times 10^{\left(\frac{100-504.2}{-61.95}\right)}$$

$$Conc_{target} = 10^{(7.52)}$$

$$Conc_{target} = 3.3 \times 10^7 \text{ CFU/mL}$$

$$Conc_{target} = DF_2 \times a^{\left(\frac{TTD_2 b_{avg}}{m_{avg}}\right)}$$

$$Conc_{target} = 100 \times 10^{\left(\frac{190-504.2}{-61.95}\right)}$$

$$Conc_{target} = 10^{(7.07)}$$

$$Conc_{target} = 1.2 \times 10^7 \text{ CFU/mL}$$

As can be seen by the concentration amounts calculated using the $m_{avg}$ and $b_{avg}$ values, the concentration amount is inconsistent across the two dilutions. In addition, the improved accuracy of the correction steps is apparent when the concentration of the unknown strain of ECl in the target sample 104 or Conc$_{target}$ is calculated to be approximately $1.0 \times 10^8$ CFU/mL using other prevailing methods.

Figure 5A:
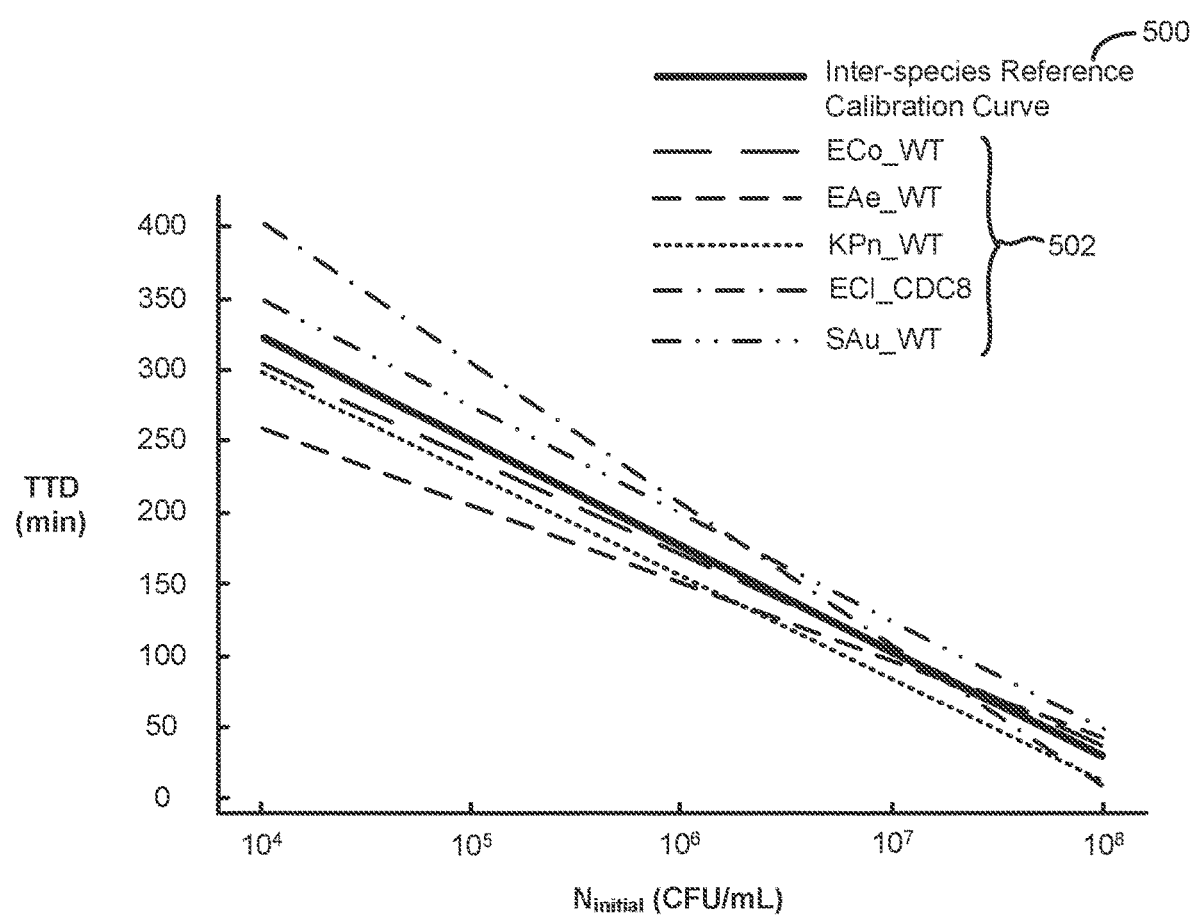
FIG. 5A illustrates a reference calibration curve and multiple calibration curves for infectious agents of multiple species.
Figure 5B:
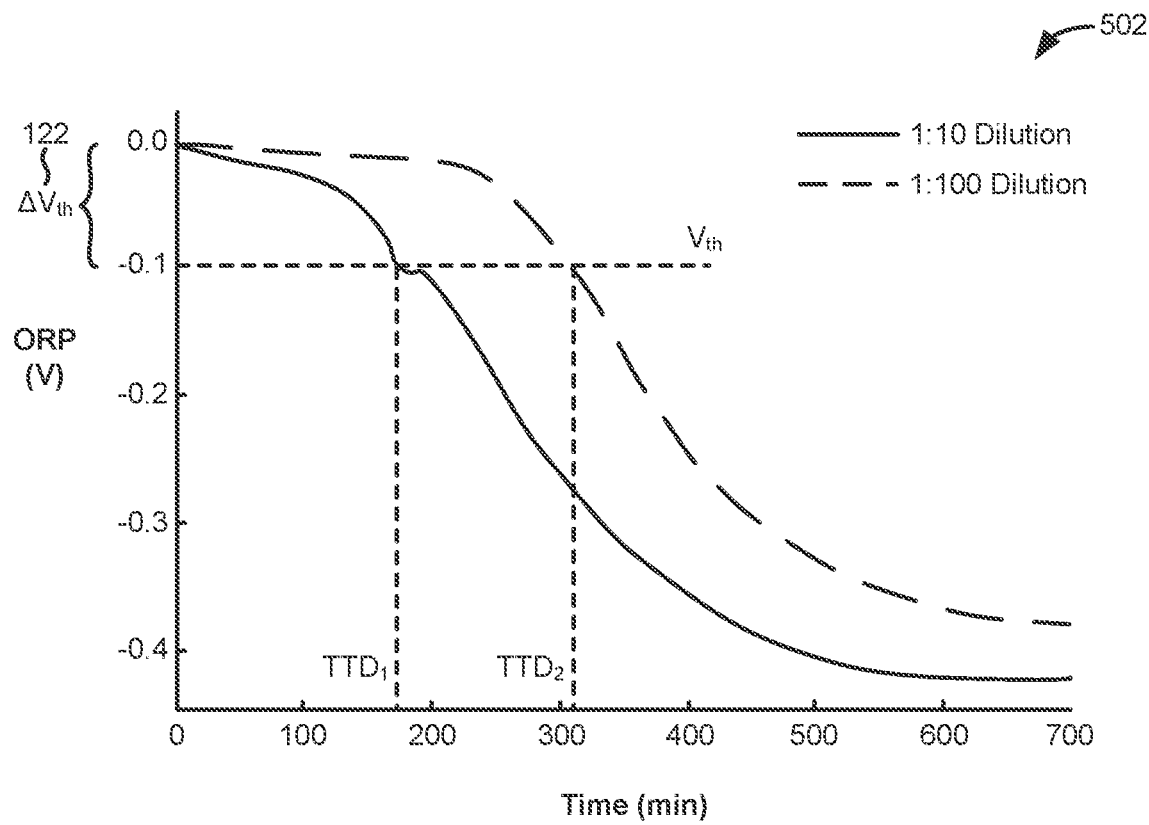
FIG. 5B illustrates two sample growth curves of diluted aliquots of an additional target sample comprising an infectious agent of an unknown strain.
Figure 5C:
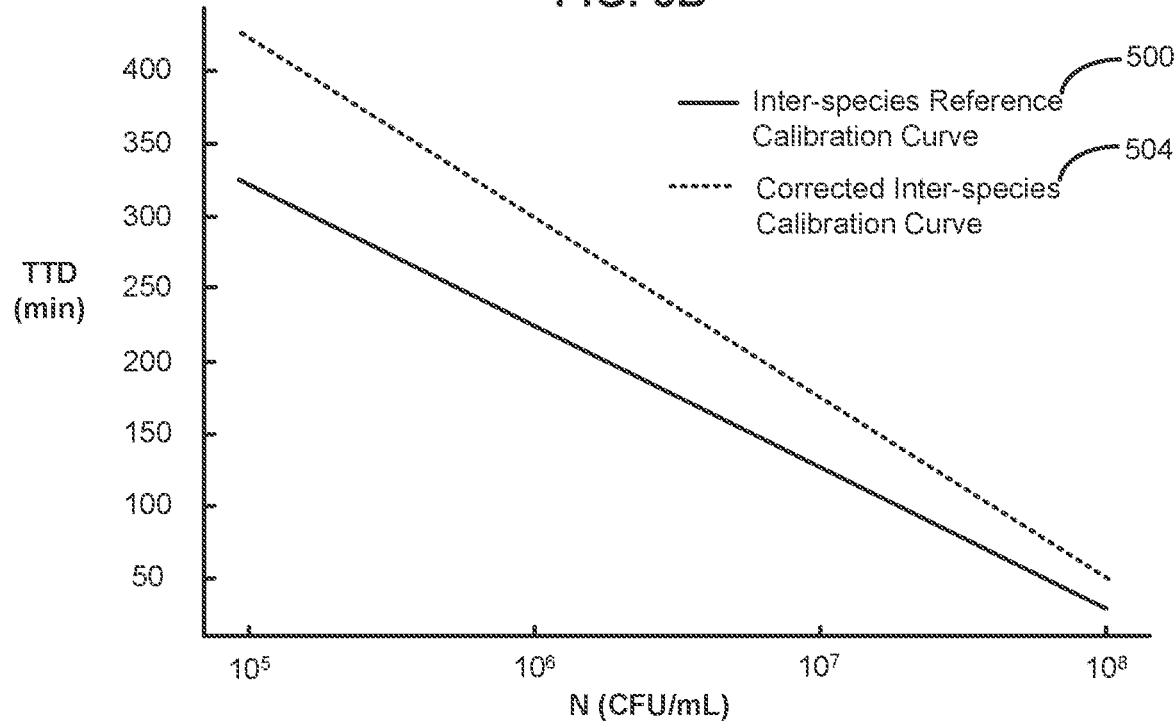
FIG. 5C illustrates the reference calibration curve of FIG. 5A in relation to a corrected calibration curve generated using the methods described herein.

FIGS. 5A-5C illustrate an example application of the methods described herein for determining the concentration of an unknown strain of an infectious agent 102 in a target sample 104 using an inter-species reference calibration curve 500. The inter-species reference calibration curve 500 can be generated from multiple calibration curves 502 (such as multiple strain-specific calibration curves) representing the growth behavior of multiple species of infectious agents.

For example, at least one of the infectious agents 202 used to generate the multiple calibration curves 502 can be of a different species from the infectious agent 102 of the unknown strain in the target sample 104. In some embodiments, the method used to determine the concentration of the unknown strain of the infectious agent 102 can begin by determining at least one of the species, the genus, the family, the order, the class, the phylum, the kingdom, and the domain of the infectious agent 102 in the target sample 104. In these and other embodiments, the computing device 120 can then select the appropriate calibration curves 502 used to generate the inter-species reference calibration curve 500 based on at least one of the species, the genus, the family, the order, the class, the phylum, the kingdom, and the domain of the infectious agent 102 in the target sample 104. For example, the target sample 104 can be determined to comprise bacteria from the phylum Proteobacteria. In this example, the computing device 120 can generate the inter-species reference calibration curve 500 using calibration curves 502 representing different types of bacteria within the phylum Proteobacteria. In another example, the target sample 104 can be determined to comprise an infectious agent 102 from the domain Bacteria. In this example, the computing device 120 can generate the inter-species reference calibration curve 500 using calibration curves 502 representing different types of bacteria from across multiple phyla or encompassing both Gram-positive and Gram-negative bacteria.

FIG. 5A illustrates the inter-species reference calibration curve 500 plotted on the same axes as multiple calibration curves 502 of multiple infectious agent species. In addition, Table 4 below shows calibration curve slopes and calibration curve y-intercepts calculated for different strains of ECo, EAe, KPn, ECl, and SAu. For example, calibration curve slopes and calibration curve y-intercepts can be calculated for Eco_WT, EAe_WT, KPn_WT, ECl CDCl$_8$, and SAu_WT. Table 4 below also shows that an average calibration curve slope ($m_{avg}$) can be calculated for the inter-species reference calibration curve 500 by taking an average of the various calibration curve slopes. Moreover, Table 4 shows that an average calibration curve y-intercept ($b_{avg}$) can be calculated for the inter-species reference calibration curve 500 by taking an average of the various calibration curve y-intercepts.

TABLE 4

Calibration Curve Parameters of Multiple Calibration Curves Across Different Species

| Infectious Agent | Calibration Curve Slope (m) | Calibration Curve y-intercept (b) |
| --- | --- | --- |
| Eco_WT | −66.7 | 570.0 |
| EAe_WT | −54.2 | 474.9 |
| KPn_WT | −71.5 | 583.2 |
| ECl_CDC8 | −98.1 | 793.8 |
| SAu_WT | −75.3 | 649.4 |
| Inter-species Reference Calibration Curve | $m_{avg}$ = −73.2 | $b_{avg}$ = 614.3 |

The various calibration curve slopes and y-intercepts along with the $m_{avg}$ and the $b_{avg}$ values provided in Table 4 above can be stored in a database on a memory device of the computing device 120 or stored in another database accessible to the computing device 120. The inter-species reference calibration curve 500 can be generated using Equation 5 above but with $m_{strain-specific}$ and $b_{strain\_specific}$ in the equation replaced by $m_{avg}$ and $b_{avg}$, respectively.

FIG. 5B illustrates two sample growth curves 502 of diluted aliquots of a target sample 104 comprising an infectious agent 102 of an unknown strain. As shown in FIG.

5B, the first aliquot of the target sample 104 can be diluted by a dilution factor ($DF_1$) of 1:10 to yield a first diluted sample and the second aliquot of the target sample 104 can be diluted by a dilution factor ($DF_2$) of 1:100 to yield a second diluted sample. The first aliquot and the second aliquot can be diluted using a dilutive solution (such as the dilutive solution 112). FIG. 5B also illustrates that the solution characteristics of the two diluted samples can change as the amount of electro-active redox species in the samples changes due to the energy use, oxygen uptake or release, growth, or metabolism of the unknown infectious agent 102 in the diluted samples.

A predetermined ORP threshold level ($V_{th}$) can be set at −100 mV and the time it takes the solution characteristic of each of the first diluted sample and the second diluted sample to reach this $V_{th}$ can be recorded. The time it takes the first diluted sample to undertake a predetermined threshold change from 0 mV to −100 mV (also referred to as the $TTD_1$) can be recorded. For example, FIG. 5B shows the $TTD_1$ as 180 minutes. Moreover, the time it takes the second diluted sample to undertake a predetermined threshold change from 0 mV to −100 mV (referred to as the $TTD_2$) can be recorded. For example, FIG. 5B shows the $TTD_2$ as 310 minutes. As shown in FIG. 5B, the sample growth curve 502 of the second diluted sample can be time shifted with respect to the first diluted sample since a more dilute sample takes longer to reach a detectable level.

FIG. 5C illustrates the inter-species reference calibration curve 500 of FIG. 5A in relation to a corrected inter-species calibration curve 504. The corrected inter-species calibration curve 504 can be used to more accurately determine a concentration of an unknown infectious agent 102 in a target sample 104 compared to the inter-species reference calibration curve 500. The corrected inter-species calibration curve 504 can be generated by applying a correction factor (CF) to certain equation parameters of the inter-species reference calibration curve 500.

For example, a computing device 120 can calculate a corrected calibration curve slope ($m_{corr}$) using Equation 1 provided above and where $TTD_2$=310 minutes, $TTD_1$=180 minutes, $DF_2$=100, $DF_1$=10, and a=10:

$$m_{corr} = \frac{-(TTD2 - TTD1)}{\log_a\left(\frac{DF2}{DF1}\right)}$$

$$m_{corr} = \frac{-(310 - 180)}{\log_{10}\left(\frac{100}{10}\right)}$$

$$m_{corr} = -130$$

In the calculation above, the variable "a" can be equal to 10 when 10 is used as the base of the log function in Equation 5 above. As previously discussed, "a" can be any positive real number other than 1.

The computing device 120 can also calculate a corrected calibration curve y-intercept ($b_{corr}$) using Equation 2 provided above, the calculated $m_{corr}$ value, and the stored $m_{avg}$ and $b_{avg}$ values:

$$b_{corr} = \frac{m_{corr}}{m_{avg}} \times b_{avg}$$

$$b_{corr} = \frac{-130}{-73.2} \times 614.3$$

$$b_{corr} = 1090.97$$

The value obtained by dividing $m_{corr}$ by $m_{avg}$ (the ratio of m values) can also be considered a correction factor or CF (that is $$CF = \frac{m_{corr}}{m_{avg}}\right).$$

For example, another way of expressing Equation 2 above can be:

$$b_{corr} = CF \times b_{avg}$$

With the $m_{corr}$ and $b_{corr}$ values calculated, the concentration of the unknown infectious agent 102 in the target sample 104 ($Conc_{target}$) can be calculated using either Equation 3 or Equation 4 above.

For example, using Equation 3 and with $DF_1$=10 and $TTD_1$=180 minutes, the $Conc_{target}$ can be calculated as:

$$Conc_{target} = 10 \times 10^{\left(\frac{180 - 1090.97}{-130}\right)}$$

$$Conc_{target} = 10^{8.01} \text{ CFU/mL}$$

$$Conc_{target} = 1.0 \times 10^8 \text{ CFU/mL}$$

Similarly, using Equation 4 and with $DF_2$=100 and $TTD_2$=310 minutes, the $Conc_{target}$ can be calculated as:

$$Conc_{target} = 100 \times 10^{\left(\frac{310 - 1090.97}{-130}\right)}$$

$$Conc_{target} = 10^{8.01} \text{ CFU/mL}$$

$$Conc_{target} = 1.0 \times 10^8 \text{ CFU/mL}$$

To highlight the importance of the correction steps described above, the $Conc_{target}$ can also be calculated using Equations 3 and 4 but with $m_{corr}$ substituted with $m_{avg}$ and $b_{corr}$ substituted with $b_{avg}$:

$$Conc_{target} = DF_1 \times a^{\left(\frac{TTD_1 b_{avg}}{m_{avg}}\right)}$$

$$Conc_{target} = 10 \times 10^{\left(\frac{180 - 61.43}{-73.2}\right)}$$

$$Conc_{target} = 10^{(6.93)}$$

$$Conc_{target} = 8.5 \times 10^6 \text{ CFU/mL}$$

$$Conc_{target} = DF_2 \times a^{\left(\frac{TTD_2 b_{avg}}{m_{avg}}\right)}$$

$$Conc_{target} = 100 \times 10^{\left(\frac{310 - 61.43}{-73.2}\right)}$$

$$Conc_{target} = 10^{(6.16)}$$

$$Conc_{target} = 1.4 \times 10^6 \text{ CFU/mL}$$

As can be seen by the concentration amounts calculated using the $m_{avg}$ and $b_{avg}$ values, the concentration amount is inconsistent across the two dilutions. In addition, the improved accuracy of the correction steps is apparent when the concentration of the unknown infectious agent 102 in the target sample 104 or $\text{Conc}_{target}$ is calculated to be approximately $1.0 \times 10^8$ CFU/mL using other prevailing methods.

Figure 6:
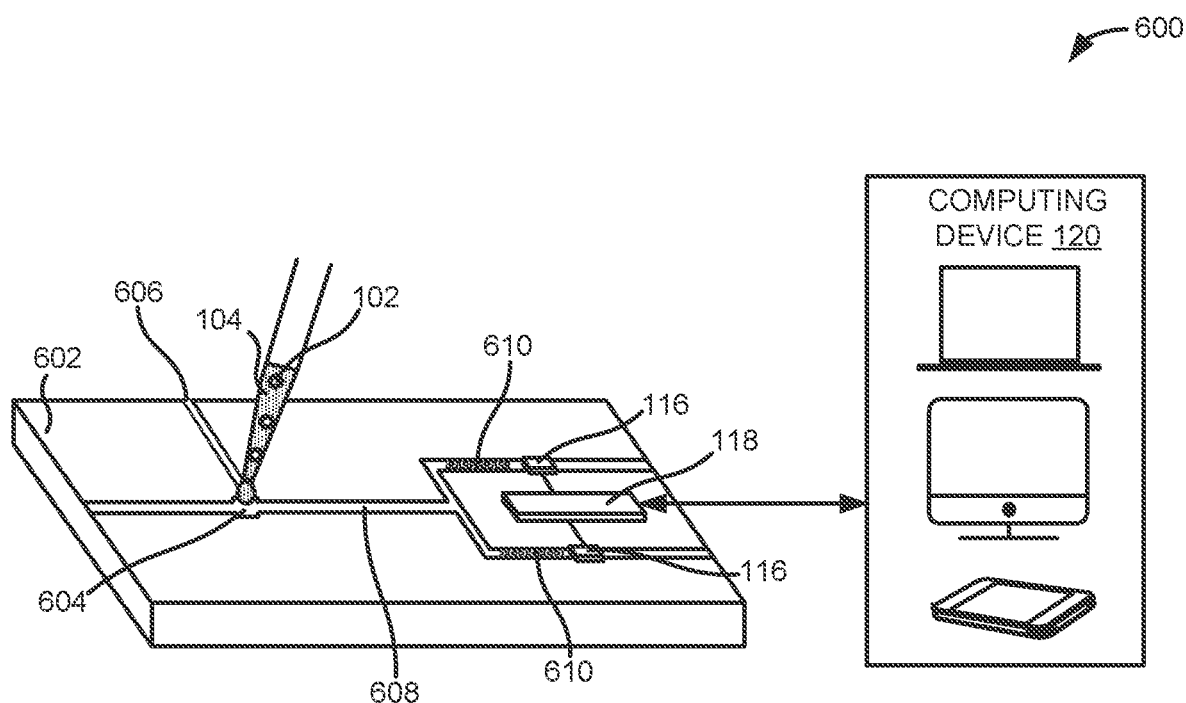
FIG. 6 illustrates one embodiment of a system and devices for determining the concentration of an infectious agent in a target sample.

FIG. 6 illustrates one embodiment of a system 600 for determining the concentration of an infectious agent 102 in a target sample 104. It is contemplated by this disclosure, and it should be understood by one or ordinary skill in the art, that the system 600 can be used to undertake any of the steps of method 100 or method 200 described in the preceding sections.

FIG. 6 illustrates that the system 600 can comprise one or more sensors 116 fabricated or positioned on a surface of or within a substrate 602. The substrate 602 can also have a sample receiving surface 604 or port, one or more metering conduits 606, and one or more sample delivery conduits 608, defined on the surface of or within the substrate 602. The sample receiving surface 604 or port can be in fluid communication with the one or more metering conduits 606, the one or more sample delivery conduits 608, or a combination thereof. In addition, the one or more sample delivery conduits 608 can also be in fluid communication with each of the sensors 116.

The substrate 602 can be comprised of a polymeric material, a metal, a ceramic, a semiconductor material, an insulator, or a combination thereof. In one embodiment, the sample receiving surface 604 can be a flat surface for receiving the target sample 104. In other embodiments, the sample receiving surface 604 can be a concave or tapered surface of a well, divot, dish, or container. For example, the target sample 104 can be injected, pipetted, pumped, spotted, or otherwise introduced to the sample receiving surface 604.

The one or more metering conduits 606 can be channels, passageways, capillaries, tubes, parts therein, or combinations thereof for delivering the dilutive solution 112 to the target sample 104 on the sample receiving surface 604. For example, the one or more metering conduits 606 can refer to channels, passageways, capillaries, or tubes defined on the substrate 602. Also, for example, the one or more metering conduits 606 can refer to channels, passageways, capillaries, or tubes serving as part of hydraulic pump, a pneumatic pump, peristaltic pump, a vacuum or positive pressure pump, a manual or mechanical pump, a syringe pump, or a combination thereof. For example, the one or more metering conduits 606 can be microfluidic channels or tubes or channels serving as part of a vacuum system.

In some embodiments, the one or more metering conduits 606 can be configured to dilute aliquots of the target sample 104 with the dilutive solution 112 to a dilution ratio between about 1:1 to about $1:10^7$. In other embodiments, the one or more metering conduits 606 can be configured to dilute aliquots of the target sample 104 to a dilution ratio beyond $1:10^7$.

For example, the system 600 can be used to undertake step 1B of the method 100. The one or more metering conduits 606 can be used to dilute a first aliquot of the target sample 104 by $DF_1$ to yield a first diluted sample. In addition, the one or more metering conduits 606 can also be used to dilute a second aliquot of the target sample 104 by $DF_2$ to yield a second diluted sample.

The one or more sample delivery conduits 608 can also introduce the diluted samples to the sensors 116 such that the diluted samples are in fluid communication with at least part of the sensors 116. The sample delivery conduits 608 can refer to channels, passageways, capillaries, tubes, parts therein, or combinations thereof for delivering the diluted samples to the sensors 116. For example, the one or more sample delivery conduits 608 can introduce the first diluted sample to the first sensor and introduce the second diluted sample to the second sensor. The sample delivery conduits 608 can serve the same function as the fluid delivery conduits 108 of FIG. 1.

As shown in the example embodiment of FIG. 6, the one or more sample delivery conduits 608 can also comprise growth media 610 or growth inducer. The growth media 610 or growth inducer can be the same growth media or growth inducer discussed in connection with FIG. 1. For example, the sample delivery conduits 608 can be covered or coated by a lyophilized or dried form of the growth media 610 or the growth inducer. In other embodiments, the sample delivery conduits 608 can contain growth media 610 or grow inducer in an aqueous form. In these and other embodiments, the dilutive solution 112 delivered by the one or more metering conduits 606 can be a saline solution, deionized water, or a combination thereof. The dilutive solution 112 can dilute the target sample 104 and deliver the diluted sample through the sample delivery conduits 608 to the sensors 116 such that the diluted samples mix with the growth media 610 en route to the sensors 116. In other embodiments not shown in the figures, at least one layer of the sensor 116 or a surface in a vicinity of the sensor 116 can be coated or covered by the growth media 610 in lyophilized or dried form and the diluted samples can mix with the growth media 610 when the diluted samples are in fluid communication with the part of the sensor 116 or part of the area covered by the growth media 610.

Although not shown in FIG. 6, the system 600 can also comprise an incubating component configured to heat the substrate 602 or portions therein, the diluted samples, or a combination thereof. For example, the incubating component can heat the diluted samples to a temperature of between about 30° C. and about 40° C. (e.g., 35° C.±2° C.) for a period of time.

In addition, one or more parameter analyzers 118 can also be fabricated or located on the substrate 602 and electrically or communicatively coupled to the one or more sensors 116. In other embodiments, the one or more parameter analyzers 118 can be standalone devices such as a voltmeter or a multimeter electrically coupled to the sensors 116. Moreover, one or more computing devices 120 can also be electrically or communicatively coupled to the one or more parameter analyzers 118, the one or more sensor 116, or a combination thereof. In some embodiments, the computing device 120 and the parameter analyzer 118 can be integrated into one device.

The sensors 116 can be configured to respond to a change in a solution characteristic of the diluted samples. For example, the first sensor can be configured to detect a change in the solution characteristic of the first diluted sample and the second sensor can be configured to detect a change in the solution characteristic of the second diluted sample. In some embodiments, the sensors 116 can be oxidation reduction potential (ORP) sensors configured to respond to a change in the ORP of the diluted samples (ORP sensors will be discussed in more detail in the following sections with respect to FIGS. 7A and 7B). In other embodiments, the sensors 116 can be pH sensors configured to respond to a change in the pH of the diluted samples (pH sensors will be discussed in more detail in the following sections with respect to FIGS. 8A and 8B).

The substrate 602, the sensors 116, the parameter analyzers 118, the sample receiving surface 604, the metering conduits 606, the sample delivery conduits 608, or a combination thereof can be part of a cartridge, a test strip, an integrated circuit, a micro-electro-mechanical system (MEMS) device, a microfluidic chip, or a combination thereof. In these and other embodiments, the substrate 602 can be part of a lab-on-a-chip (LOC) device. In all such embodiments, the sensors 116 can comprise components of such circuits, chips, or devices including, but not limited to, one or more transistors, gates, or other electrical components.

As shown in FIG. 6, one or more computing device 120 can be electrically or communicatively coupled to the sensors 116, the one or more parameter analyzers 118, or a combination thereof. In some embodiments, the computing device 120 can be a mobile device, a handheld device, a tablet device, a laptop or desktop computer. In these and other embodiments, the parameter analyzers 118, the sensors 116, or a combination thereof can wirelessly communicate a signal or result to computing device 120.

The computing device 120 can comprise one or more processors programmed to store and evaluate information or data received from the sensors 116, the one or more parameter analyzers 118, or a combination thereof. For example, the one or more processors of the computing device 120 can be programmed to monitor the solution characteristics of the diluted samples in fluid communication with the sensors 116. The one or more processors of the computing device 120 can undertake any of the steps 1E, 1F, 1G, and 1H of method 100 including determining a first time-to-detection ($TTD_1$) representing the time it takes the solution characteristic of the first diluted sample to undertake a predetermined threshold change and determining a second time-to-detection ($TTD_2$) representing the time it takes the solution characteristic of the second diluted sample to undertake the predetermined threshold change. In addition, the one or more processors of the computing device 120 can also calculate a corrected calibration curve slope ($m_{corr}$) using at least the $TTD_2$, the $TTD_1$, the $DF_2$, and the $DF_1$ and calculate an average calibration curve slope ($m_{avg}$) and an average calibration curve y-intercept ($b_{avg}$) from equation parameters obtained from multiple calibration curves representing growth behavior of infectious agents of different known strains.

Moreover, the one or more processors of the computing device 120 can calculate a corrected calibration curve y-intercept ($b_{corr}$) using at least the $m_{corr}$, the $m_{avg}$, and the $b_{avg}$ and determine the concentration of the infectious agent 102 in the target sample 104 using either the $m_{corr}$, the $b_{corr}$, the $TTD_1$, and the $DF_1$ or the $m_{corr}$, the $b_{corr}$, the $TTD_2$, and the $DF_2$.

Although FIG. 6 shows two sensors 116 on the substrate 602, it is contemplated by this disclosure that more than two sensors 116 can be fabricated or otherwise positioned on the substrate 602. In addition, the number of sample receiving surfaces 604, metering conduits 606, and sample delivery conduits 608 can also be increased and multiple target samples 104 can be quantified simultaneously or concurrently such that the system 600 is a multiplex system.

It should be understood by one or ordinary skill in the art that the system 600 can be used to undertake the example quantification procedures detailed in FIGS. 3A-3E, FIGS. 4A-4E, and FIGS. 5A-5C. Moreover, a variant of the system 600 having multiple sample receiving surfaces 604 or ports, metering conduits 606, and sample delivery conduits 608 can also be used to undertake the calibration steps 2A-2E of method 200 shown in FIG. 2.

FIG. 7A illustrates a schematic of one embodiment of an ORP sensor 700 used as part of the methods and systems described herein. The sensor 700 of FIG. 7A can be or refer to any of the sensors 116 depicted in FIGS. 1, 2, and 6 (including any of the sensors 116 referred to as the first sensor or the second sensor). The sensor 700 can be an electrochemical cell comprising an active electrode 701 and an external reference electrode 702. In some embodiments of the sensor 700, the active electrode 701 and the external reference electrode 702 are the only electrodes of the sensor 700.

The active electrode 701 can extend from or be disposed on a substrate layer 704. The substrate layer 704 can be composed of, but is not limited to, any non-conducting material such as a polymer, an oxide, a ceramic, or a composite thereof. The electrochemical cell can be surrounded or contained by walls 706 configured to retain a sampled solution 710. The walls 706 can be made of an inert or non-conductive material.

The sampled solution 710 can refer to any of the diluted samples or an aliquot thereof. At least part of the external reference electrode 702 can be in fluid communication or in fluid contact with the sampled solution 710. For example, the external reference electrode 702 can extend into or be immersed in the sampled solution 710. The external reference electrode 702 can also have a stable or well-known internal voltage and the sensor 700 can use the external reference electrode 702 to determine or measure a relative change in the potential of the active electrode 701. In one embodiment, the external reference electrode 702 can be a standalone probe or electrode. In other embodiments, the external reference electrode 702 can be coupled to the parameter analyzer 118. In some embodiments, multiple sensors (including but not limited to the first sensor and the second sensor) can share and use the same external reference electrode 702.

In one embodiment, the external reference electrode 702 can be a silver/silver chloride (Ag/AgCl) electrode. In other embodiments, the external reference electrode 702 can comprise a saturated calomel reference electrode (SCE) or a copper-copper (II) sulfate electrode (CSE). The external reference electrode 702 can also be a pseudo-reference electrode including any metal that is not part of the active electrode such as platinum, silver, gold, or a combination thereof; any metal oxide or semiconductor oxide material such as aluminum oxide, iridium oxide, silicon oxide; or any conductive polymer electrodes such as polypyrrole, polyaniline, polyacetylene, or a combination thereof.

The active electrode 701 can comprise multiple conductive layers (e.g., a stack of metallic layers) and a redox-active material 708 or layer such as a gold layer, a platinum layer, a metal oxide layer, a carbon layer, or a combination thereof on top of the multiple conductive layers. In some embodiments, the metal oxide layer can comprise an iridium oxide layer, a ruthenium oxide layer, or a combination thereof. The parameter analyzer 118 can be coupled to the active electrode 701 and the external reference electrode 702.

The parameter analyzer 118, the computing device 120, or a combination thereof can determine the ORP of the sampled solution 710 by measuring the potential difference between the external reference electrode 702 and the active electrode 701 instantly or over a period of time. As shown in FIG. 7A, the parameter analyzer 118 can be a voltmeter or any other type of high-impedance amplifier or sourcemeter. The voltmeter can measure a relative change in an equilibrium potential at an interface between the redox-active material 708 of the active electrode 701 and the sampled solution 710 containing electro-active redox species. The parameter analyzer 118 can also be used to apply a voltage or current to the active electrodes and the external reference electrode 702.

The solution characteristic of the sampled solution 710 can change as the amount of electro-active redox species changes due to the energy use, oxygen uptake or release, growth, or metabolism of the infectious agents in solution. For example, the amount of electro-active redox species in the sampled solution 710 can change as a result of cellular activity undertaken by the infectious agents in solution. As a more specific example, the amount of electron donors from Table 1 (e.g., the amount of energy carriers such as nicotinamide adenine dinucleotide (NADH) and flavin adenine dinucleotide ($FADH_2$)) in the sampled solution 710 can change due to the growth or lack thereof of the infectious agents in solution. Also, as another more specific example, the amount of oxygen depleted in the sampled solution 710 can change due to the growth or lack thereof of the infectious agents in solution.

In one embodiment, the active electrode 701 can comprise a metallic layer. The metallic layer can comprise a gold layer, a platinum layer, or a combination thereof. The active electrode 701 can also comprise multiple layers comprising a semiconductor layer having a redox-active metal oxide layer, such as iridium oxide or ruthenium oxide on top of the multiple layers. In other embodiments, the active electrode 701 can comprise one or more metallic layers, one or more redox-active metal oxide layers, one or more semiconductor layers, or any combination or stacking arrangement thereof.

FIG. 7B illustrates a schematic of another embodiment of an ORP sensor 700 used as part of the methods and systems described herein. The sensor 700 of FIG. 7B can be or refer to any of the sensors 116 depicted in FIGS. 1, 2, and 6 (including any of the sensors 116 referred to as the first sensor or the second sensor). The sensor 700 can have an on-chip reference electrode 712 disposed on the substrate layer 704 in lieu of the external reference electrode 702 of FIG. 7A. In some embodiments of the sensor 700, the active electrode 701 and the on-chip reference electrode 712 are the only electrodes of the sensor 700. The parameter analyzer 118 can also be used to apply a voltage or current to the active electrodes and the on-chip reference electrode 712.

In these and other embodiments, the on-chip reference electrode 712 can be coated by a polymeric coating. For example, the on-chip reference electrode 712 can be coated by a polyvinyl chloride (PVC) coating, a perfluorosulfonate coating (e.g., Nafion™), or a combination thereof.

The on-chip reference electrode 712 can serve the same purpose as the external reference electrode 702 except be fabricated on or integrated with the substrate layer 704. The on-chip reference electrode 712 can be located adjacent to or near the active electrode 701. The sensor 700 of FIG. 7B can serve the same function as the sensor 700 of FIG. 7A. Similar to the active electrode 701 of FIG. 7B, the on-chip reference electrode 712 can also be in fluid communication or communication with the sampled solution 710 retained within walls 706.

The on-chip reference electrode 712 can be comprised of a metal, a semiconductor material, or a combination thereof. The metal of the on-chip reference electrode 712 can be covered by an oxide layer, a silane layer, a polymer layer, or a combination thereof. In another embodiment, the on-chip reference electrode 712 can be a metal combined with a metal salt such as an Ag/AgCl on-chip reference electrode. In another embodiment, the on-chip reference electrode can be a miniaturized electrode with a well-defined potential. In some embodiments, multiple sensors can share and use the same on-chip reference electrode 712. The on-chip reference electrode 712 can comprise a saturated calomel reference electrode (SCE) or a copper-copper (II) sulfate electrode (CSE). The on-chip reference electrode 712 can also comprise a pseudo-reference electrode including any metal that is not part of the active electrode such as platinum, silver, gold, or a combination thereof; any metal oxide or semiconductor oxide material such as aluminum oxide, iridium oxide, silicon oxide; or any conductive polymer electrodes such as polypyrrole, polyaniline, polyacetylene, or a combination thereof.

Figure 8A:
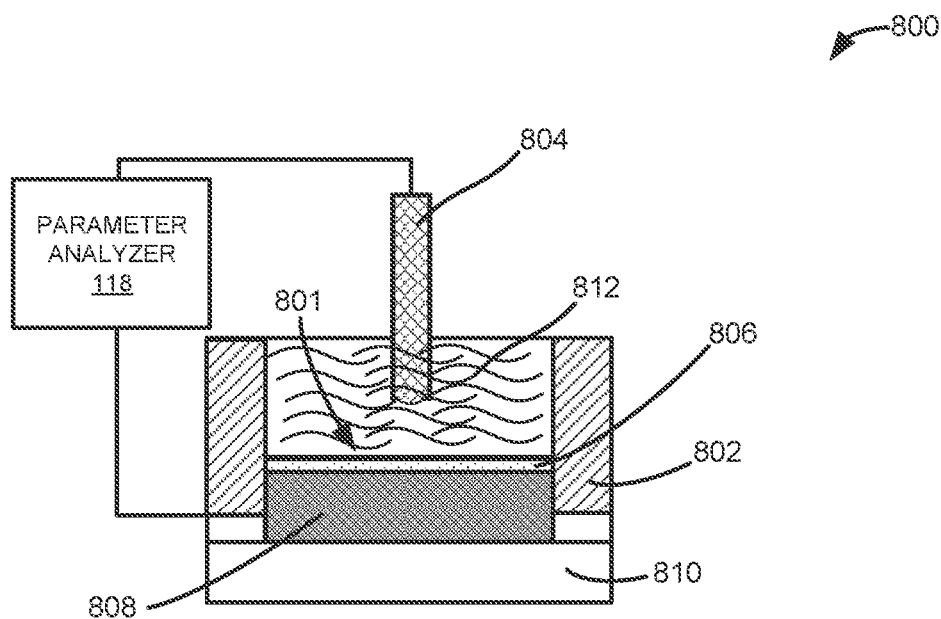
FIG. 8A illustrates a schematic of one embodiment of a pH sensor used as part of the methods and systems described herein.

FIG. 8A illustrates a schematic of one embodiment of a pH sensor 800 used as part of the methods and systems described herein. The sensor 800 of FIG. 8A can be or refer to any of the sensors 116 depicted in FIGS. 1, 2, and 6 (including any of the sensors 116 referred to as the first sensor or the second sensor). The sensor 800 can be or comprise an electrochemical cell comprising container walls 802, an active electrode 801 positioned on a substrate layer 810, and an external reference electrode 804. The active electrode 801 can comprise a functionalization layer 806 and a conductor layer 808. The sensor 800 can be configured to receive or be in fluid contact with a solution 812. For example, the sensor 800 can receive and retain the solution 812 within the container walls 802 as shown in FIG. 8A. In other embodiments not shown in the figures but contemplated by this disclosure, one or more layers of the sensor 800 can be in fluid contact with the solution 812 even though the solution 812 is not retained within the container walls 802 of the sensor 800 or the sensor 800 has no container walls 802.

In all such embodiments, the solution 812 can be any of the diluted samples or aliquots thereof. The sensor 800 can be connected or coupled to the parameter analyzer 118. In one embodiment, the parameter analyzer 118 can be coupled to both the external reference electrode 804 and the conductor layer 808. In other embodiments, the parameter analyzer 118 can be coupled to the external reference electrode 804, the conductor layer 808, as well as other layers. As shown in FIG. 8A, the external reference electrode 804 can extend into the solution 812.

When the parameter analyzer 118 is coupled to the external reference electrode 804, the conductor layer 808, or another layer, the parameter analyzer 118 can measure a difference in the electrical characteristic of the solution 812. The external reference electrode 804 can have a stable and well-known internal reference potential and can also act as a differential noise filter for removing electrical noise from measurements taken by the sensor 800. An operator or clinician can use this setup to determine or record a relative change in the electrical characteristic of the sensor 800 rather than having to ascertain an absolute change. An operator or clinician can also use the external reference electrode 804 to determine or record a relative difference between the electrical characteristics of multiple sensors 800. In one embodiment, the external reference electrode 804 can be a standalone probe or electrode. In other embodiments, the external reference electrode 804 can be coupled to the parameter analyzer 118 or a computing device 120 (not shown) connected to the parameter analyzer 118. The parameter analyzer 118 can also be used to apply a voltage or current to the active electrodes and the external reference electrode 804.

In one embodiment, the external reference electrode 804 can be a silver/silver chloride (Ag/AgCl) electrode. In other embodiments, the external reference electrode 804 can be, but is not limited to, a saturated calomel reference electrode (SCE) or a copper-copper (II) sulfate electrode (CSE).

The substrate layer 808 can be composed of, but is not limited to, any non-conducting material such as a polymer, an oxide, a ceramic, or a composite thereof. As depicted in FIG. 8A, the conductor layer 808 can be disposed on or cover the substrate layer 810.

The conductor layer 808 can be composed of, but is not limited to, a metal, a semiconducting material, a metal/metal-salt, or a combination thereof. For example, the conductor layer 808 can be composed of, but is not limited to, silicon, gold, silver, aluminum, platinum, or a composite thereof. The conductor layer 808 can also be an organic semiconductor, a carbon nanotube, graphene, an organic conductor such as those derived from polyacetylene, polyaniline, Quinacridone, Poly(3,4-ethylenedioxythiophene) or PEDOT, PEDOT: polystyrene sulfonate (PSS), or a combination thereof. The conductor layer 808 can be composed of any conducting material which allows an electrical property change to be measured, including, but is not limited to, a voltage change, a capacitance change, a conductance change, and/or a current change measured through the conductor layer 808, the functionalization layer 806, and the solution 812 to the external reference electrode 804.

As depicted in FIG. 8A, the functionalization layer 806 can be disposed on or cover the conductor layer 808. The functionalization layer 806 can comprise oxides, silanes, DNA, proteins, antibodies, self-assembled mono layers (SAMs), oxides, buffered hydrogels, PVC, parylene, polyACE, or any other biochemically active materials. The functionalization layer 806 can be configured to facilitate the sensor 800 from interacting with ions, analytes, or other molecules or byproducts in the solution 812. For example, the functionalization layer 806 can be a pH-sensitive layer or pH-active layer.

In one example, the functionalization layer 806 can comprise hydroxyl groups which can interact with hydrogen ions ($H^+$) in the solution 812. This interaction can generate a change in the electrical characteristic between the sensor 800 and the external reference electrode 804 as detected by the parameter analyzer 118. In one embodiment, this interaction can create a measurable change in the electrical characteristic of the sensor 800 at the interface between the solution 812 and the functionalization layer 806 or the interface between the solution 812 and the conductor layer 808.

For example, the parameter analyzer 118 can be a voltmeter and the voltmeter can detect a voltage (potential) change ($\Delta V$) at or near the functionalization layer 806 exposed to the solution 812. The voltage change can be determined with respect to the external reference electrode 804 extending into or in contact with the solution 812. In this embodiment, the functionalization layer 806 and the conductor layer 808 can be considered part of a working or active electrode 801.

As depicted in FIG. 8A, the solution 812, the functionalization layer 806, and the conductor layer 808 can be surrounded by the container walls 802. The container walls 802 can be made of an inert or non-conductive material. The container walls 802 can comprise, but is not limited to, a polymeric material such as polyvinyl chloride (PVC), poly (methyl methacrylate) (PMMA), polydimethylsiloxane (PDMS), a ceramic, glass, or a combination thereof.

Figure 8B:
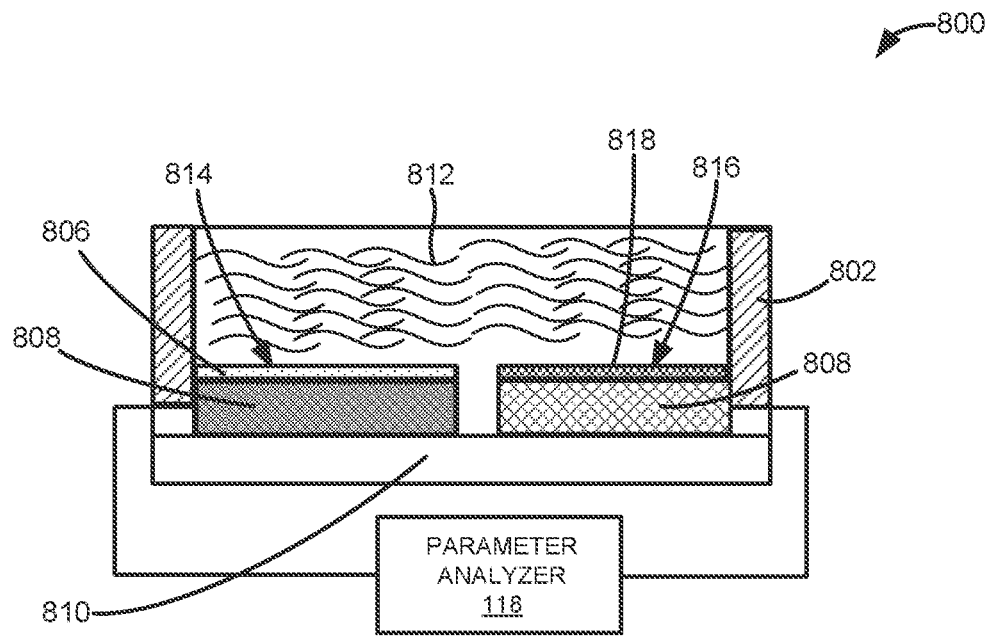
FIG. 8B illustrates a schematic of another embodiment of the pH sensor used as part of the methods and systems described herein.

FIG. 8B illustrates a schematic of another embodiment of the pH sensor 800 used as part of the methods and systems described herein. The sensor 800 can be or refer to any of the sensors 116 depicted in FIGS. 1, 2, and 6 (including any of the sensors 116 referred to as the first sensor or the second sensor).

In this embodiment, the sensor 800 can comprise an active electrode 814 or an indicator electrode and an on-chip reference electrode 816. In this embodiment, the active electrode 814 (i.e., the active electrode) and the on-chip reference electrode 816 can be disposed on the same substrate layer 810. The substrate layer 810 can be composed of the same material as the substrate layer 810 depicted in FIG. 8A.

The solution 812 can flow over or be exposed to both the active electrode 814 and the on-chip reference electrode 816 simultaneously. In this embodiment, the active electrode 814 and the on-chip reference electrode 816 can be separated by a container wall 802 or container divide.

The active electrode 814 can comprise the functionalization layer 806 disposed on or covering the conductor layer 808. The functionalization layer 806 can comprise oxides, silanes, DNA, proteins, hydroxyl group, antibodies, oxides, self-assembled mono layers (SAMs), buffered hydrogels, PVC, parylene, polyACE, or any other biochemically active materials.

As shown in FIG. 8B, a passivation layer 818 can be disposed on or cover the conductor layer 808. The passivation layer 818 can be configured to prevent the on-chip reference electrode 816 from interacting with analytes, ions, or other molecules or byproducts in the solution 812. For example, the passivation layer 818 can be a pH-insensitive layer. The passivation layer 818 can comprise silanes, self-assembled monolayers (SAMs), buffered hydrogels, parylene, polyACE, or any other biochemically inert material.

In this embodiment, the parameter analyzer 118 can have a lead connection wire, such as a copper wire, connected to the conductor layer 808 of the active electrode 814 and another lead connection wire connected to the conductor layer 808 of the on-chip reference electrode 816. The parameter analyzer 118 can also be used to apply a voltage or current to the active electrodes and the on-chip reference electrode 816.

In this and other embodiments, the sensor 800 shown in FIG. 8B miniaturizes the sensor set-up shown in FIG. 8A. The on-chip reference electrode 816 obviates the need for an external reference electrode, such as the external reference electrode 804. The on-chip reference electrode 816 can also be a silver/silver chloride (Ag/AgCl) electrode. In other embodiments, the on-chip reference electrode 816 can be, but is not limited to, a saturated calomel reference electrode (SCE) or a copper-copper (II) sulfate electrode (CSE). The on-chip reference electrode 816 provides similar functionality as that of the external reference electrode 804 in this embodiment of the sensor 800. The passivation layer 818 of the on-chip reference electrode 816 prevents the conductor layer 808 covered by the passivation layer 818 from interacting with the ions, analytes, or other molecules or byproducts in the solution 812. This allows a reader or another device from being able to differentiate the electrical signals obtained by the parameter analyzer 118. In some embodiments, the passivation layer 818 can refer to an on-chip reference electrode 816 with a well-defined potential. In other embodiments, the on-chip reference electrode 816 can be without a passivation layer 818.

In one embodiment where the conductor layer 808 is used as a reference electrode, the conductor layer 808 can be a metal covered with a metal salt such as a metal chloride. In another embodiment, the conductor layer 808 can also be covered with an oxide. For example, the conductor layer 808 can be a silver/silver chloride contact. In this embodiment, the conductor layer 808 can be covered by, but is not limited to, a passivation layer 818 such as a KCL electrolyte gel or KCL solution, to prevent the conductor layer 808 from interacting with analytes, ions, or other molecules or byproducts in the solution 812 and to act as a reference electrode.

Figure 9A:
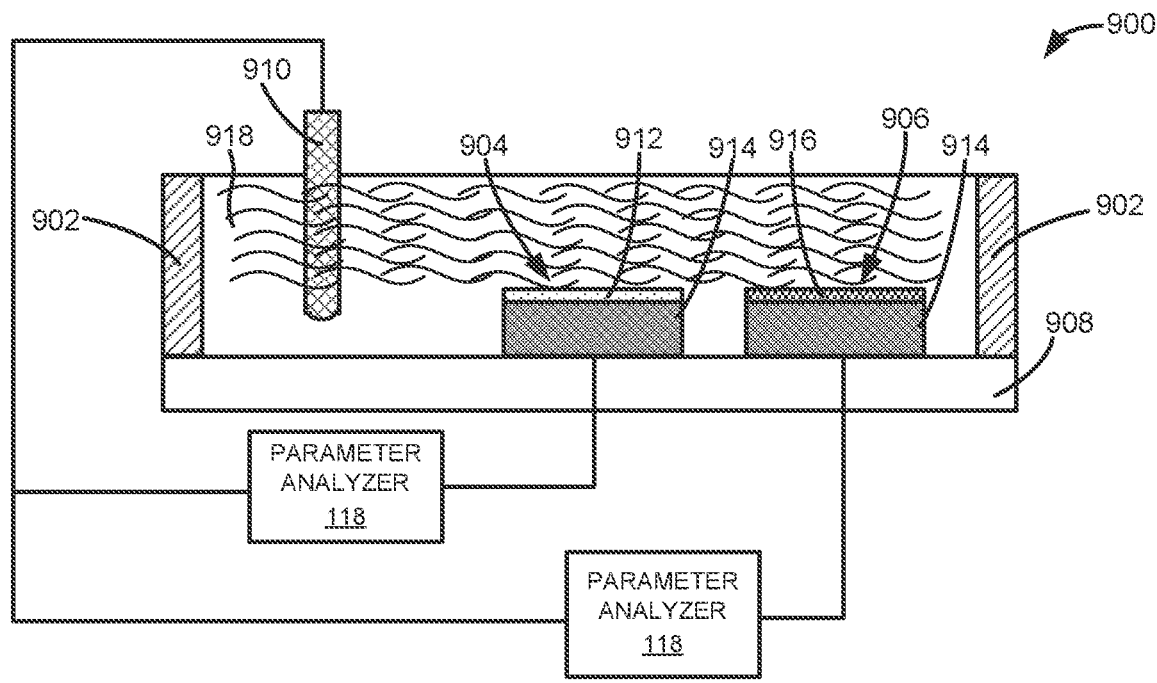
FIG. 9A illustrates a schematic of one embodiment of a combined ORP and pH sensor used as part of the methods and systems described herein.

FIG. 9A illustrates a schematic of one embodiment of a sensor 900 used as part of the methods and systems described herein. The sensor 900 of FIG. 9A can be or refer to any of the sensors 116 depicted in FIGS. 1, 2, and 6 (including any of the sensors 116 referred to as the first sensor or the second sensor). The sensor 900 can be or comprise an electrochemical cell having container walls 902, a first active electrode 904 and a second active electrode 906 positioned on a substrate layer 908, and an external reference electrode 910. Although two active electrodes are shown in FIG. 9A, it is contemplated by this disclosure and it should be understood by one of ordinary skill in the art that three or more active electrodes or multiple reference electrodes can be positioned on one substrate layer.

The first active electrode 904 can comprise a redox-active material 912 disposed or otherwise positioned on a conductor layer 914. The second active electrode 906 can comprise a functionalization layer 916 disposed or otherwise positioned on a conductor layer 914. In some embodiments, the functionalization layer 916 can be a pH sensitive layer. In these and other embodiments, the first active electrode 904 can serve as part of an ORP sensor and the second active electrode 906 can serve as part of a pH sensor.

The containers walls 902 of the sensor 900 can be configured to receive and retain a sampled solution 918. The container walls 902 can be made of an inert or non-conductive material. The container walls 902 can comprise, but is not limited to, a polymeric material such as polyvinyl chloride (PVC), poly(methyl methacrylate) (PMMA), polydimethylsiloxane (PDMS), a ceramic, glass, or a combination thereof.

In other embodiments not shown in the figures but contemplated by this disclosure, one or more layers of the sensor 900 can be in fluid contact or communication with the sampled solution 918 even though the sampled solution 918 is not retained within the container walls 902 of the sensor 900 or the sensor 900 has no container walls 902. The sampled solution 918 can be any of the diluted samples described herein or aliquots thereof.

As shown in FIG. 9A, one or more parameter analyzers 118 can be coupled to both the external reference electrode 910 and the conductor layers 914 of the first active electrode 904 and the second active electrode 906. The parameter analyzer 118 can be coupled to the external reference electrode 910 and the conductor layers 914 through one or more other layers of the sensor 900. The parameter analyzer 118 can be coupled to the first active electrode 904, the second active electrode 906, the external reference electrode 910, and any other active or reference electrodes and multiplex the signal from each of the electrodes in parallel or one after the other.

At least part of the external reference electrode 910 can be in fluid communication or in fluid contact with the sampled solution 918. As shown in FIG. 9A, at least part of the external reference electrode 910 can extend into or be immersed in the sampled solution 918.

The external reference electrode 910 can also have a stable or well-known internal voltage and can also act as a differential noise filter for removing electrical noise from measurements taken using the sensor 900. In one embodiment, the external reference electrode 910 can be a stand-alone probe or electrode coupled to the parameter analyzer 118. In other embodiments, the external reference electrode 910 can be integrated with the parameter analyzer 118. As shown in FIG. 9A, the first active electrode 904 and the second active electrode 906 can be coupled to and share the same external reference electrode 910. Although FIG. 9A shows the first active electrode 904 and the second active electrode 906 coupled to separate parameter analyzers 118, it is contemplated by this disclosure and it should be understood by one of ordinary skill in the art that the first active electrode 904 and the second active electrode 906 can be coupled to the same parameter analyzer 118.

In one embodiment, the external reference electrode 910 can be or comprise a silver/silver chloride (Ag/AgCl) electrode. In other embodiments, the external reference electrode 910 can be or comprise a saturated calomel reference electrode (SCE) or a copper-copper (II) sulfate electrode (CSE). The external reference electrode 910 can also be a pseudo-reference electrode including any metal that is not part of the active electrode such as platinum, silver, gold, or a combination thereof; any metal oxide or semiconductor oxide material such as aluminum oxide, iridium oxide, silicon oxide; or any conductive polymer electrodes such as polypyrrole, polyaniline, polyacetylene, or a combination thereof.

As depicted in FIG. 9A, each of the first active electrode 904 and the second active electrode 906 can comprise at least one conductor layer 914 disposed or otherwise positioned on the substrate layer 908. The substrate layer 908 can be composed of, but is not limited to, any non-conducting material such as a polymer, an oxide, a ceramic, or a composite thereof.

The conductor layer 914 can be composed of, but is not limited to, a metal, a semiconducting material, a metal/metal-salt, or a combination thereof. For example, the conductor layer 914 can be composed of, but is not limited to, silicon, gold, silver, aluminum, platinum, or a composite thereof. The conductor layer 914 can also be an organic semiconductor, a carbon nanotube, graphene, an organic conductor such as those derived from polyacetylene, polyaniline, Quinacridone, Poly(3,4-ethylenedioxythiophene) or PEDOT, PEDOT: polystyrene sulfonate (PSS), or a combination thereof. The conductor layer 914 can be composed of any conducting material which allows an electrical property change to be measured, including, but not limited to, a voltage change, a capacitance change, a conductance change, and/or a current change measured through the conductor layer 914, the redox-active material 912 or the functionalization layer 916, and the sampled solution 918. The conductor layer 914 can also refer to multiple conductive layers such as a stack of metallic layers. For example, the metallic layers can comprise gold layers, platinum layers, or a combination thereof.

The first active electrode 904 can comprise a redox-active material 912 or layer disposed or otherwise covering a conductor layer 914. The redox-active material 912 can comprise a gold layer, a platinum layer, a metal oxide layer, a carbon layer, or a combination thereof on top of the conductor layer 914 (or multiple conductor layers 914). In some embodiments, the metal oxide layer can comprise an iridium oxide layer, a ruthenium oxide layer, or a combination thereof.

The parameter analyzer 118 (or another device coupled to the parameter analyzer 118, such as the computing device 120, not shown) coupled to the first active electrode 904 and the external reference electrode 910 can determine the ORP of the sampled solution 918 by measuring the potential difference between the external reference electrode 910 and the first active electrode 904.

In some embodiments, the parameter analyzer 118 can be a voltmeter or any other type of high-impedance amplifier or sourcemeter. The parameter analyzer 118 can measure a relative change in an equilibrium potential at an interface between the redox-active material 912 and the sampled solution 918 containing the electro-active redox species. The parameter analyzer 118 can also measure a relative change in the equilibrium potential at an interface between the conductor layer 914 and the sampled solution 918 containing the electro-active redox species. The change in the equilibrium potential can be measured with respect to the external reference electrode 910. The parameter analyzer 118 can also be used to apply a voltage or current to the external reference electrode 910 or the active electrodes.

The solution characteristic of the sampled solution 918 can change as the amount of electro-active redox species changes due to the energy use, oxygen uptake or release, growth, or metabolism of the infectious agents in solution. For example, the amount of electro-active redox species in the sampled solution 918 can change as a result of cellular activity undertaken by the infectious agents in solution. As a more specific example, the amount of electron donors (e.g., the amount of energy carriers such as nicotinamide adenine dinucleotide (NADH) and flavin adenine dinucleotide ($FADH_2$)) in the sampled solution 918 can change due to the growth or lack thereof of the infectious agents in solution. Also, as another more specific example, the amount of oxygen depleted in the sampled solution 918 can change due to the growth or lack thereof of the infectious agents in solution.

The second active electrode 906 can comprise a functionalization layer 916 disposed or otherwise covering a conductor layer 914. The functionalization layer 916 can comprise oxides, silanes, DNA, proteins, antibodies, self-assembled mono layers (SAMs), oxides, buffered hydrogels, PVC, parylene, polyACE, or any other biochemically active materials. The functionalization layer 916 can be a pH-sensitive layer or pH-active layer configured to interact with ions, analytes, or other molecules or byproducts in the sampled solution 918. For example, the functionalization layer 916 can comprise hydroxyl groups which can interact with hydrogen ions ($H^+$) in the sampled solution 918.

The parameter analyzer 118 (or another device coupled to the parameter analyzer 118, such as the computing device 120, not shown) coupled to the second active electrode 906 and the external reference electrode 910 can determine the pH of the sampled solution 918 by measuring the potential difference between the external reference electrode 910 and the second active electrode 906.

The parameter analyzer 118 can measure a relative change in an equilibrium potential at an interface between the functionalization layer 916 and the sampled solution 918 containing the ions, analytes, or other molecules. The parameter analyzer 118 can also measure a relative change in the equilibrium potential at an interface between the conductor layer 914 and the sampled solution 918 containing the ions, analytes, or other molecules. The solution characteristic of the sampled solution 918 can change as the amount of ions, analytes, or other molecules changes due to the energy use, oxygen uptake or release, growth, or metabolism of the infectious agents in solution. For example, the amount of hydrogen ions ($H^+$) in the sampled solution 918 can change as a result of cellular activity undertaken by the infectious agents in solution. The change in the equilibrium potential can be measured with respect to the external reference electrode 910. In these instances, what is measured by the parameter analyzer 118 (or the computing device 120 coupled to the parameter analyzer 118, not shown) is a relative change in the electrical characteristic of the sensor 900.

Figure 9B:
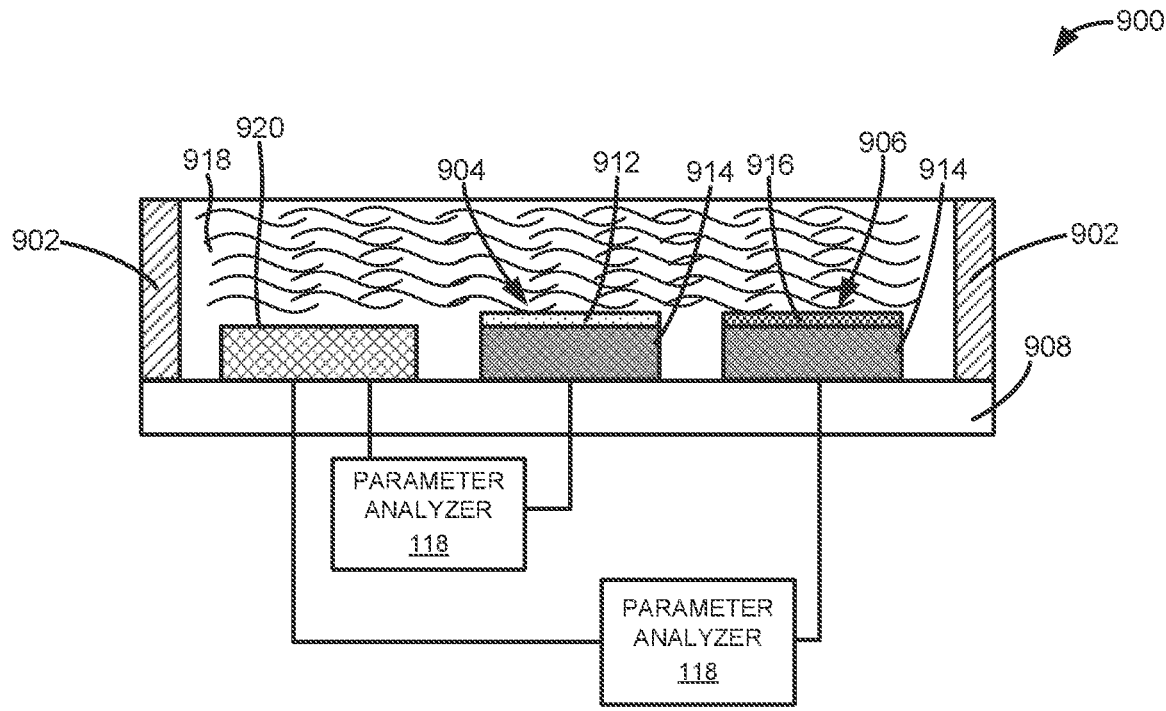
FIG. 9B illustrates a schematic of another embodiment of a combined ORP and pH sensor used as part of the methods and systems described herein.

FIG. 9B illustrates a schematic of another embodiment of the sensor 900 used as part of the methods and systems described herein. The sensor 900 of FIG. 9B can be or refer to any of the sensors 116 depicted in FIGS. 1, 2, and 6 (including any of the sensors 116 referred to as the first sensor or the second sensor).

The sensor 900 can be or comprise an electrochemical cell having container walls 902, a first active electrode 904 and a second active electrode 906 positioned on a substrate layer 908, and an on-chip reference electrode 920 positioned on the same substrate layer 908. Although two active electrodes are shown in FIG. 9B, it is contemplated by this disclosure and it should be understood by one of ordinary skill in the art that three or more active electrodes or multiple reference electrodes can be positioned on one substrate layer.

The container walls 902, the first active electrode 904, the second active electrode 906, and the substrate layer 908 of FIG. 9B can be the same as the container walls 902, the first active electrode 904, the second active electrode 906, and the substrate layer 908, respectively, of FIG. 9A. The sampled solution 918 can be in fluid communication or otherwise exposed to the on-chip reference electrode 920, the first active electrode 904, and the second active electrode 906 at the same time.

Although not shown in FIG. 9B, a passivation layer can be disposed on or cover the on-chip reference electrode 920. The passivation layer can be configured to prevent the on-chip reference electrode 920 from interacting with redox-active species, analytes, ions, or other molecules in the sampled solution 918. For example, the passivation layer can be a pH-insensitive layer. The passivation layer can comprise silanes, self-assembled monolayers (SAMs), buffered hydrogels, parylene, polyACE, or any other biochemically inert material.

In this embodiment, the parameter analyzer 118 can have a lead connection wire, such as a copper wire, coupled to the conductor layers 914 of the active electrodes and another lead connection wire connected to the on-chip reference electrode 920. The parameter analyzer 118 can be coupled to the first active electrode 904, the second active electrode 906, the on-chip reference electrode 920, and any other active or reference electrodes and multiplex the signal from each of the electrodes in parallel or one after the other. The parameter analyzer 118 can also be used to apply a voltage or current to the on-chip reference electrode 920 or the active electrodes.

In this and other embodiments, the sensor 900 shown in FIG. 9B miniaturizes the sensor set-up shown in FIG. 9A. The on-chip reference electrode 920 obviates the need for an external reference electrode, such as the external reference electrode 910. The on-chip reference electrode 920 can also be a silver/silver chloride (Ag/AgCl) electrode. In other embodiments, the on-chip reference electrode 920 can be, but is not limited to, a saturated calomel reference electrode (SCE) or a copper-copper (II) sulfate electrode (CSE). The on-chip reference electrode 920 provides similar functionality as that of the external reference electrode 910.

In one embodiment, a conductor layer 914 can be used as an on-chip reference electrode 920. The conductor layer 914 serving as the on-chip reference electrode 920 can be a metal covered with a metal salt such as a metal chloride. In another embodiment, the conductor layer 914 serving as the on-chip reference electrode 920 can also be covered with an oxide. For example, the conductor layer 914 can be a silver/silver chloride contact. In some embodiments, the conductor layer 914 can be covered by a passivation layer such as a KCL electrolyte gel or KCL solution to prevent the conductor layer 914 from interacting with redox-active species, analytes, ions, or other molecules in the sampled solution 918 and to act as a reference electrode.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. For example, the flowcharts or process flows depicted in the figures do not require the particular order shown to achieve the desired result. Moreover, additional steps or operations may be provided or steps or operations may be eliminated to achieve the desired result.

It will be understood by one of ordinary skill in the art that all or a portion of the methods disclosed herein may be embodied in a non-transitory machine readable or accessible medium comprising instructions readable or executable by a processor or processing unit of a computing device or other type of machine.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure. The scope of the present invention is limited only by the appended claims.

What is claimed is:

1. A method of determining a concentration of a bacteria of an unknown strain in a target sample, the method comprising:
    diluting a first aliquot of the target sample comprising the bacteria of the unknown strain by a first dilution factor ($DF_1$) to yield a first diluted sample;
    diluting a second aliquot of the target sample comprising the bacteria of the unknown strain by a second dilution factor ($DF_2$) to yield a second diluted sample;
    exposing the first diluted sample to a first oxidation reduction potential (ORP) sensor and the second diluted sample to a second ORP sensor, wherein each of the first ORP sensor and the second ORP sensor comprises a redox-active material, wherein the ORP is monitored in the absence of any added reporter molecules in any of the first diluted sample or the second diluted sample;
    determining, using a parameter analyzer or a computing device communicatively coupled to the first ORP sensor and the second ORP sensor, a first time-to-detection ($TTD_1$) representing the time it takes the ORP of the first diluted sample to undertake a predetermined threshold change;
    determining, using the parameter analyzer or the computing device communicatively coupled to the first ORP sensor and the second ORP sensor, a second time-to-detection ($TTD_2$) representing the time it takes the ORP of the second diluted sample to undertake the predetermined threshold change;
    calculating, using the parameter analyzer or the computing device, an average calibration curve slope ($m_{avg}$) and an average calibration curve y-intercept ($b_{avg}$) from equation parameters obtained from multiple calibration curves representing growth behavior of one or more bacteria of different known strains;
    calculating, using the parameter analyzer or the computing device, a corrected calibration curve slope ($m_{corr}$) using at least the $TTD_2$, the $TTD_1$, the $DF_2$, and the $DF_1$;
    calculating, using the parameter analyzer or the computing device, a corrected calibration curve y-intercept ($b_{corr}$) using at least the $b_{avg}$, the $m_{corr}$, and the $m_{avg}$; and
    determining, using the parameter analyzer or the computing device, the concentration of the bacteria of the unknown strain in the target sample using at least the $m_{corr}$, the $b_{corr}$, and either the $TTD_1$ and the $DF_1$ or the $TTD_2$ and the $DF_2$.

2. The method of claim 1, wherein the one or more bacteria of the different known strains comprise at least a first bacteria and a second bacteria, wherein the first bacteria is a different species from the second bacteria.

3. The method of claim 1, wherein the one or more bacteria of the different known strains are the same species as the bacteria of the unknown strain.

4. The method of claim 1, further comprising generating the multiple calibration curves prior to calculating the $m_{avg}$ and the $b_{avg}$ by:
    preparing cultures comprising the one or more bacteria of the different known strains, wherein the prepared cultures comprise different initial concentrations ($N_{initial}$) of a bacteria of a known strain;

monitoring, using one or more sensors, changes in the ORP of each of the prepared cultures over time;

determining a calibration time-to-detection ($TTD_{calibration}$) of each of the prepared cultures representing the time it takes the ORP of each of the prepared cultures to undertake the predetermined threshold change;

fitting each of the multiple calibration curves to $TTD_{calibration}$ data and $N_{initial}$ data related to a specific known strain using the relationship:

$$TTD_{calibration} = m_{strain\_specific} \times \log_a(N_{initial}) + b_{strain\_specific},$$

wherein a is any positive real number other than 1, wherein $m_{strain\_specific}$ is a strain-specific calibration curve slope, and wherein $b_{strain\_specific}$ is a strain-specific calibration curve y-intercept.

5. The method of claim 4, wherein calculating the $m_{avg}$ is taking an average of multiple $m_{strain\_specific}$ values and calculating the $b_{avg}$ is taking an average of multiple $b_{strain\_specific}$ values.

6. The method of claim 4, wherein calculating the $m_{corr}$ comprises using the relationship:

$$m_{corr} = \frac{-(TTD2 - TTD1)}{\log_a\left(\frac{DF2}{DF1}\right)}.$$

7. The method of claim 6, wherein calculating the $b_{corr}$ comprises using the relationship:

$$b_{corr} = \frac{m_{corr}}{m_{avg}} \times b_{avg}.$$

8. The method of claim 7, wherein determining the concentration of the bacteria of the unknown strain ($Conc_{target}$) comprises using the relationship:

$$Conc_{target} = DF_1 \times a^{\left(\frac{TTD_1 - b_{corr}}{m_{corr}}\right)}.$$

9. The method of claim 7, wherein determining the concentration of the bacteria of the unknown strain ($Conc_{target}$) comprises using the relationship:

$$Conc_{target} = DF_2 \times a^{\left(\frac{TTD_2 - b_{corr}}{m_{corr}}\right)}.$$

10. The method of claim 1, wherein the first aliquot and the second aliquot of the sample are diluted with growth media.

11. The method of claim 1, wherein the first ORP sensor and the second ORP sensor each comprise at least an active electrode and a reference electrode.

12. The method of claim 1, wherein the predetermined threshold change is a change in the ORP of between approximately −100 mV and −700 mV.

13. The method of claim 1, wherein the redox-active material comprises a gold layer, a platinum layer, a metal oxide layer, a carbon layer, or a combination thereof.

* * * * *